(12) United States Patent
Bothe et al.

(10) Patent No.: US 9,714,266 B2
(45) Date of Patent: Jul. 25, 2017

(54) ESTRA-1,3,5(10),16-TETRAENE-3-CARBOXAMIDES FOR INHIBITION OF 17.BETA.-HYDROXYSTEROID DEHYDROGENASE (AKR1C3)

(71) Applicant: BAYER PHARMA AKTIENGESELLSCHAFT, Berlin (DE)

(72) Inventors: Ulrich Bothe, Berlin (DE); Matthias Busemann, Berlin (DE); Naomi Barak, Berlin (DE); Andrea Rotgeri, Berlin (DE); Oliver Martin Fischer, Berlin (DE); Tobias Marquardt, Wuppertal (DE)

(73) Assignee: BAYER PHARMA AKTIENGESELLSCHAFT, Berlin (DE)

( * ) Notice: Subject to any disclaimer, the term of this patent is extended or adjusted under 35 U.S.C. 154(b) by 0 days.

(21) Appl. No.: 14/770,444

(22) PCT Filed: Feb. 18, 2014

(86) PCT No.: PCT/EP2014/053094
§ 371 (c)(1),
(2) Date: Aug. 25, 2015

(87) PCT Pub. No.: WO2014/128108
PCT Pub. Date: Aug. 28, 2014

(65) Prior Publication Data
US 2016/0024142 A1   Jan. 28, 2016

(30) Foreign Application Priority Data
Feb. 21, 2013 (EP) .................................. 13156125

(51) Int. Cl.
| A61K 31/58 | (2006.01) |
| A61K 31/56 | (2006.01) |
| C07J 43/00 | (2006.01) |
| A61K 45/06 | (2006.01) |

(52) U.S. Cl.
CPC ............ *C07J 43/003* (2013.01); *A61K 31/58* (2013.01); *A61K 45/06* (2013.01)

(58) Field of Classification Search
CPC ......... C07J 43/003; A61K 31/58; A61K 45/06
USPC ............................... 514/176, 171; 540/95, 96
See application file for complete search history.

(56) References Cited

U.S. PATENT DOCUMENTS

| 5,604,213 | A | 2/1997 | Barrie et al. |
| 6,541,463 | B1 | 4/2003 | Labrie et al. |
| 2005/0203075 | A1 | 9/2005 | Agoston et al. |
| 2009/0181960 | A1 | 7/2009 | Nimi et al. |
| 2010/0190826 | A1 | 7/2010 | Kakefuda et al. |
| 2014/0249119 | A1 | 9/2014 | Bothe et al. |
| 2015/0210734 | A1 | 7/2015 | Bothe et al. |

FOREIGN PATENT DOCUMENTS

| WO | 9831702 | 7/1998 |
| WO | 9845315 | 10/1998 |
| WO | 9946279 | 9/1999 |
| WO | 0007576 | 2/2000 |
| WO | 2007100066 | 9/2007 |
| WO | 2008065100 | 6/2008 |
| WO | 2008077810 | 7/2008 |
| WO | 2009120565 | 10/2009 |
| WO | 2010091306 | 8/2010 |
| WO | 2011034954 | 11/2011 |
| WO | 2013045407 | 4/2013 |
| WO | 2013009274 | 1/2014 |

OTHER PUBLICATIONS

Adeniji et al., "Development of Potent and Selective Inhibitors of Aldo-Keto Reductase 1C3 (Type 5 17β-Hydroxysteroid Dehydrogenase) Based on N-Phenyl-Aminobenzoates and Their Structure-Activity Relationships," J. Med. Chem. 2012, 55, 2311-2323.

Azzarello, Joseph T, "Expression of AKR1C3 in Renal Cell Carcinoma, Papillary Urothelial Carcinoma, and Wilms' Tumor", Int J Clin Exp Pathol, 3(2), (2009), 147-155.

(Continued)

*Primary Examiner* — Barbara P Badio
(74) *Attorney, Agent, or Firm* — Nixon & Vanderhye P.C.

(57) ABSTRACT

The invention relates to AKR1C3 inhibitors of formula (I) and to processes for preparation thereof, to the use thereof for treatment and/or prophylaxis of diseases and to the use thereof for production of medicaments for treatment and/or prophylaxis of diseases, especially of bleeding disorders and endometriosis.

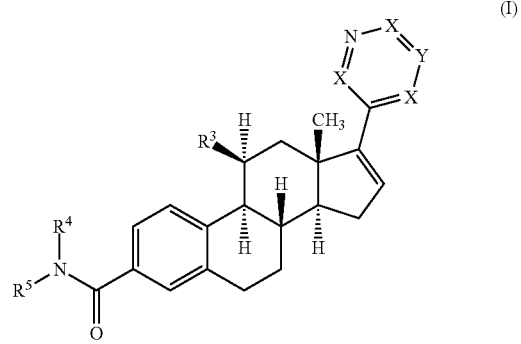

10 Claims, No Drawings

(56) References Cited

OTHER PUBLICATIONS

Birtwistle, Jane, "The Aldo-Keto Reductase AKR1C3 Contributes to 7,12-Dimethylbenz(A) Anthracene-3,4-Dihydrodiol Mediated Oxidative DNA Damage in Myeloid Cells: Implications for Leukemogenesis", Mutat Res, 662(1-2), (2009), 67-74.
Brožič et al., "Selective Inhibitors of Aldo-Keto Reductases AKR1C1 and AKR1C3 Discovered by Virtual Screening of a Fragment Library," J. Med. Chem. 2012, 55, 7417-7424.
Bydal, Patrick, "Steroidal Lactones As Inhibitors of 17β-hydroxysteroid Dehydrogenase Type 5: Chemical Synthesis, Enzyme Inhibitory Activity, and Assessment of Estrogenic and androgenic activities", Eur J of Med Chem, 44, (2009), 632-644.
Byrns, "Aldo-keto Reductase 1C3 Expression in MCF-7 Cells Reveals Roles in Steroid Hormone and Prostglandin Metabolism That May Explain Its Over-Expression in Breast Cancer", J Steroid Biochem Mol Biol, 118(3), (2010), 177-187.
Byrns, Michael C, "Inhibitors of Type 5 17β-hydroxysteroid Dehydrogenase (AKR1C3): Overview and Structural Insights", Journal Steroid Biochem Molecular Biology, 125, (2011), 95-104.
Cacchi, Sandro, "Palladium-Catalyzed Reaction of Enol Triflates with 1-Alkynes. A New Route to Conjugated Enynes", Synthesis, 4, (1986), 320-322.
Colombe, Laurent, "Prostaglandin Metabolism in Human Hair Follicle", Exp Dermatol, 16(9), (2007), 762-769.
Czako, Barbara, "Discovery of Potent and Practical Antiangiogenic Agents Inspired by Cortistatin A", JACS, 131, (2009), 9014-9019.
Day, Joanna M, "Design and Validation of Specific Inhibitors of 17β-hydroxysteroid Dehydrogenases for Therapeutic Application in Breast and Prostate Cancer, and in Endometriosis", Endocrine-Related Cancer, 15, (2008), 665-692.
Deluca, Dominga, "Inhibitory Effects of Fluorine-Substituted Estrogens on the Activity of 17beta-hydroxysteroid Dehydrogenases", Mol. Cell Endocrinol, 248, (2006), 218-224.
Delvoux Bert, "Increased Production of 17β-Estradiol in Endometriosis Lesions is the Result of Impaired Metabolism", Endocrinol Metab., 94, (2009), 876-883.
Dufort, Isabelle, "Characteristics of a Highly Labile Human Type 5 17β-Hydroxysteroid Dehydrogenase", Endocrinology, 140 , (1999), 568-574.
Figueroa, Jonine D, "Bladder Cancer Risk and Genetic Variation in AKR1C3 and Other Metabolizing Genes", Carcinogenesis, 29(10), (2008), 1955-1962.
Fung, K-M, "Increased Expression of Type 2 3α-hydroxysteroid Dehydrogenase/type 5 17β-Hydroxysteroid Dehydrogenase (AKR1C3) and Its Relationship with Androgen Receptor in Prostate Carcinoma", Endocr Relat Cancer, 13(1), (2006), 169-180.
Haidar, Samer, "Novel Steroidal Pyrimidyl Inhibitors of P450 17 (17α-hydroxylase/C17-20 lyase)", Archiv der Pharmizie,(Weinheim, Germany) 334, (2001), 373-374.
Halim, Marlin, "Imaging Induction of Cytoprotective Enzymes in Intact Human Cells: Coumberone, a Metabolic Reporter for Human AKR1C Enzymes Reveals Activation by Panaxytriol, an Active Component of Red Ginseng", J. Am. Chem. Soc., 130, (2008), 14123-14128.
Harnisch, Wolfram, "A Novel Approach to Cardenolides", J. Org. Chem., 50, (1985), 1990-1992.
He, Chunyan, "A Large-Scale Candidate Gene Association Study of Age at Menarche and Age at Natural Menopause", Hum Genet, 125(5), (2010), 515-527.
Heck, R. F., "Palladium-Catalyzed Vinylic Hydrogen Substitution Reactions with Aryl, Benzyl, and Styryl Halides", J. Org. Chem., vol. 37, No. 14, (1972), 2320-2322.
Horwitz, Jerome, "In Vitro Inhibition of Estrogen Sulfoconjugation by Some 2- and 4-Substituted Estra-1,3,5(10)-trien-17β-ols", J. Med Chem, 29, (1986), 692-698.

Jamieson et al., "3-(3,4-Dihydroisoquinolin-2(1H)-ylsulfonyl)benzoic Acids: Highly Potent and Selective Inhibitors of the Type 5 17-β-Hydroxysteroid Dehydrogenase AKR1C3," J. Med. Chem. 55, (2012), 7746-7758.
Knapp, David M, "A General Solution for Unstable Boronic Acids:Slow-Release Cross-Coupling from Air-Stable MIDA Boronates", J. Am. Chem. Soc., 131, (2009), 6961-6963.
Lan, Qing, "Genetic Polymorphisms in the Oxidative Stress Pathway and Susceptibility to Non-Hodgkin Lymphoma", Hum Genet, 121(2), (2007), 161-168.
Lan, Qing, "Oxidative Damage-Related Genes AKR1C3 and 0GG1 Modulate Risks for Lung Cancer Due to Exposure to PAH-Rich Coal Combustion Emissions", Carcinogenesis, 25(11), (2004), 2177-2181.
Lovering, Andrew L, "Crystal Structures of Prostaglandin D2 11-Ketoreductase (AKR1C3) in Complex with the Nonsteroidal Anti-Inflammatory Drugs Flufenamic Acid and Indomethacin", Cancer Res, 64(5), (2004), 1802-1810.
Molander, Gary A, "Scope of the Suzuki—Miyaura Cross-Coupling Reactions of Potassium Heteroaryltrifluoroborates", J. Org. Chem., 74, (2009), 973-980.
Moreira, V. M., "CYP17 Inhibitors for Preostate Cancer Treatment—An Update", Curr Med Chem., vol. 15, No. 9, (2008), 868-899.
Mostaghel, Elahe A, "Resistance to CYP17A1 Inhibition with Abiraterone in Castraion-Resistant Prostate Cancer: Induction of Steroidogenesis and Androgen Receptor Splice Variants", Clin Cancer Res, 17 (18), (2011), 5913-5925.
Oster, Alexander, "Bicyclic Substituted Hydroxyphenylmethanones as Novel Inhibitors of 17β-Hydroxysteroid Dehydrogenase Type 1 (17β-HSD1) for the Treatment of Estrogen-Dependent Diseases", J. Med. Chem., (2010), 8176-8186.
Penning, Trevor M, "Aldo-keto Reductase (AKR) 1C3: Role in Prostate Disease and the Development of Specific Inhibitors", Mol Cell Endocrinol, 248 (1-2), (2006), 182-191.
Pierrou, Stefan, "Expression of Genes Involved in Oxidative Stress Responses in Airway Epithelial Cells of Smokers with Chronic Obstructive Pulmonary Disease", Am J Respir Crit Care, 175(6), (2007), 577-586.
Potter, "Novel Steroidal Inhibitors of Human Cytochrome P45017α (17α-Hydroxylase-C17,20-lyase); Potential Agents for the Treatment of Prostatic Cancer", J. Med. Chem., 38, (1995), 2463-2471.
Qin Kenan, "Identification of a Functional Polymorphism of the Human Type 5 17β-Hydroxysteroid Dehydrogenase Gene Associated with Polycystic Ovary Syndrome", J. Endocrinol Metab, 91(1), (2006), 270-276.
Rizner, Tea Lanisnik, "AKR1C1 and AKR1C3 May Determine Progesterone and Estrogen Ratios in Endometrial Cancer", Mol Cell Endocrinol, 248(1-2), (2006), 126-135.
Roberts, "Polymorphisms in Genes Involved in Sex Hormone Metabolism May Increase Risk of Benign Prostatic Hyperplasia", Prostate, 66(4), (2006), 392-404.
Smuc, Tina, "Disturbed Estrogen and Progesterone Action in Ovarian Endometriosis", Mol Cell Endocrinol, 301 (1-2), (2009), 59-64.
Svensson, Per-Arne, "Regulation of Human Aldoketoreductase 1C3 (AKR1C3) Gene Expression in the Adipose Tissue", Cell Mol Biol Lett, 13(4), (2008), 599-613.
Yee, Dominic J, "Flurogenic Metabolic Probes for Direct Activity Readout of Redox Enzymes: Selective Measurement of Human AKR1C2 in Living Cells", Proc. Natl. Acad. Sci., 103, (2006), 13304-13309.
Zhang Xuqing, "An efficient synthesis of novel estrieno[2.3-b] and [3.4-c]pyrroles", Tetrahedron Letters, 44, (2003), 3071-3074.
Marchais-Oberwinkler, Sandrine, "17-β-Hydroxysteroid dehydrogenases (17-β-HSDs) as therapeutic targets: Protein structures, functions, and recent progress in inhibitor development", J Steroid Biochem Molecular Biol, 125 (2011), 66-82.
Messinger, Josef, "Estone C15 derivatives—A new class of 17β-Hydroxysteroid dehydrogenase type 1 inhibitors," Molecular Cellular Endocrinol, 301,(2009), 216-224.
Penning, Trevor M, "Structure-function aspects and inhibitor design of type 5 17β-hydroxysteroid dehydrogenase (AKR1C3)", Mol. Cell. Endocrinol. Bd., 171 (2001), 137-149.

ESTRA-1,3,5(10),16-TETRAENE-3-CARBOXAMIDES FOR INHIBITION OF 17.BETA.-HYDROXYSTEROID DEHYDROGENASE (AKR1C3)

The invention relates to AKR1C3 inhibitors and to processes for preparation thereof, to the use thereof for treatment and/or prophylaxis of diseases and to the use thereof for production of medicaments for treatment and/or prophylaxis of diseases, especially of bleeding disorders and endometriosis.

The aldo-keto reductase 1C3 (AKR1C3; synonyms: type 5 17β-hydroxysteroid dehydrogenase or prostaglandin F synthase) is a multifunctional enzyme and catalyses, among other processes, the reduction of 4-androstene-3,17-dione (a weak androgen) to testosterone (a potent androgen) and of oestrone (a weak oestrogen) to 17β-oestradiol (a strong oestrogen). In addition, the reduction of prostaglandin (PG) H2 to PGF2α and PGD2 to 9α,11β-PGF2 is inhibited (T. M. Penning et. al., 2006, 'Aldo-keto reductase (AKR) 1C3: Role in prostate disease and the development of specific inhibitors', Molecular and Cellular Endocrinology 248(1-2), 182-191).

The local formation of oestradiol (E2) plays a central role for the initiation and the progression of breast cancers and endometriosis. The reduction in the tissue levels of oestrogens and especially of oestradiol is achieved by the therapeutic administration of aromatase inhibitors (in order to inhibit the formation of oestrogens from androgens) and of sulphatase inhibitors (in order to block the formation of oestrone from oestrone sulphate). However, both therapeutic approaches have the disadvantage that systemic oestrogen levels are radically reduced (A. Oster et. al., *J. Med. Chem.* 2010, 53, 8176-8186). Recently, it has been demonstrated experimentally that endometriotic lesions are capable of local synthesis of oestradiol (B. Delvoux et al., J Clin Endocrinol Metab. 2009, 94, 876-883). For the subtype of ovarian endometriosis, overexpression of AKR1C3 mRNA has been described (T. Smuc et al., Mol Cell Endocrinol. 2009 Mar. 25; 301(1-2): 59-64).

There is a great need for the identification of novel inhibitors of the enzyme AKR1C3, since inhibitors have potential for treatment of hormone-dependent disorders, for example endometriosis, but also for treatment of hormone-independent disorders (M. C. Byrns, Y. Jin, T. M. Penning, Journal of Steroid Biochemistry and Molecular Biology (2010); A. L. Lovering et. al., *Cancer Res* 64(5), 1802-1810). As well as endometriosis, these also include prostate cancer (K. M. Fung et al., *Endocr Relat Cancer* 13(1), 169-180), prostate hyperplasia (R. O. Roberts et al., *Prostate* 66(4), 392-404), endometrial carcinoma (T. L. Rizner et al., *Mol Cell Endocrinol* 2006 248(1-2), 126-135), polycystic ovary syndrome (K. Qin et al., *J Endocrinol Metab* 2006, 91(1), 270-276), pulmonary carcinoma (Q. Lan et al., *Carcinogenesis* 2004, 25(11), 2177-2181), non-Hodgkins lymphoma (Q. Lan et al., *Hum Genet* 2007, 121(2), 161-168), hair loss (L. Colombe et al., *Exp Dermatol* 2007, 16(9), 762-769), obesity (P. A. Svensson et al., *Cell Mol Biol Lett* 2008, 13(4), 599-613), bladder carcinoma (J. D. Figueroa, *Carcinogenesis* 2008, 29(10), 1955-1962), chronic myeloid leukaemia (J. Birtwistle, *Mutat Res* 2009, 662(1-2), 67-74), renal cell carcinoma (J. T. Azzarello, *Int J Clin Exp Pathol* 2009, 3(2), 147-155), breast cancer (M. C. Byrns, *J Steroid Biochem Mol Biol* 2010, 118(3), 177-187), premature sexual maturity (C. He, *Hum Genet* 2010, 128(5), 515-527) and chronic obstructive pulmonary disease (S. Pierrou, *Am J Respir Crit Care* 2007, 175(6), 577-586).

Some inhibitors of AKR1C3 are known (review article: Joanna M. Day, Helena J. Tutill, Atul Purohit and Michael J. Reed, Endocrine-Related Cancer (2008) 15, 665-692; see also patent applications US20100190826, WO2007/100066 and P. Brožič et al., *J. Med. Chem.* 2012, 55, 7417-7424, A. O. Adenijii et al., *J. Med. Chem.* 2012, 55, 2311-2323 and S. M. F. Jamieson et al., *J. Med. Chem.* 2012, 55, 7746-7758). An example of a steroidal substance which has been described is EM-1404, based on the oestratriene skeleton with a spirolactone unit at position 17 (F. Labrie et al. U.S. Pat. No. 6,541,463; 2003).

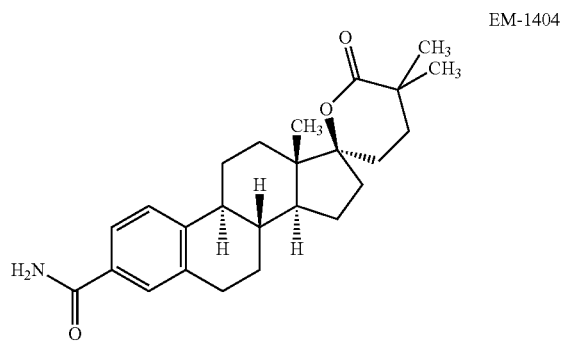

EM-1404

Further steroidal AKR1C3 inhibitors with a lactone unit were described in P. Bydal, Van Luu-The, F. Labrie, D. Poirier, European Journal of Medicinal Chemistry 2009, 44, 632-644. Fluorinated oestratriene derivatives were described in D. Deluca, G. Moller, A. Rosinus, W. Elger, A. Hillisch, J. Adamski, Mol. Cell. Endocrinol. 2006, 248, 218-224.

U.S. Pat. No. 5,604,213 (S. E. Barrie et al.) described 17-(3-pyridyl)oestra-1,3,5(10),16-tetraen-3-ol, a structure substituted on carbon atom 3 by a free hydroxyl group, as a 17α-hydroxylase/C17-20 lyase (Cyp17A1) inhibitor, but not as an AKR1C3 inhibitor.

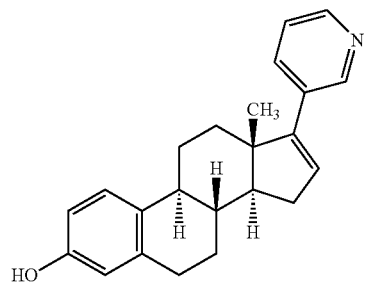

17-(3-Pyridyl)oestra-1,3,5(10),16-tetraen-3-ol 17-(3-Pyridyl)oestra-1,3,5(10),16-tetraene derivatives substituted at position 3 by a carboxamide group are not described in U.S. Pat. No. 5,604,213.

The application US2005/0203075 describes oestra-1,3,5 (10),16-tetraene derivatives substituted by a —CONH$_2$ group at the 3 position as having antiproliferative and antiangiogenetic action, without reference to a specific molecular target. However, these derivatives are not substituted by a heterocycle at position 17 of the oestra-1,3,5(10), 16-tetraene skeleton.

A review of 17-pyridyl- and 17-pyrimidinylandrostane derivatives which are described as Cyp17A1 inhibitors can be found in V. M. Moreira et al. *Current Medicinal Chemistry*, 2008 Vol. 15, No. 9.

Even though numerous AKR1C3 inhibitors have been described, there is still a need for substances having improved properties, for example improved solubility.

It is an object of the present invention to provide substances active as AKR1C3 inhibitors and having improved properties, for example having improved solubility.

The present invention provides compounds of the formula (I)

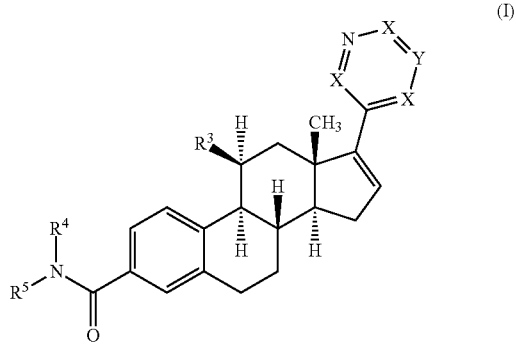

where

X is independently carbon or nitrogen, where the carbon may be substituted by $R^1$, Y is carbon or nitrogen, where the carbon may be substituted by $R^2$, $R^1$ and $R^2$
are each independently hydrogen, halogen, $C_1$-$C_6$-alkyl, $C_2$-$C_6$-alkenyl, $C_2$-$C_6$-alkynyl, $C_3$-$C_6$-cycloalkyl, $C_1$-$C_6$-alkoxy, $C_1$-$C_6$-haloalkyl, $C_1$-$C_6$-haloalkoxy, nitrile, nitro, —SO$_2$CH$_3$, —SO$_2$CH$_2$CH$_3$, —(C=O)CH$_3$, carboxyl, hydroxyl, —NH$_2$, —CH$_2$NH$_2$, —CH$_2$OH, —CH(OH)CH$_3$, —C(CH$_3$)$_2$OH, —(C=O)NH$_2$, —(C=O)NHCH$_3$, —(C=O)NHCH$_2$CH$_3$, —(C=O)N(CH$_3$)$_2$, —SO$_2$NH$_2$, —SO$_2$NHCH$_3$ or —SO$_2$N(CH$_3$)$_2$, $R^3$ is hydrogen or halogen, $R^4$ is hydrogen, $C_1$-$C_6$-alkyl, $C_3$-$C_6$-cycloalkyl or $C_3$-$C_6$-cycloalkyl-$C_1$-$C_6$-alkyl, which are optionally substituted by up to 6 halogen atoms and are optionally mono- or disubstituted by hydroxyl, $C_1$-$C_6$-alkoxy, $C_1$-$C_6$-haloalkoxy, $R^5$ is hydrogen, $C_1$-$C_6$-alkyl or $C_3$-$C_6$-cycloalkyl, where $C_1$-$C_6$-alkyl and $C_3$-$C_6$-cycloalkyl are optionally substituted by up to 6 halogen atoms and are optionally mono- or disubstituted by hydroxyl, hydroxy-$C_1$-$C_6$-alkyl, $C_1$-$C_6$-alkyl, $C_1$-$C_6$-alkoxy, hydroxy-$C_2$-$C_6$-alkoxy, $C_1$-$C_6$-haloalkoxy, $C_3$-$C_6$-cycloalkyl, aryl, heteroaryl, 3-10-membered heterocycloalkyl, aryl-$C_1$-$C_6$-alkyl, heteroaryl-$C_1$-$C_6$-alkyl, —C(=O)R', —C(=O)NH$_2$, —C(=O)N(H)R', —C(=O)N(R')R", —NH$_2$, —NHR'— N(R')R", —N(H)C(=O)R', —N(R')C(=O)R', —N(H)C(=O)OR', —N(R')C(=O)OR', —NO$_2$, —N(H)S(=O) R', —N(R')S(=O)R', —N(H)S(=O)$_2$R', —N(R') S(=O)$_2$R', —N=S(=O)(R')R", —S(=O)R', —S(=O)$_2$ R', —S(=O)$_2$NH$_2$, —S(=O)$_2$NHR', —S(=O)$_2$N(R')R", —S(=O)(=NR')R", where aryl, heteroaryl, aryl-$C_1$-$C_6$-alkyl and heteroaryl-$C_1$-$C_6$-alkyl are optionally each independently mono- or polysubstituted by $R^6$, and 3-10-membered heterocycloalkyl is optionally independently mono- or polysubstituted by R', or $R^4$ and $R^5$ together with the directly joining nitrogen atom are a 4-7-membered ring which is optionally substituted by one or two substituents from the group consisting of: halogen, nitrile, hydroxyl, $C_1$-$C_6$-alkyl, $C_1$-$C_6$-haloalkyl, $C_2$-$C_6$-alkenyl, $C_2$-$C_6$-alkynyl, $C_3$-$C_{10}$-Cycloalkyl, aryl, heteroaryl, —C(=O)NH$_2$, —C(=O)N(H)R', —C(=O)N(R')R", —C(=O)OH, —C(=O)OR', —NH$_2$, —NHR', —N(R')R", —N(H)C(=O)R', —N(R')C(=O)R', —N(H)S(=O)R', —N(R')S(=O) R', —N(H)S(=O)$_2$R', —N(R')S(=O)$_2$R', —N=S (=O)(R')R", —OH, $C_1$-$C_6$-alkoxy, $C_1$-$C_6$-haloalkoxy, —OC(=O)R', —OC(=O)NH$_2$, —OC(=O)NHR', —OC(=O)N(R')R", —SH, $C_1$-$C_6$-alkyl-S—, —S(=O)R', —S(=O)$_2$R', —S(=O)$_2$NH$_2$, —S(=O)$_2$NHR', —S(=O)$_2$N(R')R", where aryl and heteroaryl are optionally each independently mono- or polysubstituted by $R^6$, and in which 5-, 6- or 7-membered ring one or more methylene groups are optionally replaced by NH, NR', O or S, $R^6$ is halogen, nitrile, $C_1$-$C_6$-alkyl, $C_1$-$C_6$-haloalkyl, $C_2$-$C_6$-alkenyl, $C_2$-$C_6$-alkynyl, $C_3$-$C_{10}$-cycloalkyl, 3-10-membered heterocycloalkyl, aryl, heteroaryl, —C(=O)R', —C(=O)NH$_2$, —C(=O)N(H)R', —C(=O)N(R')R", —C(=O)OR', —NH$_2$, —NHR', —N(R')R", —N(H)C (=O)R', —N(R')C(=O)R', —N(H)C(=O)NH$_2$, —N(H) C(=O)NHR', —N(H)C(=O)N(R')R", —N(R')C(=O) NH$_2$, —N(R')C(=O)NHR', —N(R')C(=O)N(R')R", —N(H)C(=O)OR', —N(R')C(=O)OR', —NO$_2$, —N(H) S(=O)R', —N(R')S(=O)R', —N(H)S(=O)$_2$R', —N(R') S(=O)$_2$R', —N=S(=O)(R')R", —OH, $C_1$-$C_6$-alkoxy, $C_1$-$C_6$-haloalkoxy, —OC(=O)R', —OC(=O)NH$_2$, —OC(=O)NHR', —OC(=O)N(R')R", —SH, $C_1$-$C_6$-alkyl-S—, —S(=O)R', —S(=O)$_2$R', —S(=O)$_2$NH$_2$, —S(=O)$_2$NHR', —S(=O)$_2$N(R')R", —S(=O)(=NR') R"

R' and R" are each independently $C_1$-$C_6$-alkyl, $C_3$-$C_{10}$-Cycloalkyl or $C_1$-$C_6$-haloalkyl, or the stereoisomers, tautomers, N-oxides, hydrates, solvates or salts thereof, or a mixture consisting of the above.

Inventive compounds are the compounds of the formula (I) and the stereoisomers, tautomers, N-oxides, hydrates, salts, solvates and solvates of the salts thereof, and also the compounds encompassed by the formula (I) which are specified hereinafter as working examples, and the stereoisomers, tautomers, N-oxides, hydrates, salts, solvates and solvates of the salts thereof.

Preferred salts in the context of the present invention are physiologically acceptable salts of the inventive compounds. Also encompassed are salts which are not themselves suitable for pharmaceutical applications but can be used, for example, for isolation or purification of the inventive compounds.

Physiologically acceptable salts of the inventive compounds include acid addition salts of mineral acids, carboxylic acids and sulphonic acids, for example salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, formic acid, acetic acid, trifluoroacetic acid, propionic acid, lactic acid, tartaric acid, malic acid, citric acid, fumaric acid, maleic acid and benzoic acid.

Physiologically acceptable salts of the inventive compounds also include salts of conventional bases, by way of example and with preference alkali metal salts (e.g. sodium and potassium salts), alkaline earth metal salts (e.g. calcium and magnesium salts) and ammonium salts derived from ammonia or organic amines having 1 to 16 carbon atoms, by way of example and with preference ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

In the context of the invention, solvates refer to those forms of the inventive compounds which, in the solid or liquid state, form a complex by coordination with solvent molecules. Hydrates are a specific form of the solvates in which the coordination is with water. Preferred solvates in the context of the present invention are hydrates.

Depending on their structure, the inventive compounds may exist in different stereoisomeric forms, i.e. in the form of configurational isomers or if appropriate also as conformational isomers (enantiomers and/or diastereomers, including those in the case of atropisomers). The present invention therefore encompasses the enantiomers and diastereomers and the respective mixtures thereof. The stereoisomerically homogeneous constituents can be isolated from such mixtures of enantiomers and/or diastereomers in a known manner; chromatography processes are preferably used for this purpose, especially HPLC chromatography on an achiral or chiral phase.

Where the inventive compounds can occur in tautomeric forms, the present invention encompasses all the tautomeric forms.

The present invention also encompasses all suitable isotopic variants of the inventive compounds. An isotopic variant of an inventive compound is understood here to mean a compound in which at least one atom within the inventive compound has been exchanged for another atom of the same atomic number, but with a different atomic mass from the atomic mass which usually or predominantly occurs in nature. Examples of isotopes which can be incorporated into an inventive compound are those of hydrogen, carbon, nitrogen, oxygen, phosphorus, sulphur, fluorine, chlorine, bromine and iodine, such as $^2$H (deuterium), $^3$H (tritium), $^{13}$C, $^{14}$C, $^{15}$N, $^{17}$O, $^{18}$O, $^{32}$P, $^{33}$P, $^{33}$S, $^{34}$S, $^{35}$S, $^{36}$S, $^{18}$F, $^{36}$Cl, $^{82}$Br, $^{123}$I, $^{124}$I, $^{129}$I and $^{131}$I. Particular isotopic variants of an inventive compound, especially those in which one or more radioactive isotopes have been incorporated, may be beneficial, for example, for the examination of the mechanism of action or of the active ingredient distribution in the body; due to comparatively easy preparability and detectability, especially compounds labelled with $^3$H or $^{14}$C isotopes are suitable for this purpose. In addition, the incorporation of isotopes, for example of deuterium, can lead to particular therapeutic benefits as a consequence of greater metabolic stability of the compound, for example an extension of the half-life in the body or a reduction in the active dose required; such modifications of the inventive compounds may therefore in some cases also constitute a preferred embodiment of the present invention. Isotopic variants of the inventive compounds can be prepared by the processes known to those skilled in the art, for example by the methods described below and the instructions reproduced in the working examples, by using corresponding isotopic modifications of the particular reagents and/or starting compounds therein.

Moreover, the present invention also encompasses prodrugs of the inventive compounds. The term "prodrugs" here denotes compounds which may themselves be biologically active or inactive, but are converted (for example metabolically or hydrolytically) to inventive compounds during their residence time in the body.

In the context of the present invention, unless specified otherwise, the substituents are each defined as follows:

Alkyl in the context of the invention is a linear or branched alkyl radical having the number of carbon atoms specified in each case. Examples include: methyl, ethyl, n-propyl, isopropyl, n-butyl, isobutyl, 1-methylpropyl, tert-butyl, n-pentyl, neopentyl, 1-ethylpropyl, 1-methylbutyl, 2-methylbutyl, 3-methylbutyl, n-hexyl, 1-methylpentyl, 2-methylpentyl, 3-methylpentyl, 4-methylpentyl, 1-ethylbutyl and 2-ethylbutyl. Preference is given to: methyl, ethyl, n-propyl, isopropyl, n-butyl, 2-methylbutyl and neopentyl.

Alkenyl in the context of the invention is a linear or branched alkenyl radical having 2 to 6 carbon atoms and one or two double bonds. Preference is given to a straight-chain or branched alkenyl radical having 2 to 4 carbon atoms and one double bond. Examples include: vinyl, allyl, isopropenyl and n-but-2-en-1-yl.

Alkynyl in the context of the invention is a linear or branched alkynyl radical having 2 to 4 carbon atoms and one triple bond. Examples include: ethynyl, n-prop-1-yn-1-yl, n-prop-2-yn-1-yl, n-but-2-yn-1-yl and n-but-3-yn-1-yl.

Cycloalkyl in the context of the invention is a monocyclic saturated alkyl radical having the number of carbon atoms specified in each case. Examples include: cyclopropyl, cyclobutyl, cyclopentyl and cyclohexyl. Preference is given to cyclopentyl.

Hydroxy-$C_1$-$C_6$-alkyl in the context of the invention is a linear or branched alkyl radical having 1 to 6 carbon atoms which bears a hydroxyl group as a substituent in the chain or in a terminal position. Examples include: hydroxymethyl, 1-hydroxyethyl, 2-hydroxyethyl, 1-hydroxy-1-methylethyl, 1,1-dimethyl-2-hydroxyethyl, 1-hydroxypropyl, 2-hydroxypropyl, 3-hydroxypropyl, 1-hydroxy-2-methylpropyl, 2-hydroxy-1-methylpropyl, 2-hydroxy-2-methylpropyl, 1-hydroxybutyl, 2-hydroxybutyl, 3-hydroxybutyl and 4-hydroxybutyl. Preference is given to: hydroxymethyl, 2-hydroxyethyl and 3-hydroxypropyl.

Alkoxy in the context of the invention is a linear or branched alkoxy radical having 1 to 6 carbon atoms. Examples include: methoxy, ethoxy, n-propoxy, isopropoxy, 1-methylpropoxy, n-butoxy, isobutoxy, tert-butoxy, n-pentoxy, isopentoxy, 1-ethylpropoxy, 1-methylbutoxy, 2-methylbutoxy, 3-methylbutoxy and n-hexoxy. Preference is given to a linear or branched alkoxy radical having 1 to 4 carbon atoms. Examples include: methoxy, ethoxy, n-propoxy, 1-methylpropoxy, n-butoxy and isobutoxy. Preference is given to methoxy.

Hydroxy-$C_2$-$C_6$-alkoxy in the context of the invention is a linear or branched alkoxy radical having 2 to 6 carbon atoms which bears a hydroxyl group as a substituent in the chain or in a terminal position. Examples include: 2-hydroxyethoxy and 2-hydroxypropoxy. Preference is given to 2-hydroxyethoxy.

Cycloalkoxy in the context of the invention is a monocyclic saturated carbocycle which has 3 to 7 carbon atoms and is bonded via an oxygen atom. Examples include: cyclopropyloxy, cyclobutyloxy, cyclopentyloxy, cyclohexyloxy and cycloheptyloxy.

Heterocycloalkyl, heterocyclyl or heterocycle in the context of the invention is a saturated heterocycle which has a total of 3 to 10 ring atoms and contains one or two ring heteroatoms from the group consisting of N, O, S, SO and/or $SO_2$. Examples include: azetidinyl, oxetanyl, pyrrolidinyl, pyrazolidinyl, tetrahydrofuranyl, piperidinyl, piperazinyl, tetrahydropyranyl, morpholinyl, thiomorpholinyl, dioxidothiomorpholinyl, dihydroindolyl and dihydroisoindolyl. Preference is given to: azetidinyl, oxetanyl, pyrrolidinyl, piperidinyl, piperazinyl and morpholinyl.

Aryl in the context of the invention is a mono- to tricyclic aromatic, carbocyclic radical having generally 6 to 14 carbon atoms. Examples include: phenyl, naphthyl and phenanthrenyl. Preference is given to phenyl.

Heteroaryl in the context of the invention is a monocyclic aromatic heterocycle (heteroaromatic) which has a total of 5 or 6 ring atoms, contains up to four identical or different ring heteroatoms from the group of N, O and/or S and is attached via a ring carbon atom or optionally via a ring nitrogen atom. Examples include: furyl, pyrrolyl, thienyl, pyrazolyl, imidazolyl, thiazolyl, oxazolyl, isoxazolyl, isothiazolyl, triazolyl, tetrazolyl, oxadiazolyl, thiadiazolyl, oxathiadiazolyl, pyridyl, pyrimidinyl, pyridazinyl, pyrazinyl and triazinyl. Preference is given to: pyrazolyl, 1H-tetrazol-5-yl, oxadiazolyl, thiadiazolyl, pyridyl and pyrimidinyl.

The abovementioned monocyclic aromatic heterocycle is optionally substituted by hydroxyl or —SH, where heteroaryl represents all the possible tautomeric forms. Examples include: 5-oxo-4,5-dihydro-1,2,4-thiadiazol-3-yl, 5-oxo-4,5-dihydro-1H-1,2,4-triazol-3-yl, 5-thioxo-4,5-dihydro-1,2,4-oxadiazol-3-yl, 5-oxo-4,5-dihydro-1,2,4-oxadiazol-3-yl, 2-oxido-3H-1,2,3,5-oxathiadiazol-4-yl, 3-oxo-2,3-dihydro-1,2,4-oxadiazol-5-yl.

Aryl-$C_1$-$C_6$-alkyl in the context of the invention is a mono- to tricyclic aromatic, carbocyclic radical having generally 6 to 14 carbon atoms which is bonded via a linear or branched alkyl radical having the number of carbon atoms specified in each case.

Heteroaryl-$C_1$-$C_6$-alkyl in the context of the invention is a monocyclic aromatic heterocycle (heteroaromatic) having a total of 5 or 6 ring atoms which contains up to three identical or different ring heteroatoms from the group of N, O and/or S and is bonded via a ring carbon atom or, if present, via a ring nitrogen atom and which is bonded via a linear or branched alkyl radical having the number of carbon atoms specified in each case.

$C_3$-$C_6$-Cycloalkyl-$C_1$-$C_6$-alkyl in the context of the invention is a monocyclic saturated alkyl radical having the number of carbon atoms specified in each case, which is bonded via a linear or branched alkyl radical having the number of carbon atoms specified in each case.

Halogen in the context of the invention is fluorine, chlorine, bromine and iodine. Preference is given to fluorine and chlorine.

Hydroxyl in the context of the invention is a hydroxyl group.

When radicals in the inventive compounds are substituted, the radicals may be mono- or polysubstituted, unless specified otherwise. In the context of the present invention, all radicals which occur more than once are defined independently of one another. Substitution by one, two or three identical or different substituents is preferred.

In the context of the present invention, the term "treatment" or "treating" includes inhibition, retardation, checking, alleviating, attenuating, restricting, reducing, suppressing, repelling or healing of a disease, a condition, a disorder, an injury or a health problem, or the development, the course or the progression of such states and/or the symptoms of such states. The term "therapy" is understood here to be synonymous with the term "treatment".

The terms "prevention", "prophylaxis" or "preclusion" are used synonymously in the context of the present invention and refer to the avoidance or reduction of the risk of contracting, experiencing, suffering from or having a disease, a condition, a disorder, an injury or a health problem, or a development or advancement of such states and/or the symptoms of such states.

The treatment or prevention of a disease, a condition, a disorder, an injury or a health problem may be partial or complete.

The invention likewise provides compounds of the formula (I)
where
X is carbon substituted by hydrogen,
Y is carbon or nitrogen, where the carbon may be substituted by $R^2$,
$R^2$ is hydrogen, fluorine, chlorine, nitrile, methoxy, ethoxy, trifluoromethoxy, methyl, ethyl, trifluoromethyl, —(C═O)$CH_3$,
$R^3$ is hydrogen or fluorine,
$R^4$ is hydrogen, methyl, ethyl, isopropyl, propyl, butyl, cyclopropyl or 2,2,2-trifluoroethyl,
$R^5$ is hydrogen, methyl, ethyl, propyl, 2,2,2-trifluoroethyl, 3,3,3-trifluoropropyl, 2-fluoroethyl, 2-sulphamoylethyl, 3-sulphamoylpropyl, (1S,2R)-2-hydroxycyclopentyl, 3-hydroxy-2,2-dimethylpropyl, (1S,2S)-2-hydroxycyclopentyl, (3R)-4-hydroxy-3-methylbutyl, 1-(hydroxymethyl)cyclopentyl, (2S)-1-hydroxybutan-2-yl, (2R)-1-hydroxy-3-methylbutan-2-yl, 3-hydroxybutan-2-yl, 2-hydroxyethyl, 3,3,3-trifluoro-2-hydroxypropyl, 2-(1H-tetrazol-5-yl)ethyl, 1H-tetrazol-5-ylmethyl, 2-(methylsulphamoyl)ethyl, 3-amino-3-oxopropyl, 3-(methylamino)-3-oxopropyl, 2-methyl-2-[(methylsulphonyl)amino]propyl, (2S)-2,3-dihydroxypropyl, 3-hydroxypropyl, 4-hydroxybutyl, (2RS)-2,3-dihydroxypropyl, (2R)-2,3-dihydroxypropyl, 2,3-dihydroxybutyl, 2-(methylsulphinyl)ethyl, 3-(methylsulphinyl)propyl, 2-(methylsulphonyl)ethyl, 3-(methylsulphonyl)propyl, 2-(S-methylsulphonimidoyl)ethyl, (2R)-2-hydroxypropyl, (2S)-1-hydroxypropan-2-yl, 2-methoxyethyl, 3-methoxypropyl, 2-(isopropylsulphonyl)ethyl, (3-methyloxetan-3-yl)methyl, (2S)-2-hydroxypropyl, 2-(2-hydroxyethoxy)ethyl,
or
$R^4$ and $R^5$ together with the directly joining nitrogen atom are piperidinyl, pyrrolidinyl, morpholinyl, N-methylpiperazinyl, 1-oxidothiomorpholinyl, 1,1-dioxidothiomorpholin-4-yl, 4-hydroxypiperidinyl, 4-(trifluoromethyl)piperidin-4-yl, (3R)-3-hydroxypiperidinyl, (2S)-2-(1H-tetrazol-5-yl)pyrrolidinyl, N-methyl-L-prolinamidyl and L-prolinamidyl,
or the stereoisomers, tautomers, N-oxides, hydrates, solvates or salts thereof, or a mixture consisting of the above.

The invention also provides compounds of the formula (I)
where
X is carbon substituted by hydrogen,
Y is carbon or nitrogen, where the carbon may be substituted by $R^2$,
$R^2$ is hydrogen, fluorine, chlorine, methyl, nitrile, methoxy, trifluoromethyl,
$R^3$ is hydrogen or fluorine,
$R^4$ is hydrogen, methyl, ethyl, isopropyl, propyl or cyclopropyl,
$R^5$ is hydrogen, methyl, ethyl, 2-sulphamoylethyl, 3-sulphamoylpropyl, (1S,2R)-2-hydroxycyclopentyl, 3-hydroxy-2,2-dimethylpropyl, (1S,2S)-2-hydroxycyclopentyl, (3R)-4-hydroxy-3-methylbutyl, 1-(hydroxymethyl)

cyclopentyl, (2S)-1-hydroxybutan-2-yl, (2R)-1-hydroxy-3-methylbutan-2-yl, 3-hydroxybutan-2-yl, 2-hydroxyethyl, 3,3,3-trifluoro-2-hydroxypropyl, 2-(1H-tetrazol-5-yl)ethyl, 1H-tetrazol-5-ylmethyl, 2-(methylsulphamoyl)ethyl, 3-amino-3-oxopropyl, 3-(methylamino)-3-oxopropyl, 2-methyl-2-[(methylsulphonyl)amino]propyl, (2S)-2,3-dihydroxypropyl, 3-hydroxypropyl, (2RS)-2,3-dihydroxypropyl, (2R)-2,3-dihydroxypropyl, 2-(methylsulphinyl)ethyl, (2R)-2-hydroxypropyl, (2S)-1-hydroxypropan-2-yl, 2-methoxyethyl, 2-(isopropylsulphonyl)ethyl, (3-methyloxetan-3-yl)methyl, (2S)-2-hydroxypropyl or 2-(2-hydroxyethoxy)ethyl,
or $R^4$ and $R^5$ together with the directly joining nitrogen atom are piperidinyl, pyrrolidinyl, morpholinyl, 4-hydroxypiperidinyl, (3R)-3-hydroxypiperidinyl, (2S)-2-(1H-tetrazol-5-yl)pyrrolidinyl, N-methyl-L-prolinamidyl or L-prolinamidyl or the stereoisomers, tautomers, N-oxides, hydrates, solvates or salts thereof, or a mixture consisting of the above.

The invention additionally provides compounds of the formula (I)
where
X is carbon substituted by hydrogen,
Y is carbon or nitrogen, where the carbon may be substituted by $R^2$,
$R^2$ is hydrogen, fluorine, nitrile, methoxy or trifluoromethyl,
$R^3$ is hydrogen or fluorine,
$R^4$ is hydrogen, methyl, ethyl or isopropyl,
$R^5$ is hydrogen, ethyl, 2-sulphamoylethyl, (1S,2R)-2-hydroxycyclopentyl, 3-hydroxy-2,2-dimethylpropyl, (1S,2S)-2-hydroxycyclopentyl, (3R)-4-hydroxy-3-methylbutyl, 1-(hydroxymethyl)cyclopentyl, (2S)-1-hydroxybutan-2-yl, (2R)-1-hydroxy-3-methylbutan-2-yl, 3-hydroxybutan-2-yl, 2-hydroxyethyl, 3,3,3-trifluoro-2-hydroxypropyl, 2-(1H-tetrazol-5-yl)ethyl, 1H-tetrazol-5-ylmethyl, 2-(methylsulphamoyl)ethyl, 3-amino-3-oxopropyl, 3-(methylamino)-3-oxopropyl, 2-methyl-2-[(methylsulphonyl)amino]propyl, (2S)-2,3-dihydroxypropyl, 3-hydroxypropyl, (2RS)-2,3-dihydroxypropyl, (2R)-2,3-dihydroxypropyl, 2-(methylsulphinyl)ethyl, (2R)-2-hydroxypropyl, (2S)-1-hydroxypropan-2-yl, 2-methoxyethyl, 2-(isopropylsulphonyl)ethyl, (3-methyloxetan-3-yl)methyl, (2S)-2-hydroxypropyl or 2-(2-hydroxyethoxy)ethyl,
or $R^4$ and $R^5$ together with the directly joining nitrogen atom are
4-hydroxypiperidinyl, (3R)-3-hydroxypiperidinyl, (2S)-2-(1H-tetrazol-5-yl)pyrrolidinyl, N-methyl-L-prolinamidyl or L-prolinamidyl or the stereoisomers, tautomers, N-oxides, hydrates, solvates or salts thereof, or a mixture consisting of the above.

The invention further provides the compounds:
1. 17-(3-pyridyl)oestra-1,3,5(10),16-tetraene-3-carboxamide
2. 17-(5-methoxypyridin-3-yl)oestra-1,3,5(10),16-tetraene-3-carboxamide
3. 17-[5-(trifluoromethyl)pyridin-3-yl]oestra-1,3,5(10),16-tetraene-3-carboxamide
4. 17-(5-fluoropyridin-3-yl)oestra-1,3,5(10),16-tetraene-3-carboxamide
5. 17-(pyrimidin-5-yl)oestra-1,3,5(10),16-tetraene-3-carboxamide
6. 17-(5-cyanopyridin-3-yl)oestra-1,3,5(10),16-tetraene-3-carboxamide
7. 11β-fluoro-17-(5-fluoropyridin-3-yl)oestra-1,3,5(10),16-tetraene-3-carboxamide
8. 11β-fluoro-17-(5-fluoropyridin-3-yl)-N-(2-sulphamoylethyl)oestra-1,3,5(10),16-tetraene-3-carboxamide
9. 17-(5-fluoropyridin-3-yl)-N-[(1S,2R)-2-hydroxycyclopentyl]oestra-1,3,5(10),16-tetraene-3-carboxamide
10. 17-(5-fluoropyridin-3-yl)-N-[2-(hydroxymethyl)-2-methylpropyl]oestra-1,3,5(10),16-tetraene-3-carboxamide
11. 17-(5-fluoropyridin-3-yl)-N-[(1S,2S)-2-hydroxycyclopentyl]oestra-1,3,5(10),16-tetraene-3-carboxamide
12. 17-(5-fluoropyridin-3-yl)-N—[(R)-3-(hydroxymethyl)butyl]oestra-1,3,5(10),16-tetraene-3-carboxamide
13. 17-(5-fluoropyridin-3-yl)-N-[1-(hydroxymethyl)cyclopentyl]oestra-1,3,5(10),16-tetraene-3-carboxamide
14. 17-(5-fluoropyridin-3-yl)oestra-1,3,5(10),16-tetraen-3-yl 4-hydroxypiperidin-1-yl ketone
15. 17-(5-fluoropyridin-3-yl)-N—[(S)-1-(hydroxymethyl)propyl]oestra-1,3,5(10),16-tetraene-3-carboxamide
16. 17-(5-fluoropyridin-3-yl)-N—[(R)-1-(hydroxymethyl)-2-methylpropyl]oestra-1,3,5(10),16-tetraene-3-carboxamide
17. 17-(5-fluoropyridin-3-yl)oestra-1,3,5(10),16-tetraen-3-yl (R)-3-hydroxypiperidin-1-yl ketone
18. rel-17-(5-fluoropyridin-3-yl)-N-[(1R,2R)-2-hydroxy-1-methylpropyl]oestra-1,3,5(10),16-tetraene-3-carboxamide
19. 17-(5-fluoropyridin-3-yl)-N-(2-hydroxyethyl)-N-isopropyloestra-1,3,5(10),16-tetraene-3-carboxamide
20. 17-(5-fluoropyridin-3-yl)-N—[(RS)-3,3,3-trifluoro-2-hydroxypropyl]oestra-1,3,5(10),16-tetraene-3-carboxamide
21. 17-(5-fluoropyridin-3-yl)-N-[2-(1H-tetrazol-5-yl)ethyl]oestra-1,3,5(10),16-tetraene-3-carboxamide
22. 17-(5-fluoropyridin-3-yl)-N-(1H-tetrazol-5-ylmethyl)oestra-1,3,5(10),16-tetraene-3-carboxamide
23. 17-(3-pyridyl)-N-(2-sulphamoylethyl)oestra-1,3,5(10),16-tetraene-3-carboxamide
24. N-(2-sulphamoylethyl)-17-[5-(trifluoromethyl)pyridin-3-yl]oestra-1,3,5(10),16-tetraene-3-carboxamide
25. N-[2-(N-methylsulphamoyl)ethyl]-17-[5-(trifluoromethyl)pyridin-3-yl]oestra-1,3,5(10),16-tetraene-3-carboxamide
26. N-(3-amino-3-oxopropyl)-17-(5-fluoropyridin-3-yl)oestra-1,3,5(10),16-tetraene-3-carboxamide
27. 17-(5-fluoropyridin-3-yl)-N-[3-(methylamino)-3-oxopropyl]oestra-1,3,5(10),16-tetraene-3-carboxamide
28. 17-(5-fluoropyridin-3-yl)oestra-1,3,5(10),16-tetraen-3-yl (S)-2-(1H-tetrazol-5-yl)pyrrolidin-1-yl ketone
29. 1-{[17-(5-fluoropyridin-3-yl)oestra-1,3,5(10),16-tetraen-3-yl]carbonyl}-N-methyl-L-prolinamide
30. 1-{[17-(5-fluoropyridin-3-yl)oestra-1,3,5(10),16-tetraen-3-yl]carbonyl}-L-prolinamide
31. 17-(5-fluoropyridin-3-yl)-N-{2-methyl-2-[(methylsulphonyl)amino]propyl}oestra-1,3,5(10),16-tetraene-3-carboxamide
32. N-ethyl-17-(5-fluoropyridin-3-yl)-N-(2-hydroxyethyl)oestra-1,3,5(10),16-tetraene-3-carboxamide
33. N—[(S)-2,3-dihydroxypropyl]-17-(5-fluoropyridin-3-yl)oestra-1,3,5(10),16-tetraene-3-carboxamide
34. 17-(5-fluoropyridin-3-yl)-N-(3-hydroxypropyl)-N-methyloestra-1,3,5(10),16-tetraene-3-carboxamide
35. N—[(RS)-2,3-dihydroxypropyl]-17-(5-fluoropyridin-3-yl)-N-methyloestra-1,3,5(10),16-tetraene-3-carboxamide
36. N—[(R)-2,3-dihydroxypropyl]-17-(5-fluoropyridin-3-yl)oestra-1,3,5(10),16-tetraene-3-carboxamide 37. 17-(5-fluoropyridin-3-yl)-N-[2-(methylsulphinyl)ethyl] oestra-1,3,5(10),16-tetraene-3-carboxamide
38. 17-(5-fluoropyridin-3-yl)-N—[(R)-2-hydroxypropyl] oestra-1,3,5(10),16-tetraene-3-carboxamide
39. N-ethyl-17-(5-fluoropyridin-3-yl)oestra-1,3,5(10),16-tetraene-3-carboxamide
40. 17-(5-fluoropyridin-3-yl)-N—[(S)-1-(hydroxymethyl) ethyl]oestra-1,3,5(10),16-tetraene-3-carboxamide
41. 17-(5-fluoropyridin-3-yl)-N-(2-methoxyethyl)oestra-1, 3,5(10),16-tetraene-3-carboxamide
42. 17-(5-fluoropyridin-3-yl)-N-[2-(isopropylsulphonyl) ethyl]oestra-1,3,5(10),16-tetraene-3-carboxamide
43. 17-(5-fluoropyridin-3-yl)-N-[(3-methyloxetan-3-yl) methyl]oestra-1,3,5(10),16-tetraene-3-carboxamide
44. 17-(5-fluoropyridin-3-yl)-N-(2-hydroxyethyl)-N-methyloestra-1,3,5(10),16-tetraene-3-carboxamide
45. 17-(5-fluoropyridin-3-yl)-N—[(S)-2-hydroxypropyl] oestra-1,3,5(10),16-tetraene-3-carboxamide
46. 17-(5-fluoropyridin-3-yl)-N-[2-(2-hydroxyethoxy)ethyl] oestra-1,3,5(10),16-tetraene-3-carboxamide
47. 17-(pyrimidin-5-yl)-N-(2-sulphamoylethyl)oestra-1,3,5 (10),16-tetraene-3-carboxamide and the stereoisomers, tautomers, N-oxides, hydrates, solvates or salts thereof, or a mixture consisting of the above.

The inventive compounds are substances based on an oestra-1,3,5(10),16-tetraene skeleton substituted by an aromatic heterocycle at position 17.

The inventive compounds are potent inhibitors of AKR1C3. In contrast to abiraterone, a steroidal Cyp17A1 (lyase) inhibitor used in clinical situations, which has a pyridine ring, Cyp17A1 is not inhibited by the inventive compounds up to a substance concentration of 20 µM. The compounds claimed show inhibition of AKR1C3 in vitro ($IC_{50}$ values <500 nM) and predominantly even $IC_{50}$ values <100 nM (see Tables 1 and 2).

Furthermore, the enzymes AKR1C1, AKR1C2 and AKR1C4, which are related to AKR1C3, are not inhibited by the inventive compounds.

The novel AKR1C3 inhibitors claimed here show improved water solubility compared to the known AKR1C3 inhibitor EM-1404. This improves the formulability of the inventive compounds in aqueous administration media.

The present invention provides compounds of the formula (I) for treatment and/or prophylaxis of diseases.

The inventive compounds have an unforeseeable, valuable spectrum of pharmacological and pharmacokinetic activity. They are therefore suitable for use as medicaments for treatment and/or prophylaxis of disorders in humans and animals. The term "treatment" in the context of the present invention includes prophylaxis. The pharmaceutical efficacy of the inventive compounds can be explained by the action thereof as an AKR1C3 inhibitor. As shown in Tables 1 (Example 48, inhibition of AKR1C3 in a biochemical assay) and 2 (Example 49, inhibition of AKR1C3 in a cell-based system), the inventive compounds are potent inhibitors of the AKR1C3 enzyme, as a result of which they are capable of blocking local oestradiol production in endometrial lesions. For treatment of endometriosis, a treatment low in side effects is especially preferred, which is why selectivity of the AKR1C3 inhibitors over the steroid-metabolizing enzyme CYP17A1 (lyase) is important. The data for selected inventive compounds in Table 3 (Example 50, inhibition of human CYP17) show that, up to a very high concentration of 20 µM, no inhibition of CYP17A1 has occurred, and so the compounds are selective with respect to CYP17A1. As well as selectivity over CYP17A1, selectivity over other enzymes of the AKR1C family is important in order to obtain a favourable profile of side effects, since the enzymes AKR1C1, -2 and -4 are likewise involved in steroid synthesis. Inhibition of these enzymes would eliminate the advantage of the selective local inhibition of oestradiol synthesis and could lead to systemic changes in various steroid hormones. Table 4 (Example 51, inhibition of AKR1C1, -2 and -4) shows, for inventive compound 1, that there is no inhibition of these enzymes. Phenolphthalein, which was used as a positive control, in contrast, shows inhibition of the enzymes. The inventive compounds are therefore particularly suitable for treatment and/or prophylaxis of endometriosis.

In addition, the inventive compounds are suitable for treatment and/or prophylaxis of uterine leiomyoma, of uterine bleeding disorders, of dysmenorrhoea, of prostate carcinoma, of prostate hyperplasia, of acne, of seborrhoea, of hair loss, of premature sexual maturity, of polycystic ovary syndrome, of breast cancer, of lung cancer, of endometrial carcinoma, of renal cell carcinoma, of bladder carcinoma, of non-Hodgkins lymphoma, of chronic obstructive pulmonary disease (COPD), of obesity, or of inflammation-related pain.

The present invention further provides for the use of the inventive compounds for production of a medicament for treatment and/or prophylaxis of disorders, especially of the aforementioned disorders.

The present invention further provides a method for treatment and/or prophylaxis of disorders, especially the aforementioned disorders, using an effective amount of the inventive compounds.

The present invention further provides for the use of the inventive compounds for treatment and/or prophylaxis of disorders, especially of the aforementioned disorders.

The present invention further provides the inventive compounds for use in a method for treatment and/or prophylaxis of the aforementioned disorders.

The present invention further provides medicaments comprising at least one inventive compound and at least one or more than one further active ingredient, especially for treatment and/or prophylaxis of the aforementioned disorders. Preferred examples of suitable combination active ingredients include: selective oestrogen receptor modulators (SERMs), oestrogen receptor (ER) antagonists, aromatase inhibitors, 17β-HSD1 inhibitors, steroid sulphatase (STS) inhibitors, GnRH agonists and antagonists, kisspeptin receptor (KISSR) antagonists, selective androgen receptor modulators (SARMs), androgens, 5α-reductase inhibitors, selective progesterone receptor modulators (SPRMs), gestagens, antigestagens, oral contraceptives, inhibitors of mitogen-activated protein (MAP) kinases and inhibitors of the MAP kinases (Mkk3/6, Mek1/2, Erk1/2), inhibitors of the protein kinases B (PKBα/β/γ; Akt1/2/3), inhibitors of the phosphoinositide 3-kinases (PI3K), inhibitors of cyclin-dependent kinase (CDK1/2), inhibitors of the hypoxia-induced signalling pathway (HIF1alpha inhibitors, activators of prolylhydroxylases), histone deacetylase (HDAC) inhibitors, prostaglandin F receptor (FP) (PTGFR) antagonists, and non-steroidal inflammation inhibitors (NSAIDs).

For example, the compounds of the present invention can be combined with known antihyperproliferative, cytostatic or cytotoxic substances for treatment of cancers. In addition, the inventive compounds can also be used in combination with radiotherapy and/or surgical intervention.

Examples of suitable combination active ingredients include:
131I-chTNT, abarelix, abiraterone, aclarubicin, aldesleukin, alemtuzumab, alitretinoin, altretamine, aminoglutethimide, amrubicin, amsacrine, anastrozole, arglabin, arsentrioxidas, asparaginase, azacitidine, basiliximab, RDEA 119, belotecan, bendamustine, bevacizumab, bexarotene, bicalutamide, bisantrene, bleomycin, bortezomib, buserelin, busulfan, cabazitaxel, calcium folinate, calcium levofolinate, capecitabine, carboplatin, carmofur, carmustine, catumaxomab, celecoxib, celmoleukin, cetuximab, chlorambucil, chlormadinone, chlormethine, cisplatin, cladribine, clodronic acid, clofarabine, crisantaspase, cyclophosphamide, cyproterone, cytarabine, dacarbazine, dactinomycin, darbepoetin alfa, dasatinib, daunorubicin, decitabine, degarelix, denileukin diftitox, denosumab, deslorelin, dibrospidium chloride, docetaxel, doxifluridine, doxorubicin, doxorubicin+oestrone, eculizumab, edrecolomab, elliptinium acetate, eltrombopag, endostatin, enocitabine, epirubicin, epitiostanol, epoetin alfa, epoetin beta, eptaplatin, eribulin, erlotinib, oestradiol, oestramustine, etoposide, everolimus, exemestane, fadrozole, filgrastim, fludarabine, fluorouracil, flutamide, formestane, fotemustine, fulvoestrant, gallium nitrate, ganirelix, gefitinib, gemcitabine, gemtuzumab, glutoxim, goserelin, histamine dihydrochloride, histrelin, hydroxycarbamide, I-125 pellets, ibandronic acid, ibritumomab tiuxetan, idarubicin, ifosfamide, imatinib, imiquimod, improsulfan, interferon alfa, interferon beta, interferon gamma, ipilimumab, irinotecan, ixabepilone, lanreotide, lapatinib, lenalidomide, lenograstim, lentinan, letrozole, leuprorelin, levamisole, lisuride, lobaplatin, lomustine, lonidamine, masoprocol, medroxyprogesterone, megestrol, melphalan, mepitiostan, mercaptopurine, methotrexate, methoxsalen, methyl aminolevulinate, methyltestosterone, mifamurtide, miltefosine, miriplatin, mitobronitol, mitoguazone, mitolactol, mitomycin, mitotane, mitoxantrone, nedaplatin, nelarabine, nilotinib, nilutamide, nimotuzumab, nimustine, nitracrine, ofatumumab, omeprazole, oprelvekin, oxaliplatin, p53 gene therapy, paclitaxel, palifermin, palladium-103 pellets, pamidronic acid, panitumumab, pazopanib, pegaspargase, pEG-epoetin beta (methoxy PEG-epoetin beta), pegfilgrastim, peginterferon alfa-2b, pemetrexed, pentazocine, pentostatin, peplomycin, perfosfamid, picibanil, pirarubicin, plerixafor, plicamycin, poliglusam, polyoestradiol phosphate, polysaccharide-K, porfimer sodium, pralatrexate, prednimustine, procarbazine, quinagolide, radium-223 chloride, raloxifen, raltitrexed, ranimustine, razoxane, regorafenib, risedronic acid, rituximab, romidepsin, romiplostim, sargramostim, sipuleucel-T, sizofiran, sobuzoxan, sodium glycididazole, sorafenib, streptozocin, sunitinib, talaporfin, tamibarotene, tamoxifen, tasonermin, teceleukin, tegafur, tegafur+gimeracil+oteracil, temoporfin, temozolomide, temsirolimus, teniposide, testosterone, tetrofosmin, thalidomide, thiotepa, thymalfasin, tioguanine, tocilizumab, topotecan, toremifene, tositumomab, trabectedin, trastuzumab, treosulfan, tretinoin, trilostane, triptorelin, trofosfamide, tryptophan, ubenimex, valrubicin, vandetanib, vapreotide, vemurafenib, vinblastine, vincristine, vindesine, vinflunine, vinorelbine, vorinostat, vorozole, yttrium-90 glass microspheres, zinostatin, zinostatin stimalamer, zoledronic acid, zorubicin.

The present invention preferably relates to medicaments comprising at least one inventive compound and one or more of the following active ingredients, especially for treatment and/or prophylaxis of androgen receptor-dependent proliferative disorders:
LHRH (luteinizing hormone-releasing hormone) agonists,
LHRH (luteinizing hormone-releasing hormone) antagonists,
C(17,20)-lyase inhibitors,
type I 5-α-reductase inhibitors,
type II 5-α-reductase inhibitors,
mixed type I/II 5-α-reductase inhibitors,
α-radiation-emitting radiopharmaceuticals for treatment of bone metastases, for example radium-223 chloride,
cytostatics,
VEGF (Vascular Endothelial Growth Factor) kinase inhibitors,
antigestagens,
antioestrogens,
EGF antibodies,
oestrogens or
other androgen receptor antagonists,
poly(ADP-ribose) polymerase I inhibitors, or
bi-specific T-cell engagers (BiTE) coupled to a cell surface protein, for example prostate-specific membrane antigen (PSMA).

The invention also relates to pharmaceutical formulations comprising at least one compound of the general formula I (or physiologically acceptable addition salts with organic and inorganic acids) and to the use of these compounds for production of medicaments, especially for the aforementioned indications.

The compounds can be used for the aforementioned indications after either oral or parenteral administration.

The inventive compounds can act systemically and/or locally. For this purpose, they can be administered in a suitable manner, for example by the oral, parenteral, pulmonal, nasal, sublingual, lingual, buccal, rectal, dermal, transdermal, conjunctival, otic route, or as an implant or stent.

The inventive compounds can be administered in administration forms suitable for these administration routes.

Suitable administration forms for oral administration are those which release the inventive compounds in a rapid and/or modified manner, work according to the prior art and contain the inventive compounds in crystalline and/or amorphous and/or dissolved form, for example tablets (uncoated or coated tablets, for example with enteric or retarded-dissolution or insoluble coatings which control the release of the inventive compound), tablets or films/wafers which disintegrate rapidly in the oral cavity, films/lyophilizates, capsules (for example hard or soft gelatin capsules), sugar-coated tablets, granules, pellets, powders, emulsions, suspensions, aerosols or solutions.

Parenteral administration can be accomplished with avoidance of an absorption step (for example by an intravenous, intraarterial, intracardial, intraspinal or intralumbar route) or with inclusion of an absorption (for example by an intramuscular, subcutaneous, intracutaneous, percutaneous or intraperitoneal route). Suitable administration forms for parenteral administration include injection and infusion formulations in the form of solutions, suspensions, emulsions, lyophilizates or sterile powders.

For the other administration routes, suitable examples are inhalation medicaments (including powder inhalers, nebulizers), nasal drops, solutions or sprays; tablets for lingual, sublingual or buccal administration, films/wafers or capsules, suppositories, ear or eye preparations, vaginal capsules, aqueous suspensions (lotions, shaking mixtures), lipophilic suspensions, ointments, creams, transdermal therapeutic systems (for example patches), milk, pastes, foams, dusting powders, implants, intrauterine coils, vaginal rings or stents.

The inventive compounds can be converted to the administration forms mentioned. This can be done in a manner known per se, by mixing with inert, nontoxic, pharmaceutically suitable excipients. These excipients include carriers (for example microcrystalline cellulose, lactose, mannitol), solvents (e.g. liquid polyethylene glycols), emulsifiers and dispersing or wetting agents (for example sodium dodecylsulphate, polyoxysorbitan oleate), binders (for example polyvinylpyrrolidone), synthetic and natural polymers (for example albumin), stabilizers (e.g. antioxidants, for example ascorbic acid), dyes (e.g. inorganic pigments, for example iron oxides) and flavour and/or odour correctants.

The present invention further provides medicaments which comprise at least one inventive compound, typically together with one or more inert, nontoxic, pharmaceutically suitable excipients, and the use thereof for the aforementioned purposes.

In the case of oral administration, the amount is about 0.01 to 100 mg/kg of body weight per day. The amount of a compound of the formula I to be administered varies within a wide range and can cover any effective amount. Depending on the condition to be treated and the mode of administration, the amount of the compound administered may be 0.01-100 mg/kg of body weight per day.

In spite of this, it may be necessary to deviate from the amounts specified, specifically depending on body weight, administration route, individual behaviour towards the active ingredient, type of formulation, and time or interval of administration. For instance, less than the aforementioned minimum amount may be sufficient in some cases, while the upper limit mentioned has to be exceeded in other cases. In the case of administration of greater amounts, it may be advisable to divide them into several individual doses over the day.

The percentages in the tests and examples which follow are, unless indicated otherwise, percentages by weight; parts are parts by weight. Solvent ratios, dilution ratios and concentration data for liquid/liquid solutions are based in each case on volume.

The present invention further provides medicaments for treatment and prophylaxis of endometriosis, of uterine leiomyoma, of uterine bleeding disorders, of dysmenorrhoea, of prostate carcinoma, of prostate hyperplasia, of acne, of seborrhoea, of hair loss, of premature sexual maturity, of polycystic ovary syndrome, of breast cancer, of lung cancer, of endometrial carcinoma, of renal cell carcinoma, of bladder carcinoma, of non-Hodgkins lymphoma, of chronic obstructive pulmonary disease (COPD), of obesity, or of inflammation-related pain.

The present invention further provides for the use of the compounds of the general formula (I) in the form of a pharmaceutical formulation for enteral, parenteral, vaginal, intrauterine and oral administration.

Some of the inventive compounds can be prepared proceeding from methyl 17-oxooestra-1,3,5(10)-triene-3-carboxylate, which is known from the literature (Steroids, 1995, 60, 3, 299-306) (Synthesis Scheme 1):

The conversion to Intermediate 1 is effected by the use of trifluoromethanesulphonic anhydride or N,N-bis[(trifluoromethyl)sulphonyl]aniline in the presence of a base such as pyridine, 2,6-dimethylpyridine or 2,6-di-tert-butylpyridine or in the presence of a tertiary amine such as triethylamine or diisopropylethylamine or by use of alkali metal hexamethylsilazanes or lithium diisopropylamide (LDA) (J. Med. Chem., 1995, 38, 2463-2471, J. Org. Chem., 1985, 50, 1990-1992, JACS, 2009, 131, 9014-9019, Archiv der Pharmazie (Weinheim, Germany), 2001, 334, 12, 373-374). Preference is given to the reaction with trifluoromethanesulphonic anhydride in the presence of 2,6-di-tert-butylpyridine in dichloromethane.

Intermediate 2 is prepared with the aid of the Suzuki reaction, which is known to those skilled in the art. For this purpose, Intermediate 1 is reacted with a nitrogen-containing aromatic boronic acid, a boronic ester, for example a pinacol boronate, an MIDA boronate (D. M. Knapp et al., J. Am. Chem. Soc. 2009, 131, 6961) or with a trifluoroborate salt (G. A. Molander et al., J. Org. Chem. 2009, 74, 973). Useful catalysts include a multitude of palladium catalysts, for example tetrakis(triphenylphosphine)palladium(0), bis(triphenylphosphine)palladium(II) dichloride or [1,3-bis(2,6-diisopropylphenyl)imidazol-2-ylidene](3-chloropyridyl)palladium(II) dichloride (CAS 905459-27-0). Alternatively, it is possible to use a palladium source, for example palladium(II) acetate, palladium(II) chloride or Pd(dba)$_2$, in combination with a phosphorus ligand, for example triphenylphosphine, SPhos (D. M. Knapp et. al., J. Am. Chem. Soc. 2009, 131, 6961) or RuPhos (G. A. Molander, J. Org. Chem. 2009, 74, 973). Preference is given to the reaction with boronic acids in the presence of tetrakis(triphenylphosphine)palladium(0) or [1,3-bis(2,6-diisopropylphenyl)imidazol-2-ylidene](3-chloropyridyl)palladium(II) dichloride.

Intermediate 3 is prepared by hydrolysis of the methyl ester by methods known to those skilled in the art. For this purpose, Intermediate 2 in a solvent such as tetrahydrofuran (THF), methanol or dimethyl sulphoxide (DMSO) or in a mixture of methanol and THF is admixed with sodium hydroxide solution or an aqueous lithium hydroxide solution. The mixture is optionally heated. Preference is given to the reaction in THF and methanol in the presence of sodium hydroxide solution or aqueous lithium hydroxide solution at 40° C.

The example compounds are prepared proceeding from Intermediates 3 by an amide coupling with an amine. For the amide coupling (stage A), useful reagents are those known to the person skilled in the art, for example N,N'-dicyclohexylcarbodiimide (DCC), N-[3-(dimethylamino)propyl]-N-ethylcarbodiimide hydrochloride (EDC) [CAS 25952-53-8] or HATU (O-(7-azabenzotriazol-1-yl)-N,N,N',N'-tetramethyluronium hexafluorophosphate. In addition, additives utilized may also be reagents such as 1H-benzotriazol-1-ol hydrate (HOBt hydrate [CAS 123333-53-9]) or N,N-dimethylpyridin-4-amine (DMAP). Bases used may, for example, be pyridine, triethylamine or diisopropylethylamine. Preference is given to conversion by means of EDC, HOBt hydrate and triethylamine. For the conversion of the carboxylic ester to the carboxylic acid (stage B), it is possible—if the ester is, for example, a methyl, ethyl or benzyl ester—to use hydrolysis methods as described for the preparation of the Intermediates 3. If the ester is a tert-butyl carboxylate, this can be converted to the carboxylic acid by methods known to those skilled in the art, for example by the reaction with trifluoroacetic acid in dichloromethane or chloroform or by the reaction with hydrogen chloride in 1,4-dioxane. The reaction with trifluoroacetic acid in dichloromethane is preferred.

Synthesis Scheme 1 (preparation of some of the example compounds where R3 = H)

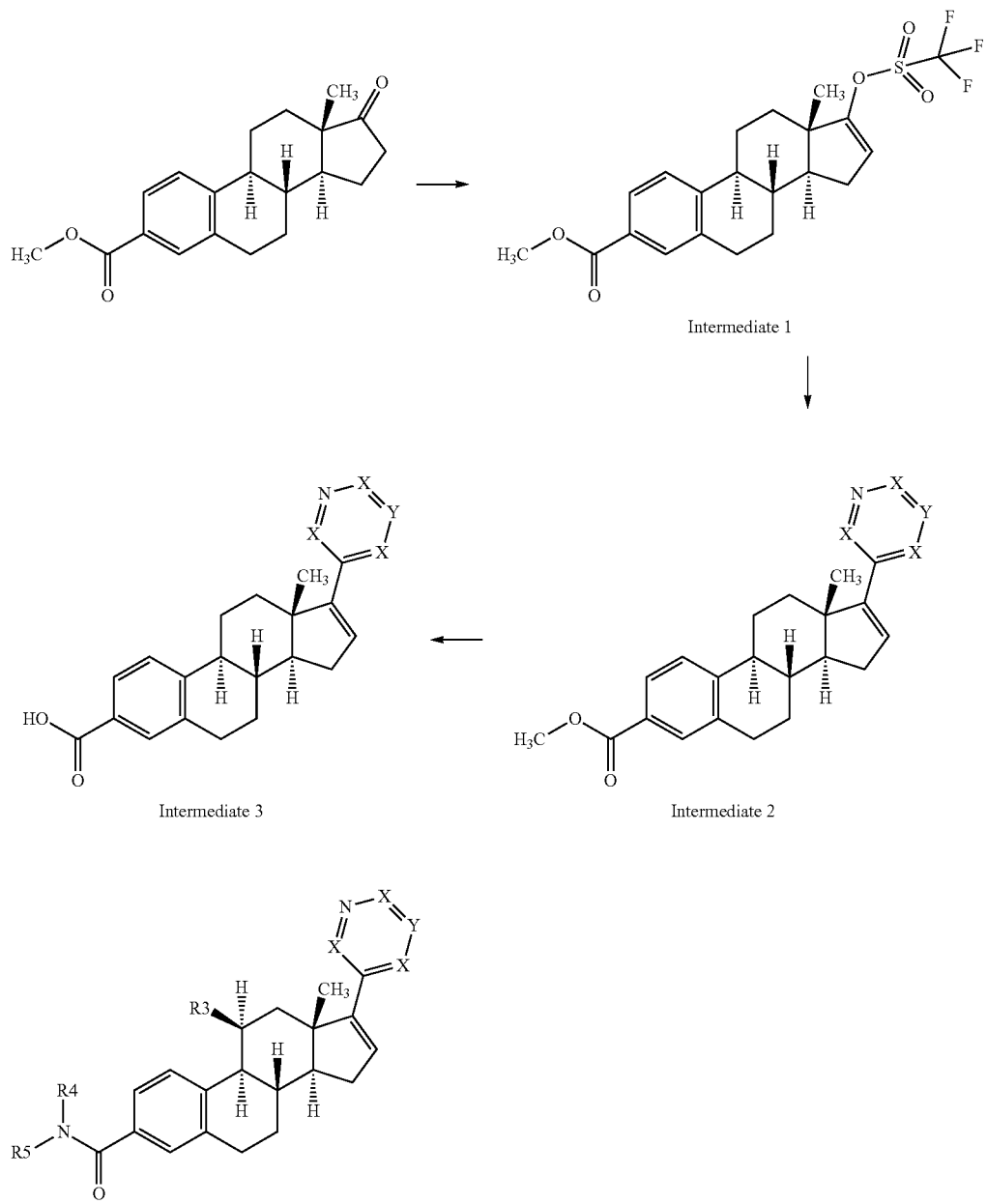

Some of the inventive compounds of the formula (I) where R5=F and R6=H can be prepared as described in Synthesis Scheme 2:

3,11α-Dihydroxyoestra-1,3,5(10)-trien-17-one (CAS 5210-15-1) is reacted with acetic anhydride and pyridine in the presence of 4-dimethylaminopyridine (DMAP) in dichloromethane to give Intermediate 4. The conversion to Intermediate 5 is effected with sodium hydrogencarbonate in methanol. The reaction of Intermediate 5 with 1,1,2,2,3,3,4,4,4-nonafluorobutane-1-sulphonyl fluoride and potassium carbonate leads to Intermediate 6, which is converted with palladium(II) acetate, 1,3-bis(diphenylphosphino)propane, triethylamine in methanol and DMSO in an autoclave in a carbon monoxide atmosphere to give Intermediate 7. The conversion to Intermediate 8 is effected by methods as described for the preparation of Intermediate 1. The transformation of Intermediate 8 to Intermediate 9 is performed by methods as described for the preparation of Intermediate 2. Intermediate 9 is hydrolysed with potassium carbonate in methanol to give Intermediate 10. The transformation to Intermediate 11 is performed with 1,8-diazabicyclo[5.4.0]undec-7-ene and 1,1,2,2,3,3,4,4,4-nonafluorobutane-1-sulphonyl fluoride in THF. The hydrolysis of Intermediate 11 to Intermediate 12 is effected with conditions as described for the preparation of Intermediate 3. Preference is given to the reaction in THF and methanol in the presence of aqueous lithium hydroxide solution. The preparation of some of the example compounds proceeding from Intermediate 12 is effected analogously to the example compounds proceeding from Intermediate 3 as described in Synthesis Scheme 1.

Synthesis Scheme 2 (preparation of some of the example compounds where R3 = F)
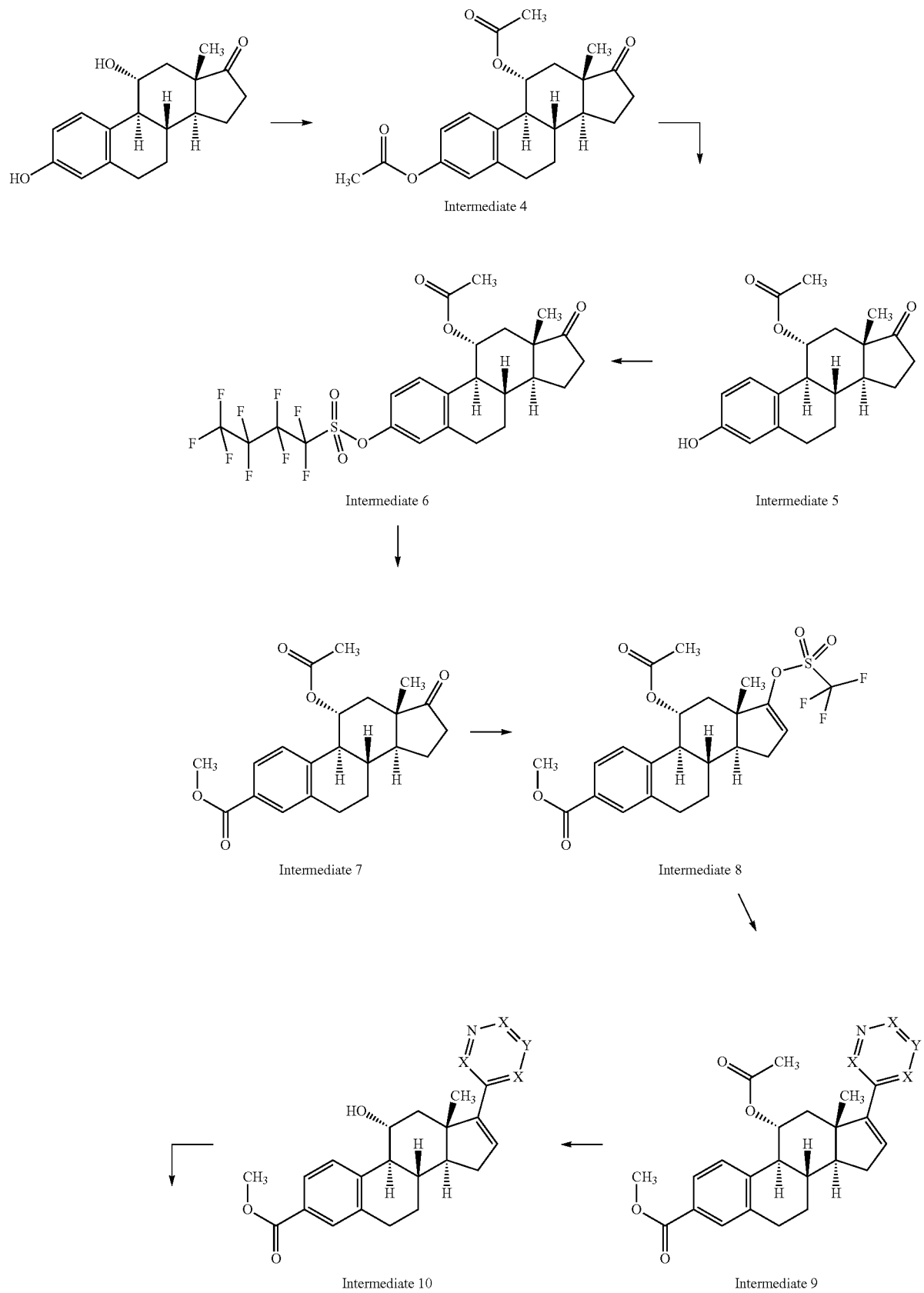

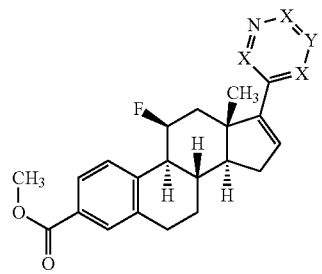

Intermediate 11

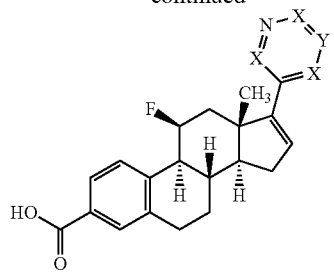

Intermediate 12

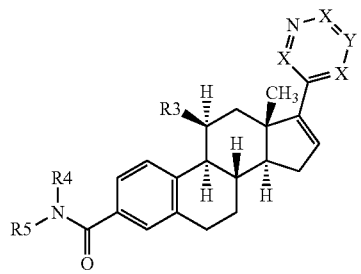

Some further inventive compounds of the formula (I) can be prepared as illustrated in Synthesis Scheme 3. Proceeding from 17-oxooestra-1,3,5(10)-triene-3-carboxamide (E. Morera, G. Ortar, T H L, 1998, 39, 2835-2838), Intermediate 13 is obtained by reaction with hydrazine hydrate in the presence of hydrazine sulphate. Intermediate 14 is obtained from Intermediate 13 by reaction with iodine in the presence of triethylamine. Intermediate 14 can then be converted with the aid of the Suzuki reaction as in Synthesis Scheme 1 to the title compounds.

Synthesis Scheme 3 (preparation of some of the example compounds of formula (I))

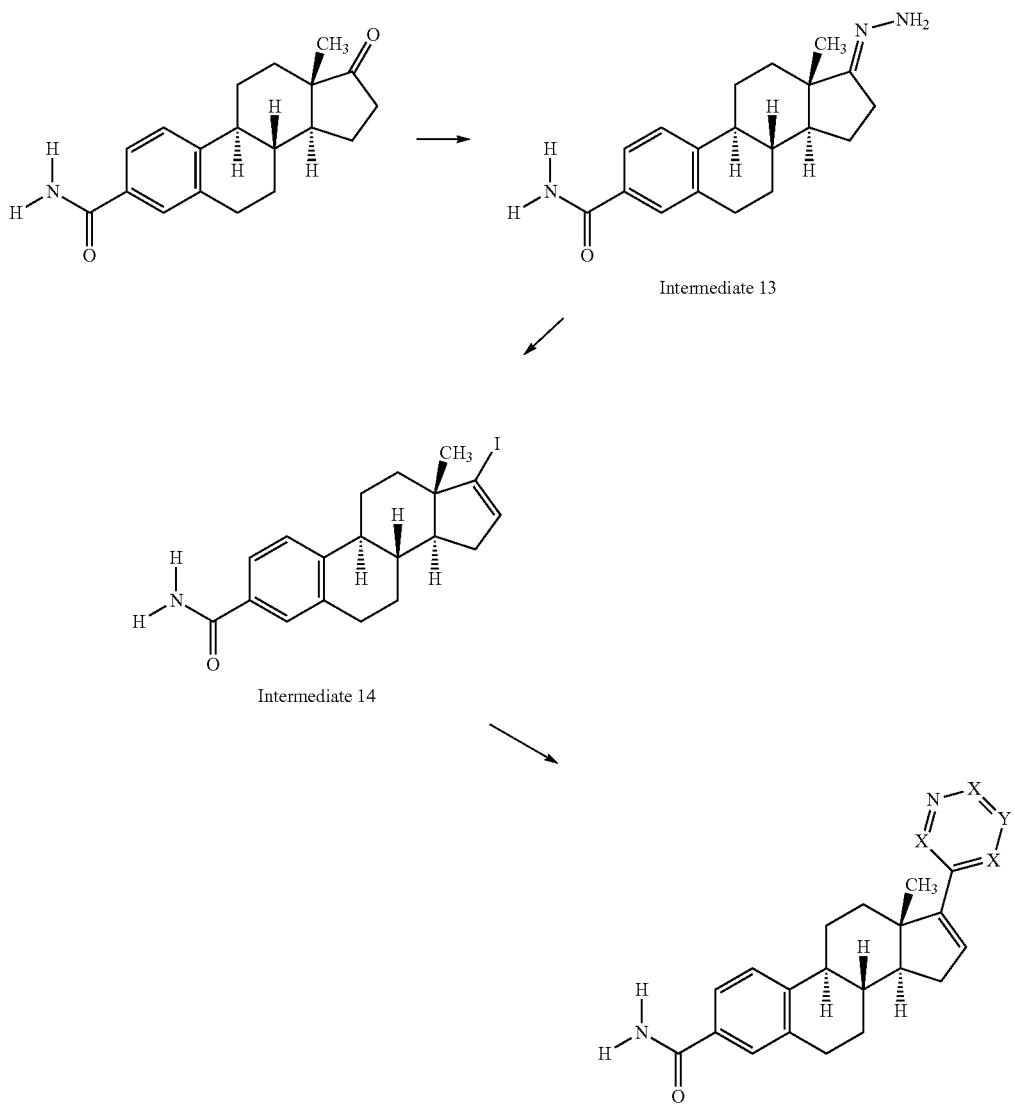

Intermediate 13

Intermediate 14

Some further inventive compounds of the formula (I) can be prepared as illustrated in Synthesis Scheme 4. Proceeding from 17-oxooestra-1,3,5(10)-triene-3-carbonitrile (Journal of the Chemical Society, 1964, 5889), Intermediate 15 is obtained as in the preparation of Intermediate 1. Intermediate 16 can then be prepared with the aid of the Suzuki reaction as in Synthesis Scheme 1. Proceeding from Intermediate 16, some of the inventive compounds are obtained by reaction with sodium perborate tetrahydrate in an alcoholic solvent such as methanol or ethanol (A. McKillop, D. Kemp, Tetrahedron, 1989, 45, 11, 3299-3306). Reaction in ethanol in a microwave is preferred.

Purification of the Inventive Compounds

In some cases, the inventive compounds were purified by preparative HPLC with the aid of an autopurifier system from Waters (detection of the compounds by UV detection and electrospray ionization) in combination with commercially available prepacked HPLC columns (for example XBridge column (from Waters), C18, 5 μm, 30×100 mm). The solvent system used was acetonitrile/water with addition of formic acid.

In some cases, the following method was used for the preparative HPLC separation:

Synthesis Scheme 4 (preparation of some of the example compounds of the formula (I))

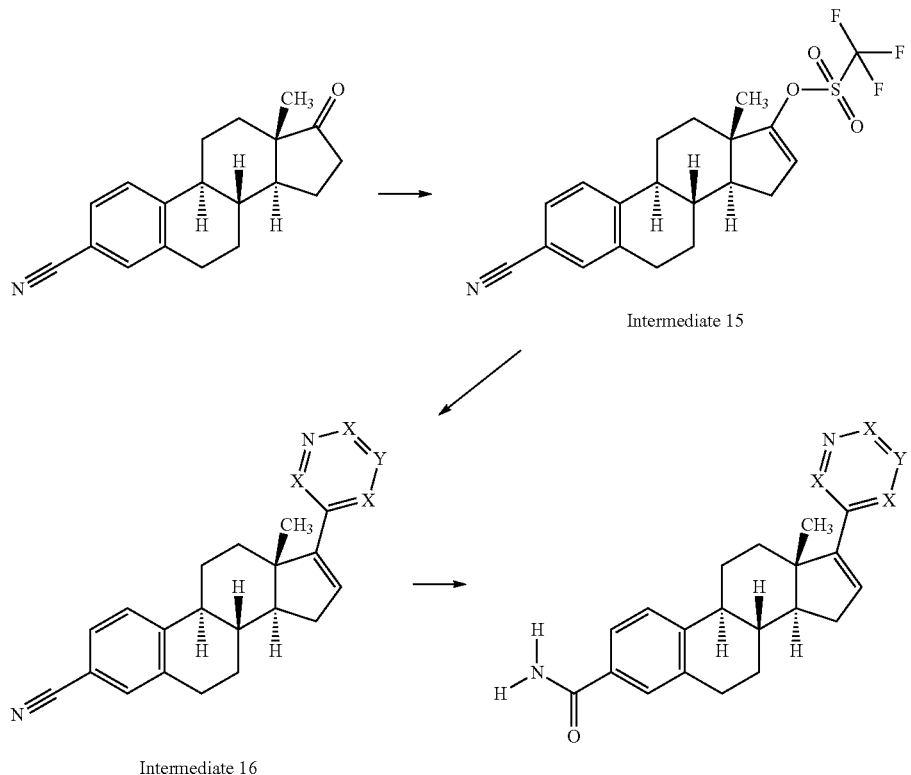

Intermediate 15

Intermediate 16

LIST OF CHEMICAL ABBREVIATIONS

Abbreviations and Acronyms

| | |
|---|---|
| DMF | N,N-dimethylformamide |
| DMSO | dimethyl sulphoxide |
| NMP | 1-methylpyrrolidin-2-one |
| THF | tetrahydrofuran |
| h | hour(s) |
| HPLC | high-pressure, high-performance liquid chromatography |
| LC-MS | liquid chromatography-coupled mass spectroscopy |
| ES-MS | electrospray mass spectrometry |
| min | minute(s) |
| MS | mass spectrometry |
| NMR | nuclear magnetic resonance spectroscopy |
| Rt | retention time |
| TFA | trifluoroacetic acid |
| room temp. | room temperature |

| | |
|---|---|
| System: | Waters autopurification system: Pump 2545, Sample Manager 2767, CFO, DAD 2996, ELSD 2424, SQD |
| Column: | XBridge C18 5 μm 100 × 30 mm |
| Solvent: | A = $H_2O$ + 0.1% by vol. of formic acid (99%) |
| | B = acetonitrile |
| Gradient: | 0-1 min 1% B, 1-8 min 1-99% B, 8-10 min 99% B |
| Flow rate: | 50 ml/min |
| Temperature: | room temp. |
| Injection: | 1 × 2.5 ml |
| Detection: | DAD scan range 210-400 nm |
| | MS ESI+, ESI−, scan range 160-1000 m/z |

For removal of the HPLC solvent mixture, a freeze-drying operation or a vacuum centrifugation was used.

In some cases, the inventive compounds were purified by chromatography on silica gel. This was done using prepacked silica gel cartridges (for example an ISOLUTE® Flash silica gel (Biotage, formerly Separtis) a flash chromatography silica gel cartridge) in combination with a FLASH-MASTER™ II (Argonaut/Biotage)) chromatography system, and chromatography solvents or mixtures, for example hexane, ethyl acetate, and dichloromethane and methanol.

Structure Analysis of the Inventive Compounds:

In some cases, the inventive compounds were analysed by LC-MS.

In some cases, the following analysis method was used (Method 1):

Instrument: Waters Acquity UPLC-MS SQD; column: Acquity UPLC BEH C18 1.7 50×2.1 mm; eluent A: water+ 0.1% by vol. of formic acid (99%), eluent B: acetonitrile; gradient: 0-1.6 min 1-99% B, 1.6-2.0 min 99% B; flow rate 0.8 ml/min; temperature: 60° C.; injection: 2 µl; DAD scan: 210-400 nm In the NMR data of the inventive compounds, the following meanings apply:

| | |
|---|---|
| s | singlet |
| d | doublet |
| t | triplet |
| q | quartet |
| quin | quintet |
| m | multiplet |
| br | broad |
| mc | centred multiplet |

Synthesis of the Inventive Compounds

Intermediate 1 methyl 17-{[(trifluoromethyl)sulphonyl]oxy}oestra-1,3,5(10),16-tetraene-3-carboxylate

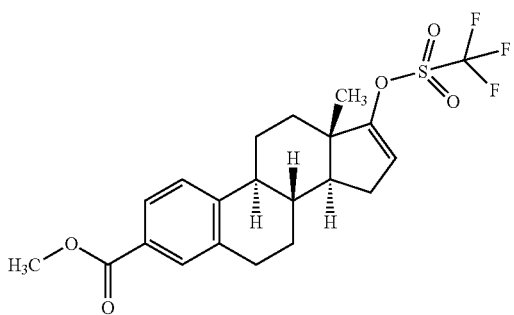

To a mixture of 5.00 g (16.0 mmol) of methyl 17-oxooestra-1,3,5(10)-triene-3-carboxylate (Steroids, 1995, 60, 3, 299-306) in 100 ml of dichloromethane and 5.3 ml of 2,6-di-tert-butylpyridine were added dropwise 3.2 ml of trifluoromethanesulphonic anhydride and the mixture was stirred at room temp. for 20 h. Thereafter, the mixture was poured cautiously onto 250 ml of saturated aqueous sodium hydrogencarbonate solution, the mixture was stirred for 40 min and the phases were separated, followed by extraction twice with dichloromethane. Subsequently, the combined organic phases were washed with saturated sodium hydrogencarbonate solution and sodium chloride solution, dried over sodium sulphate and concentrated. After extraction by stirring with hexane, the yield was 4.55 g of the title compound in solid form.

$^1$H NMR (300 MHz, CHLOROFORM-d): δ [ppm]=1.01 (s, 3H), 1.37-1.74 (m, 5H), 1.81 (td, 1H), 1.88-2.02 (m, 2H), 2.05-2.19 (m, 1H), 2.27-2.55 (m, 3H), 2.83-3.11 (m, 2H), 3.90 (s, 3H), 5.63 (dd, 1H), 7.32 (d, 1H), 7.68-7.90 (m, 2H).

Intermediate 2-a methyl 17-(5-fluoropyridin-3-yl)oestra-1,3,5(10),16-tetraene-3-carboxylate

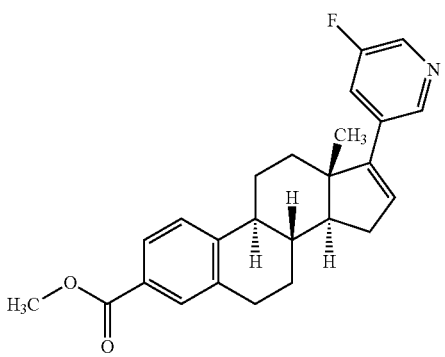

8.00 g (2.25 mmol) of methyl 17-{[(trifluoromethyl)sulphonyl]oxy}oestra-1,3,5(10),16-tetraene-3-carboxylate and 3.55 g (1.4 equiv.) of 5-fluoropyridine-3-boronic acid were initially charged in 60 ml of toluene and 40 ml of ethanol. Then 1.53 g (2.0 equiv.) of lithium chloride, 24 ml of 2M aqueous sodium carbonate solution and 1.04 g (5 mol %) of tetrakis(triphenylphosphine)palladium(0) were added and the mixture was heated to 100° C. for 3.5 h. Thereafter, water was added, and the mixture was extracted three times with ethyl acetate, washed with saturated sodium hydrogencarbonate solution and sodium chloride solution, and concentrated. After column chromatography purification on silica gel (hexane/ethyl acetate), the yield was 5.5 g (78% of theory) of the title compound.

$^1$H NMR (400 MHz, CHLOROFORM-d): δ [ppm]=1.06 (s, 3H), 1.47-1.63 (m, 1H), 1.63-1.78 (m, 3H), 1.84 (td, 1H), 1.98-2.06 (m, 1H), 2.13-2.26 (m, 2H), 2.35-2.51 (m, 3H), 2.98 (dd, 2H), 3.90 (s, 3H), 6.10 (dd, 1H), 7.32-7.44 (m, 2H), 7.76-7.86 (m, 2H), 8.36 (br. s., 1H), 8.48 (s, 1H).

Intermediate 2-b methyl 17-(5-methoxypyridin-3-yl)oestra-1,3,5(10), 16-tetraene-3-carboxylate

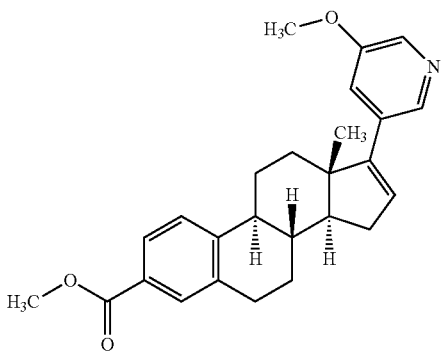

Analogously to the preparation of Intermediate 2-a, 2.00 g (4.50 mmol) of Intermediate 1 were reacted with 0.96 g (1.4 equiv.) of (5-methoxypyridin-3-yl)boronic acid in the presence of 260 mg of tetrakis(triphenylphosphine)palladium(0) at 100° C. overnight to give 1.4 g (76% of theory) of the title compound.

¹H NMR (300 MHz, CHLOROFORM-d): δ [ppm]=1.05 (s, 3H), 1.43-1.60 (m, 1H), 1.62-1.89 (m, 4H), 1.95-2.08 (m, 1H), 2.10-2.25 (m, 2H), 2.30-2.53 (m, 3H), 2.98 (dd, 2H), 3.88 (s, 3H), 3.90 (s, 3H), 6.00-6.08 (m, 1H), 7.16-7.22 (m, 1H), 7.35 (d, 1H), 7.75-7.83 (m, 2H), 8.20 (d, 1H), 8.28 (d, 1H).

Intermediate 2-c methyl 17-(pyrimidin-5-yl)oestra-1,3,5(10),16-tetraene-3-carboxylate

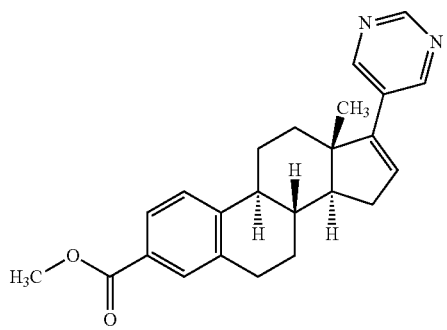

Analogously to the preparation of Intermediate 2-a, 3.00 g (6.75 mmol) of Intermediate 1 were reacted with 1.17 g (1.4 equiv.) of pyrimidinyl-5-boronic acid in the presence of 390 mg of tetrakis(triphenylphosphine)palladium(0) at 100° C. overnight to give 1.70 g (64% of theory) of the title compound.

¹H NMR (400 MHz, CHLOROFORM-d): δ [ppm]=1.06 (s, 3H), 1.47-1.59 (m, 1H), 1.65-1.80 (m, 3H), 1.85 (td, 1H), 1.98-2.06 (m, 1H), 2.12-2.25 (m, 2H), 2.36-2.53 (m, 3H), 2.98 (dd, 2H), 3.90 (s, 3H), 6.14 (dd, 1H), 7.35 (d, 1H), 7.76-7.85 (m, 2H), 8.76 (s, 2H), 9.09 (s, 1H).

Intermediate 2-d methyl 17-[5-(trifluoromethyl)pyridin-3-yl]oestra-1,3,5(10),16-tetraene-3-carboxylate

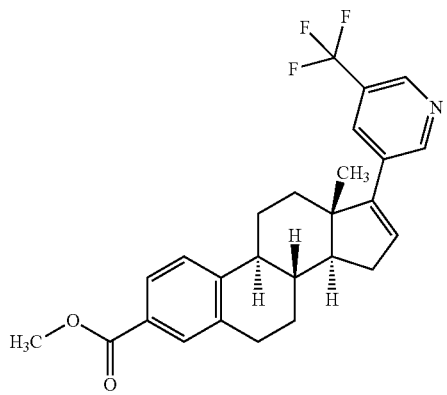

Analogously to the preparation of Intermediate 2-a, 1.66 g (3.74 mmol) of Intermediate 1 were reacted with 1.00 g (1.4 equiv.) of [5-(trifluoromethyl)pyridin-3-yl]boronic acid in the presence of 216 mg of tetrakis(triphenylphosphine)palladium(0) at 100° C. overnight to give 1.20 g (73% of theory) of the title compound.

¹H NMR (300 MHz, CHLOROFORM-d): δ [ppm]=1.08 (s, 3H), 1.49-1.89 (m, 6H), 1.97-2.09 (m, 1H), 2.09-2.28 (m, 2H), 2.35-2.54 (m, 3H), 2.98 (dd, 2H), 3.90 (s, 3H), 6.15 (dd, 1H), 7.36 (s, 1H), 7.77-7.85 (m, 2H), 7.88 (s, 1H), 8.83 (s, 2H).

Intermediate 2-e methyl 17-(5-cyanopyridin-3-yl)oestra-1,3,5(10),16-tetraene-3-carboxylate

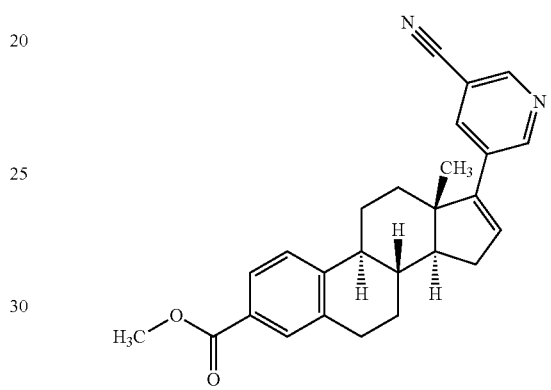

Analogously to the preparation of Intermediate 2-a, 650 mg (1.46 mmol) of Intermediate 1 were reacted with 216 mg (1.0 equiv.) of (5-cyanopyridin-3-yl)boronic acid in the presence of 84 mg of tetrakis(triphenylphosphine)palladium(0) at 120° C. in a microwave (100 watts) within 90 min. After column chromatography purification on silica gel (hexane/ethyl acetate), the yield was 109 mg of crude product. C₂₆H₂₆N₂O₂ MS (ESIpos) mass found: 398.00.

¹H NMR (300 MHz, DMSO-d₆): δ [ppm]=1.00 (s, 3H), 2.82-2.96 (m, 2H), 3.79 (s, 3H), 6.31-6.36 (m, 1H), 7.40 (d, 1H), 7.61-7.71 (m, 2H), 8.27 (t, 1H), 8.85-8.89 (m, 2H).

Intermediate 2-f methyl 17-(3-pyridyl)oestra-1,3,5(10),16-tetraene-3-carboxylate

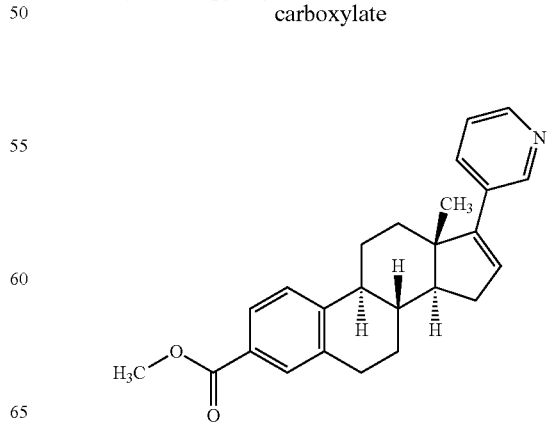

Analogously to the preparation of Intermediate 2-a, 500 mg (1.13 mmol) of Intermediate 1 were reacted with 194 mg (1.4 equiv.) of (5-cyanopyridin-3-yl)boronic acid in the presence of 39 mg of bis(triphenylphosphine)palladium(II) chloride at 100° C. within 18 h. The reaction mixture was extracted three times with ethyl acetate and the combined organic phases were concentrated. The yield was 462 mg of a crude product. $C_{25}H_{27}NO_2$ MS (ESIpos) mass found: 373.00

Intermediate 3-a 17-(5-fluoropyridin-3-yl)oestra-1,3,5(10),16-tetraene-3-carboxylic acid

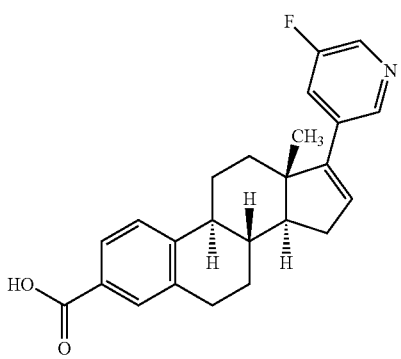

372 mg (0.95 mmol) of Intermediate 2-a were initially charged in 50 ml of THF and 3 ml of methanol. Subsequently, a solution of 120 mg of lithium hydroxide in 3 ml of water was added and the mixture was stirred at room temp. for 18 h. Subsequently, another 5 equiv. of lithium hydroxide were added, and the mixture was stirred at room temp. for 24 h and stirred at 40° C. for 18 h. Thereafter, the mixture was diluted with water and acidified to pH 4 with 10% aqueous citric acid solution, ethyl acetate was added and solids were filtered off. After the solids had been washed with ethyl acetate and water and dried, the yield was 153 mg (43% of theory) of the title compound. The organic phase of the filtrate was removed and the aqueous phase was extracted twice with ethyl acetate. After the combined organic phases had been washed with sodium chloride solution, dried over sodium sulphate and concentrated, a residue was obtained, which was extracted by stirring with diethyl ether. After drying, a further 143 mg (40% of theory) of the title compound were obtained.

$^1$H NMR (300 MHz, DMSO-$d_6$): δ [ppm]=0.99 (s, 3H), 1.38-1.78 (m, 5H), 1.83-1.97 (m, 1H), 2.05-2.21 (m, 2H), 2.25-2.43 (m, 3H), 2.89 (dd, 2H), 6.27 (dd, 1H), 7.36 (d, 1H), 7.58-7.72 (m, 3H), 8.43 (d, 1H), 8.49 (t, 1H).

Intermediate 3-b 17-(5-methoxypyridin-3-yl)oestra-1,3,5(10),16-tetraene-3-carboxylic acid

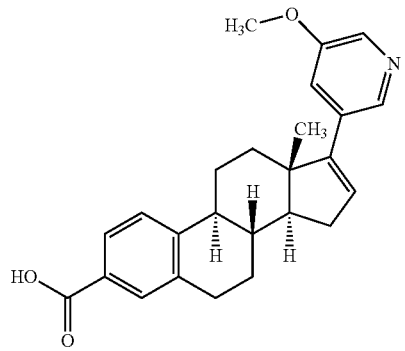

A solution of 1.4 g (3.47 mmol) of methyl 17-(5-methoxypyridin-3-yl)oestra-1,3,5(10),16-tetraene-3-carboxylate in 30 ml of THF, 4 ml of methanol and 8.7 ml of 2M sodium hydroxide solution was stirred at room temp. overnight and then heated to 40° C. for 8.5 h. Subsequently, the mixture was diluted with water, acidified with 10% citric acid solution to pH=4, extracted three times with ethyl acetate, washed with sodium chloride solution and concentrated. After the crude product had been extracted by stirring with ether, the yield was 1.2 g (89% of theory) of the title compound.

$^1$H NMR (300 MHz, DMSO-$d_6$): δ [ppm]=0.98 (s, 3H), 1.34-1.81 (m, 5H), 1.84-1.97 (m, 1H), 2.03-2.19 (m, 2H), 2.21-2.43 (m, 3H), 2.89 (dd, 2H), 3.81 (s, 3H), 6.12-6.20 (m, 1H), 7.20-7.29 (m, 1H), 7.36 (d, 1H), 7.59-7.70 (m, 2H), 8.15 (d, 1H), 8.20 (d, 1H).

Intermediate 3-c 17-(pyrimidin-5-yl)oestra-1,3,5(10),16-tetraene-3-carboxylic acid

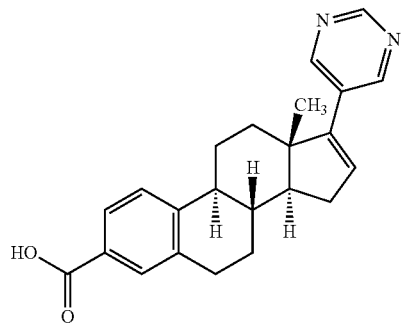

A mixture of 1.70 g (4.54 mmol) of methyl 17-(pyrimidin-5-yl)oestra-1,3,5(10),16-tetraene-3-carboxylate, 40 ml of THF, 11.3 ml of 2M sodium hydroxide solution and 5 ml of methanol was stirred at room temp. overnight, then at 40° C. for 8.5 h and then at room temp. overnight. Thereafter, the mixture was diluted with water and acidified to pH=4 with 10% citric acid solution, and ethyl acetate was added. The insoluble solids were filtered off and dried. The yield was 1.3 g (79% of theory) of the title compound.

$^1$H NMR (300 MHz, DMSO-d$_6$): δ [ppm]=0.99 (s, 3H), 1.39-1.79 (m, 5H), 1.84-1.97 (m, 1H), 2.06-2.21 (m, 2H), 2.26-2.44 (m, 3H), 2.89 (dd, 2H), 6.28-6.33 (m, 1H), 7.36 (d, 1H), 7.59-7.69 (m, 2H), 8.83 (s, 2H), 9.04 (s, 1H), 12.7 (br. s., 1H).

Intermediate 3-d

17-[5-(trifluoromethyl)pyridin-3-yl]oestra-1,3,5(10), 16-tetraene-3-carboxylic acid

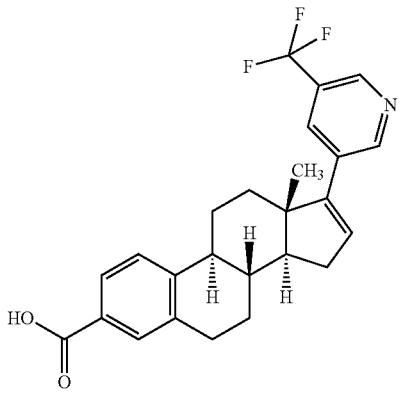

1.2 g of methyl 17-[5-(trifluoromethyl)pyridin-3-yl] oestra-1,3,5(10),16-tetraene-3-carboxylate were initially charged in 12 ml of THF, a solution of 0.23 g of lithium hydroxide in 12 ml of water was added and the mixture was stirred at 40° C. overnight. Subsequently, the mixture was diluted with water, acidified to pH=4 with 10% citric acid solution and extracted three times with ethyl acetate. Thereafter, the mixture was washed with sodium chloride solution, concentrated and extracted by stirring with diethyl ether. Yield: 850 mg of the title compound in solid form.

$^1$H NMR (400 MHz, DMSO-d$_6$): δ [ppm]=1.01 (s, 3H), 1.37-1.50 (m, 1H), 1.50-1.69 (m, 3H), 1.76 (td, 1H), 1.86-1.95 (m, 1H), 2.08-2.19 (m, 2H), 2.27-2.44 (m, 3H), 2.90 (dd, 2H), 6.36 (dd, 1H), 7.36 (d, 1H), 7.61-7.68 (m, 2H), 8.04 (s, 1H), 8.82-8.86 (m, 1H), 8.90 (d, 1H), 12.7 (br. s., 1H).

Intermediate 3-e 17-(5-cyanopyridin-3-yl)oestra-1,3,5(10),16-tetraene-3-carboxylic acid

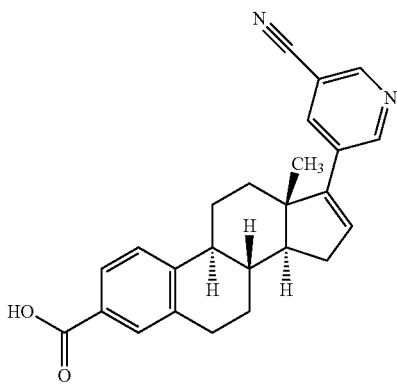

Analogously, 105 mg of methyl 17-(5-cyanopyridin-3-yl) oestra-1,3,5(10),16-tetraene-3-carboxylate were reacted with lithium hydroxide in THF and methanol. After purification by preparative HPLC (acetonitrile/water/formic acid), the yield was 27 mg of the title compound.

$^1$H NMR (300 MHz, DMSO-d$_6$): δ [ppm]=1.00 (s, 3H), 1.35-1.81 (m, 6H), 1.84-1.96 (m, 1H), 2.06-2.21 (m, 2H), 2.25-2.50 (m, partly concealed by DMSO signal), 2.83-2.95 (m, 2H), 6.34 (br. s., 1H), 7.36 (d, 1H), 7.58-7.70 (m, 2H), 8.27 (t, 1H), 8.83-8.90 (m, 2H), 12.7 (s).

Intermediate 3-f 17-(3-pyridyl)oestra-1,3,5(10),16-tetraene-3-carboxylic acid

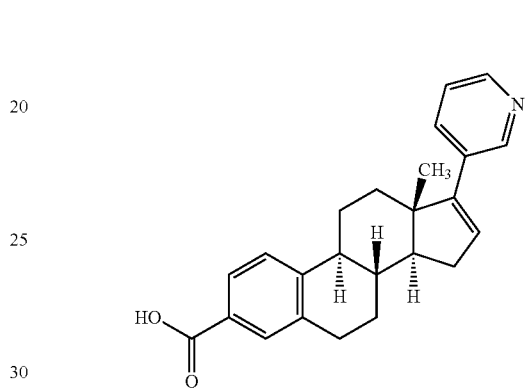

A mixture of 462 mg of methyl 17-(3-pyridyl)oestra-1,3, 5(10),16-tetraene-3-carboxylate, 3.1 ml of 2M sodium hydroxide solution, 4 ml of THF and 1 ml of methanol was stirred at 40° C. for 18 h. Subsequently, the mixture was diluted with water, acidified to pH 4 with ten percent citric acid solution and admixed with ethyl acetate. Thereafter, the insoluble solids were filtered off, washed with water and ethyl acetate, and dried. Yield: 375 mg (84% of theory) of a solid. $C_{24}H_{25}NO_2$ MS (ESIpos) mass found: 359.00.

$^1$H NMR (300 MHz, DMSO-d$_6$): δ [ppm]=0.99 (s, 3H), 1.38-1.78 (m, 5H), 1.81-1.97 (m, 1H), 2.02-2.19 (m, 2H), 2.19-2.44 (m, 4H), 2.83-2.96 (m, 2H), 6.09-6.15 (m, 1H), 6.03-6.24 (m, 1H), 7.29-7.40 (m, 2H), 7.57-7.68 (m, 2H), 7.77 (dt, 1H), 8.42 (dd, 1H), 8.59 (d, 1H).

Intermediate 4

17-oxooestra-1,3,5(10)-triene-3,11α-diyl diacetate

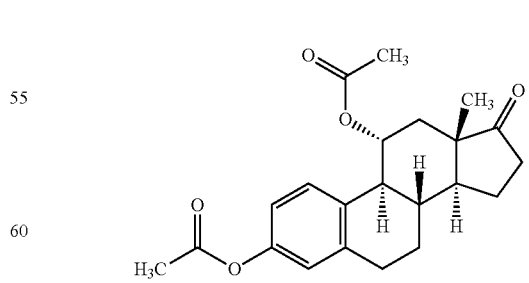

To a solution of 10.0 g (34.9 mmol) of 3,11α-dihydroxyoestra-1,3,5(10)-trien-17-one in 100 ml of dichloromethane were added dropwise, at room temp., 13.2 ml (4.0 equiv.) of acetic anhydride, and the reaction mixture was cooled to 5° C. Thereafter, 14.1 ml of pyridine were added dropwise and the mixture was cooled to room temp. for 10 min and stirred for 4 h. Thereafter, a spatula-tip of DMAP was added and the mixture was stirred at room temp. for 72 h. Then the mixture was poured onto 500 ml of water, the phases were separated, the aqueous phase was extracted with dichloromethane, and the organic phase was washed with 1M hydrochloric acid, water and sodium chloride solution, dried over sodium sulphate and concentrated. Yield: 12.9 g (99% of theory) of a white solid.

$^1$H NMR (400 MHz, DMSO-$d_6$): δ [ppm]=0.81 (s, 3H), 1.29 (t, 1H), 1.43-1.72 (m, 4H), 1.79-2.00 (m, 2H), 2.00-2.06 (m, 3H), 2.06-2.19 (m, 2H), 2.19-2.25 (m, 3H), 2.42-2.57 (m, obscured by DMSO signal), 2.76 (t, 2H), 5.26 (td, 1H), 6.82-6.89 (m, 2H), 6.97 (d, 1H).

Intermediate 5

3-hydroxy-17-oxooestra-1,3,5(10)-trien-11α-yl acetate

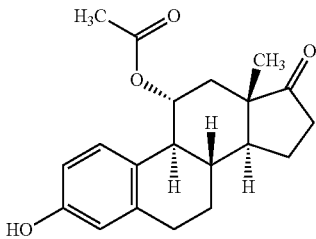

12.9 g (34.7 mmol) of 17-oxooestra-1,3,5(10)-triene-3,11α-diyl diacetate in 100 ml of methanol were admixed with 14.6 g (5 equiv.) of sodium hydrogencarbonate and the mixture was stirred at room temp. overnight. Thereafter, 100 ml of water and 1 ml of 1M hydrochloric acid were added and the mixture was stirred for 30 min. Thereafter, the mixture was extracted four times with ethyl acetate. In the course of this, a solid collected in the organic phase, which was filtered off with suction and dried. Yield: 3.74 g (33% of theory) of the title compound. In addition, 6.39 g (56% of theory) of the title compound were isolated by washing the organic phase with saturated sodium chloride solution, drying over sodium sulphate, concentrating, extracting the residue by stirring with ethyl acetate, filtration with suction and drying under reduced pressure.

$^1$H NMR (300 MHz, DMSO-$d_6$): δ [ppm]=0.79 (s, 3H), 1.25 (t, 1H), 1.36-1.69 (m, 4H), 1.75-1.98 (m, 2H), 1.98-2.18 (m, 5H), 2.34-2.43 (m), 2.68 (t, 2H), 5.16 (td, 1H), 6.43-6.55 (m, 2H), 6.76 (d, 1H), 9.07 (s, 1H).

Intermediate 6

3-{[(1,1,2,2,3,3,4,4,4-nonafluorobutyl)sulphonyl]oxy}-17-oxooestra-1,3,5(10)-trien-11α-yl acetate

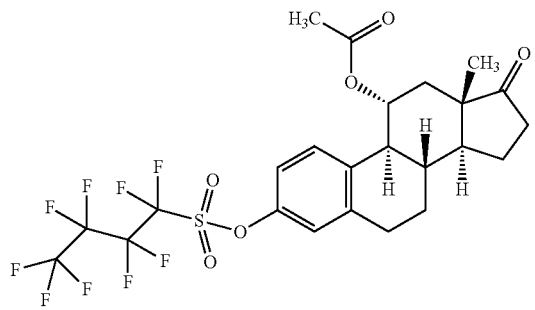

A solution of 10.1 g (31 mmol) of 3-hydroxy-17-oxooestra-1,3,5(10)-trien-11α-yl acetate in 20 ml of THF was admixed with 12.8 g (3 equiv.) of potassium carbonate and 6.5 ml (1.2 equiv.) of 1,1,2,2,3,3,4,4,4-nonafluorobutane-1-sulphonyl fluoride, and the mixture was heated under reflux for 4 h and stirred at room temp. for 18 h. Thereafter, another 1 ml of 1,1,2,2,3,3,4,4,4-nonafluorobutane-1-sulphonyl fluoride was added and the mixture was heated under reflux for 3 h. Thereafter, water and saturated sodium chloride solution were added, the mixture was stirred for 20 min, the phase was separated, and the aqueous phase was extracted three times with 50 ml each time of ethyl acetate. The combined organic phases were washed twice with 50 ml each time of water and twice with 50 ml of saturated sodium chloride solution, dried over sodium sulphate, filtered and concentrated. After column chromatography purification on silica gel (hexane/ethyl acetate), the yield was 18.1 g (96% of theory) of 3-{[(1,1,2,2,3,3,4,4,4-nonafluorobutyl)sulphonyl]oxy}-17-oxooestra-1,3,5(10)-trien-11α-yl acetate.

$^1$H NMR (400 MHz, DMSO-$d_6$): δ [ppm]=0.85 (s, 3H), 1.26-1.37 (m, 1H), 1.47-1.76 (m, 4H), 1.83-2.02 (m, 2H), 2.03-2.25 (m, 5H, includes s at 2.06 ppm), 2.41-2.47 (m), 2.59 (t, 1H), 2.77-2.95 (m, 2H), 5.29 (td, 1H), 7.15 (d, 1H), 7.23-7.29 (m, 2H).

Intermediate 7 methyl 11α-acetoxy-17-oxooestra-1,3,5(10)-triene-3-carboxylate

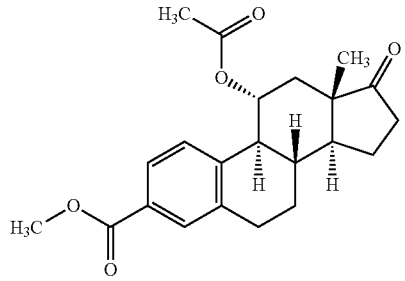

10.0 g (16.4 mmol) of 3-{[(1,1,2,2,3,3,4,4,4-nonafluorobutyl)sulphonyl]oxy}-17-oxooestra-1,3,5(10)-trien-11α-yl acetate, 230 mg (6 mol %) of palladium(II) acetate and 440 mg (6 mol %) of 1,3-bis(diphenylphosphino)propane were initially charged under argon in an autoclave, and 36 ml of methanol, 54 ml of DMSO and 6 ml of triethylamine were added. The reaction mixture was purged three times with carbon monoxide and stirred at carbon monoxide pressure 7.5 bar at room temp. for 30 min. Thereafter, the autoclave was decompressed and evacuated, and stirred at carbon monoxide pressure 6.8 bar at 70° C. for 3.5 h. This was followed by concentration, and the residue was taken up in water and ethyl acetate. The phases were separated and the aqueous phase was extracted twice with ethyl acetate. The combined organic phases were washed with 1M hydrochloric acid and saturated sodium hydrogencarbonate solution, dried over sodium sulphate and concentrated. After purification of the residue by column chromatography on silica gel (hexane/ethyl acetate), the yield was 5.96 g (98% of theory) of the title compound in solid form.

$^1$H NMR (300 MHz, DMSO-d$_6$): δ [ppm]=0.81 (s, 3H), 1.29 (t, 1H), 1.40-1.76 (m, 4H), 1.78-2.00 (m, 2H), 2.00-2.21 (m, 5H, includes s at 2.03 ppm), 2.37-2.52 (m, concealed by DMSO signal), 2.59 (t, 1H), 2.72-2.93 (m, 2H), 3.79 (s, 3H), 5.29 (td, 1H), 5.23-5.38 (m, 1H), 7.08 (d, 1H), 7.68-7.75 (m, 2H).

Intermediate 8 methyl 11α-acetoxy-17-{[(trifluoromethyl)sulphonyl]oxy}oestra-1,3,5(10),16-tetraene-3-carboxylate

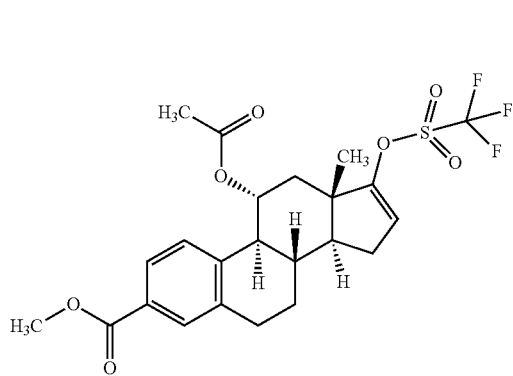

2.96 g (7.99 mmol) of methyl 11α-acetoxy-17-oxooestra-1,3,5(10)-triene-3-carboxylate were converted analogously to the preparation of Intermediate 1 to 5.13 g of the title compound as a crude product (still contained 2,6-di-tert-butylpyridine).

$^1$H NMR (300 MHz, DMSO-d$_6$): δ [ppm]=0.93 (s, 3H), 1.41-1.71 (m, 3H), 1.71-1.87 (m, 1H), 1.87-2.16 (m, 5H, includes s at 2.03 ppm), 2.16-2.40 (m, 2H), 2.67 (t, 1H), 2.74-2.93 (m, 2H), 3.79 (s, 3H), 5.34 (td, 1H), 5.75-5.82 (m, 1H), 7.03 (d, 1H), 7.67-7.75 (m, 2H).

Intermediate 9 methyl 11α-acetoxy-17-(5-fluoropyridin-3-yl)oestra-1,3,5(10),16-tetraene-3-carboxylate

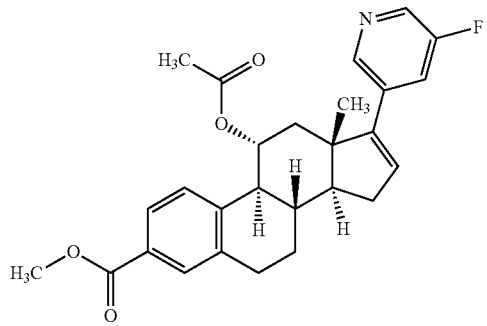

2.50 g (4.98 mmol) of methyl 11α-acetoxy-17-{[(trifluoromethyl)sulphonyl]oxy}oestra-1,3,5(10),16-tetraene-3-carboxylate were reacted with 981 mg (1.4 equiv.) of 5-fluoropyridine-3-boronic acid in the presence of 170 mg (5 mol %) of [1,3-bis(2,6-diisopropylphenyl)imidazol-2-ylidene](3-chloropyridyl)palladium(II) dichloride (PEPPSI™-IPr, CAS 905459-27-0) analogously to Intermediate 2-a at reflux temperature within 5 h. Yield: 2.62 g of the title compound as a crude product.

Intermediate 10 methyl 17-(5-fluoropyridin-3-yl)-11α-hydroxyoestra-1,3,5(10),16-tetraene-3-carboxylate

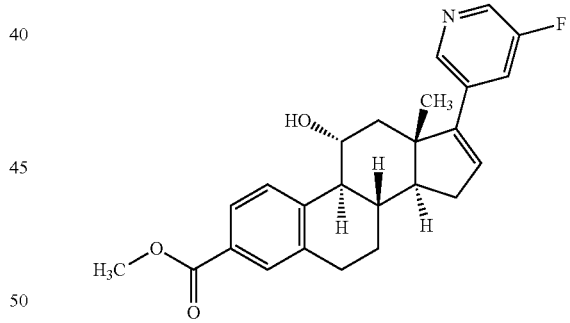

To 2.62 g (5.83 mmol) of methyl 11α-acetoxy-17-(5-fluoropyridin-3-yl)oestra-1,3,5(10),16-tetraene-3-carboxylate in 40 ml of methanol were added 4.0 g (5 equiv.) of potassium carbonate, and the mixture was stirred at room temp. for 3 h. Subsequently, the mixture was diluted with water and 1M hydrochloric acid and extracted three times with ethyl acetate. The combined organic phases were washed with water and saturated sodium chloride solution, dried over sodium sulphate and concentrated. After column chromatography on silica gel (hexane/ethyl acetate), the yield was 1.19 g (50% of theory) of the title compound.

$^1$H NMR (300 MHz, DMSO-d$_6$, selected signals): δ [ppm]=0.95 (s, 3H), 1.40-1.61 (m, 3H), 2.78-2.97 (m, 2H), 3.79 (s, 3H), 4.06-4.21 (m, 1H), 4.79-4.92 (m, 1H), 6.26 (br. s., 1H), 7.59-7.74 (m, 3H), 8.07 (d, 1H), 8.39-8.54 (m, 2H).

Intermediate 11 methyl 11β-fluoro-17-(5-fluoropyridin-3-yl)oestra-1,3,5(10),16-tetraene-3-carboxylate

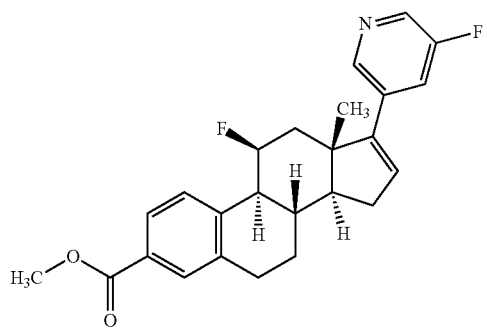

To an ice-cold solution of 531 mg (3.49 mmol) of methyl 17-(5-fluoropyridin-3-yl)-11α-hydroxyoestra-1,3,5(10),16-tetraene-3-carboxylate in 15 ml of THF were added dropwise 0.52 ml (1.65 equiv.) of 1,8-diazabicyclo[5.4.0]undec-7-ene and 0.58 ml (1.5 equiv.) of 1,1,2,2,3,3,4,4,4-nonafluorobutane-1-sulphonyl fluoride, and the mixture was stirred while being cooled with an ice bath for 3 h. Thereafter, the mixture was concentrated and purified by column chromatography on silica gel (hexane/ethyl acetate). The yield was 747 mg (84% of theory) of the title compound as a crude product.

$^1$H NMR (300 MHz, DMSO-$d_6$, selected signals): δ [ppm]=2.86-2.97 (m, 2H), 5.57-5.83 (m, 1H), 6.26-6.32 (m, 1H), 7.45-7.53 (m, 1H), 7.65-7.78 (m, 3H), 8.39-8.53 (m, 2H).

Intermediate 12

11β-fluoro-17-(5-fluoropyridin-3-yl)oestra-1,3,5(10),16-tetraene-3-carboxylic acid

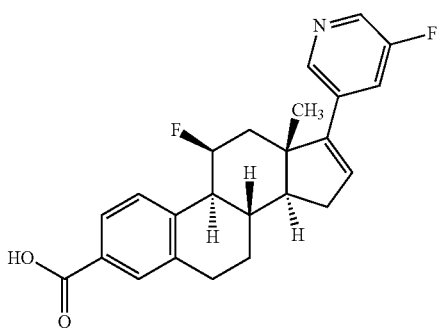

A mixture of 862 mg (2.11 mmol) of methyl 11β-fluoro-17-(5-fluoropyridin-3-yl)oestra-1,3,5(10),16-tetraene-3-carboxylate in 10 ml of THF was admixed with 5 ml of methanol and 442 mg of lithium hydroxide monohydrate in 5 ml of water, and the mixture was stirred at room temp. overnight. The reaction mixture was admixed with water and adjusted to pH=4 with 10% aqueous citric acid solution. The precipitated solid was filtered off with suction and washed with ethyl acetate and dried. Yield: 498 mg (60% of theory) of a white solid.

$^1$H NMR (500 MHz, DMSO-$d_6$): δ [ppm]=1.19 (s, 3H), 1.44-1.59 (m, 1H), 1.80-1.96 (m, 2H), 1.96-2.08 (m, 2H), 2.18-2.29 (m, 1H), 2.32-2.42 (m, 1H), 2.59 (td, 1H), 2.74 (dd, 1H), 2.77 (br. s., 1H), 2.86-3.00 (m, 2H), 5.66-5.80 (m, 1H), 6.32 (dd, 1H), 7.48 (d, 1H), 7.65-7.78 (m, 3H), 8.47 (d, 1H), 8.54 (t, 1H).

Intermediate 13

17-hydrazonooestra-1,3,5(10)-triene-3-carboxamide

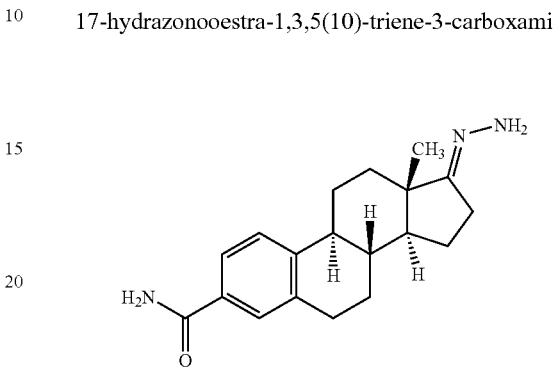

To 3.34 g (11.2 mmol) of 17-oxooestra-1,3,5(10)-triene-3-carboxamide (E. Morera, G. Ortar, T H L, 1998, 39, 2835-2838) in 70 ml of ethanol were added 3.65 g of hydrazine hydrate and 9 mg of hydrazine sulphate dissolved in 3 ml of water, and the mixture was stirred at room temp. for 4 days. Thereafter, it was poured onto 200 ml of ice-water and stirred for 40 min. Subsequently, the precipitate was filtered off with suction. Yield: after drying under reduced pressure, 3.07 g (88% of theory) of the title compound.

1H NMR (300 MHz, DMSO-d6): δ [ppm]=0.76 (s, 3H), 1.15-1.55 (m, 6H), 1.75-1.99 (m, 3H), 2.01-2.41 (m, 4H), 2.75-2.96 (m, 2H), 5.32 (br. s., 2H), 7.16 (br. s., 1H), 7.30 (d, 1H), 7.49-7.64 (m, 2H), 7.80 (br. s., 1H).

Intermediate 14

17-iodooestra-1,3,5(10),16-tetraene-3-carboxamide

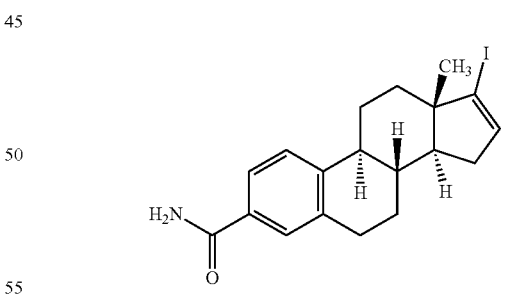

3.07 g (9.56 mmol) of 17-hydrazonooestra-1,3,5(10)-triene-3-carboxamide were initially charged in 65 ml of dioxane and 11 ml of triethylamine were added. Within 30 min, 10.0 g (4.0 equiv.) of iodine were added and the mixture was stirred at room temp. for 3 h. Then the mixture was poured onto 10% sodium sulphite solution and stirred for 40 min, and the precipitated solid was filtered off with suction and washed with water. 3.23 g of a brown solid (crude product) were obtained.

1H NMR (300 MHz, DMSO-d6, selected signals): δ [ppm]=0.67 (s, 3H), 1.81-1.91 (m, 1H), 1.94-2.09 (m, 1H), 2.12-2.35 (m), 2.79-2.95 (m, 2H), 6.18 (s, 1H), 7.18 (br. s., 1H), 7.29 (d, 1H), 7.48-7.63 (m, 2H), 7.81 (br. s., 1H).

Intermediate 15

3-cyanooestra-1,3,5(10),16-tetraen-17-yl trifluoromethanesulphonate

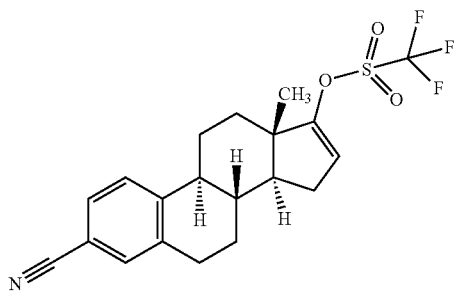

To a solution of 1.50 g (5.37 mmol) of 17-oxooestra-1,3,5(10)-triene-3-carbonitrile (Journal of the Chemical Society, 1964, 5889) in 34 ml of dichloromethane were added dropwise 2.4 ml of 2,6-di-tert-butylpyridine (2 equiv.) and 1.1 ml of trifluoromethanesulphonic anhydride. Thereafter, the mixture was stirred at room temp. for 22 h, poured cautiously onto 100 ml of saturated sodium hydrogencarbonate solution and stirred for 45 min, and the organic phases were removed. Thereafter, the aqueous phase was extracted twice with dichloromethane, and the combined organic phases were washed with saturated sodium hydrogencarbonate solution and saturated sodium chloride solution, dried over sodium sulphate and concentrated. The remaining solids were extracted by stirring with hexane. Yield: 1.51 g of the title compound as a crude product.

$^1$H NMR (300 MHz, CHLOROFORM-d): δ [ppm]=1.01 (s, 3H), 5.61-5.67 (m, 1H), 7.32-7.47 (m, 3H).

Intermediate 16-a 17-(5-fluoropyridin-3-yl)oestra-1,3,5(10),16-tetraene-3-carbonitrile

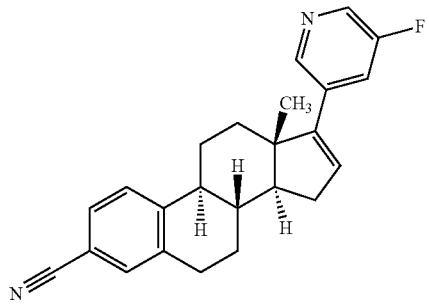

A mixture of 400 mg (0.97 mmol) of 3-cyanooestra-1,3,5(10),16-tetraen-17-yl trifluoromethanesulphonate, 192 mg (1.4 equiv.) of 5-fluoropyridine-3-boronic acid, 4 ml of toluene, 3 ml of ethanol, 82 mg of lithium chloride and 1.3 ml of 2M aqueous sodium carbonate solution was admixed with 56 mg of Pd(PPh$_3$)$_4$ and heated in a microwave at 120° C. for 60 min. Thereafter, the mixture was filtered through Celite, the organic phase was removed, the aqueous phase was extracted three times with ethyl acetate and the combined organic phases were washed with saturated sodium hydrogencarbonate solution and saturated sodium chloride solution, dried over sodium sulphate and concentrated. After column chromatography purification on silica gel, the yield was 162 mg (47% of theory) of a solid. C$_{24}$H$_{23}$FN$_2$ MS (ESIpos) mass found: 358.00.

$^1$H NMR (300 MHz, CHLOROFORM-d): δ [ppm]=1.06 (s, 3H), 1.43-1.90 (m), 1.96-2.10 (m, 1H), 2.11-2.28 (m, 2H), 2.31-2.53 (m, 3H), 2.95 (dd, 2H), 6.10 (br. s., 1H), 7.32-7.52 (m, 4H), 8.35 (d, 1H), 8.47 (s, 1H).

Intermediate 16-b 17-(pyrimidin-5-yl)oestra-1,3,5(10),16-tetraene-3-carbonitrile

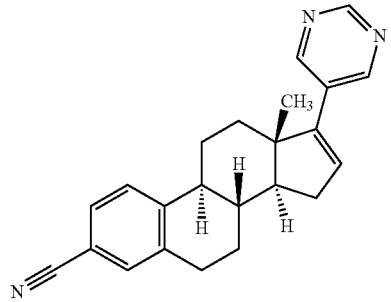

Analogously to the preparation of Intermediate 16-a, 400 mg (0.97 mmol) of 3-cyanooestra-1,3,5(10),16-tetraen-17-yl trifluoromethanesulphonate were reacted with 169 mg of pyrimidine-5-boronic acid. Yield: 101 mg of the title compound as a crude product. MS (ESIpos) mass found: 341.00.

$^1$H NMR (400 MHz, CHLOROFORM-d): δ [ppm]=6.11-6.20 (m, 1H), 8.72-8.80 (2H), 9.07-9.14 (1H).

EXAMPLE 1

17-(pyridin-3-yl)oestra-1,3,5(10),16-tetraene-3-carboxamide

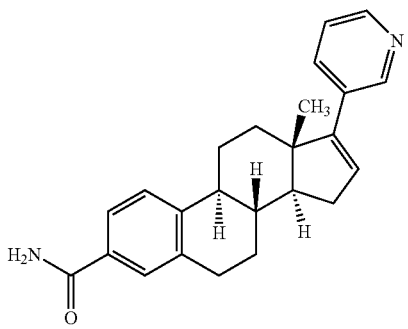

A mixture of 150 mg (0.37 mmol) of 17-iodooestra-1,3,5(10),16-tetraene-3-carboxamide, 63 mg (0.52 mmol) of pyridine-3-boronic acid, 31 mg of lithium chloride, 1.5 ml of toluene, 493 microliters of 2M sodium carbonate solution and 1 ml of ethanol was admixed with 13 mg of bis(triphenylphosphine)palladium(II) chloride and heated in a microwave at 120° C./100 watts for 90 min. Thereafter, the mixture was filtered, the phases were separated and the aqueous phase was extracted three times with ethyl acetate. The combined organic phases were washed with saturated sodium hydrogencarbonate solution and sodium chloride solution, dried over sodium sulphate and concentrated. After the residue had been purified by preparative HPLC (acetonitrile/water/formic acid), 9 mg of a solid were obtained. UPLC analysis (Method 1) Rt=0.94 min, mass found ESI(+) 358.20.

1H NMR (300 MHz, DMSO-d6, selected signals): δ [ppm]=0.99 (s, 3H), 1.38-1.78 (m, 6H), 1.91 (d, 1H), 2.02-2.20 (m, 2H), 2.87 (d, 2H), 6.12 (s., 1H), 7.19 (s., 1H), 7.25-7.38 (m, 2H), 7.50-7.64 (m, 2H), 7.70-7.97 (m, 2H), 8.42 (d, 1H), 8.59 (s, 1H).

EXAMPLE 2

17-(5-methoxypyridin-3-yl)oestra-1,3,5(10),16-tetraene-3-carboxamide

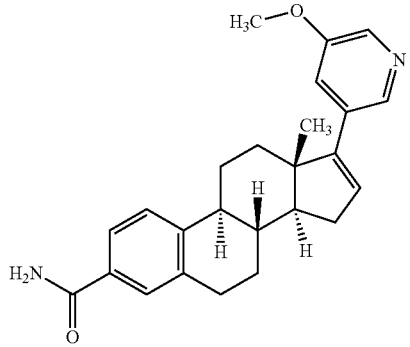

Analogously, 100 mg (0.24 mmol) of 17-iodooestra-1,3,5(10),16-tetraene-3-carboxamide and 53 mg (1.4 equiv.) of 5-methoxypyridine-3-boronic acid were converted using 14 mg of tetrakis(triphenylphosphine)palladium(0) as a catalyst to 7 mg of the title compound. UPLC analysis (Method 1) Rt=1.24 min, mass found ESI(+) 388.22.

1H NMR (400 MHz, DMSO-d6): δ [ppm]=0.99 (s, 3H), 1.37-1.67 (m, 4H), 1.74 (td, 1H), 1.85-1.97 (m, 1H), 2.04-2.18 (m, 2H), 2.20-2.37 (m, 2H), 2.79-2.97 (m, 2H), 3.82 (s, 3H), 6.16 (s., 1H), 7.16 (br. s., 1H), 7.20-7.33 (m, 2H), 7.52-7.62 (m, 2H), 7.80 (br. s., 1H), 8.16 (d, 1H), 8.20 (d, 1H).

EXAMPLE 3

17-[5-(trifluoromethyl)pyridin-3-yl]oestra-1,3,5(10),16-tetraene-3-carboxamide

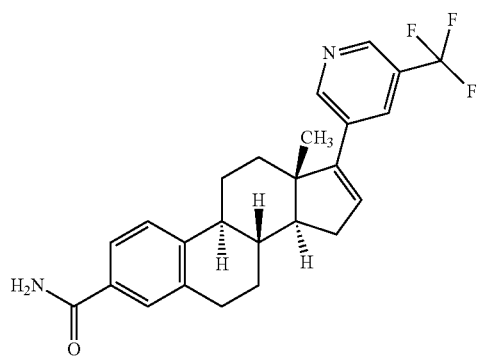

Analogously, 150 mg (0.37 mmol) of 17-iodooestra-1,3,5(10),16-tetraene-3-carboxamide and 141 mg (1.4 equiv.) of 3-(4,4,5,5-tetramethyl-1,3,2-dioxaborolan-2-yl)-5-(trifluoromethyl)pyridine were converted using 21 mg of tetrakis(triphenylphosphine)palladium(0) as a catalyst to 31 mg (20% of theory) of the title compound. UPLC analysis (Method 1) Rt=1.42 min, mass found ESI(+) 426.19.

$^1$H NMR (300 MHz, DMSO-$d_6$): δ [ppm]=1.01 (s, 3H), 1.38-1.68 (m), 1.75 (td, 1H), 1.84-1.96 (m, 1H), 2.07-2.20 (m, 2H), 2.22-2.44 (m), 2.79-3.01 (m, 2H), 6.36 (br. s., 1H), 7.19 (br. s., 1H), 7.27-7.34 (m, 1H), 7.52-7.66 (m, 2H), 7.82 (br. s., 1H), 8.04 (s, 1H), 8.83 (s, 1H), 8.87-8.95 (m, 1H).

EXAMPLE 4

17-(5-fluoropyridin-3-yl)oestra-1,3,5(10),16-tetraene-3-carboxamide

Preparation Method A

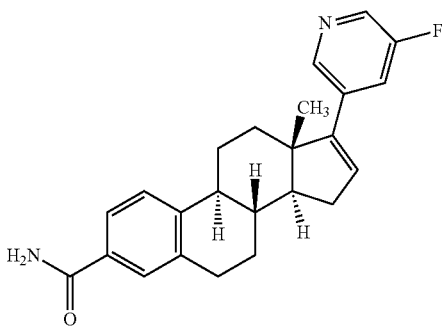

700 mg (1.85 mmol) of 17-(5-fluoropyridin-3-yl)oestra-1,3,5(10),16-tetraene-3-carboxylic acid were initially charged in 15 ml of 2-methyltetrahydrofuran and 2 ml of NMP, 1,1'-carbonyldiimidazole and imidazole hydrochloride were added thereto, and the mixture was stirred at room temp. for 18 h. Then 4.4 ml of 25% aqueous ammonia solution were added and the mixture was stirred at room temp. for 72 h. Thereafter, 1M hydrochloric acid, water and ethyl acetate were added and the mixture was stirred for 10 min. The solids were filtered off with suction and dried. Yield: 406 mg (58% of theory) of the title compound.

$^1$H NMR (300 MHz, DMSO-$d_6$): δ [ppm]=0.99 (s, 3H), 1.38-1.78 (m, 5H), 1.85-1.96 (m, 1H), 2.04-2.20 (m, 2H), 2.20-2.44 (m, 3H), 2.81-2.93 (m, 2H), 6.23-6.30 (m, 1H), 7.18 (br. s., 1H), 7.30 (d, 1H), 7.54-7.72 (m, 3H), 7.82 (br. s., 1H), 8.41-8.52 (m, 2H).

Preparation Method B

A mixture of 50 mg of 17-(5-fluoropyridin-3-yl)oestra-1,3,5(10),16-tetraene-3-carbonitrile in 3 ml of ethanol and 2 ml of water was admixed with 86 mg (4 equiv.) of sodium perborate tetrahydrate and the mixture was heated at 130° C. at 300 watts in a microwave for 30 min. 21 mg of sodium perborate tetrahydrate were added and the mixture was stirred at 130° C. at 300 watts for 15 min.

A further 98 mg of 17-(5-fluoropyridin-3-yl)oestra-1,3,5(10),16-tetraene-3-carbonitrile were heated in 5 ml of ethanol and 3 ml of water with 210 mg (5 equiv.) of sodium perborate tetrahydrate at 130° C. in a microwave for 30 min. The reaction mixtures were combined and extracted three times with tert-butyl methyl ether, washed with sodium chloride solution, dried over sodium sulphate and concentrated, and the residue was purified by preparative HPLC. Yield: 75 mg of the title compound.

EXAMPLE 5

17-(pyrimidin-5-yl)oestra-1,3,5(10),16-tetraene-3-carboxamide

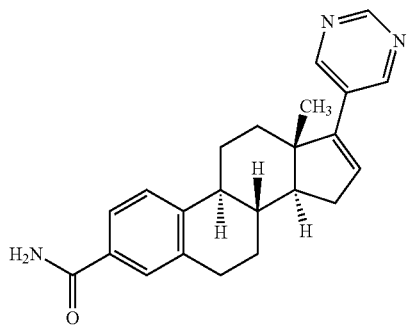

Analogously to the preparation of Example 6 (Preparation Method B), 88 mg of 17-(pyrimidin-5-yl)oestra-1,3,5(10), 16-tetraene-3-carbonitrile were reacted with sodium perborate at 140° C. and 300 watts in a microwave. After preparative HPLC, 11 mg of the title compound were obtained. $C_{23}H_{25}N_3O$ UPLC analysis (Method 1) Rt=1.14 min, mass found ESI(+) 359.20

$^1$H NMR (300 MHz, DMSO-d$_6$): δ [ppm]=0.99 (s, 3H), 1.35-1.80 (m, 5H), 1.85-1.96 (m, 1H), 2.07-2.20 (m, 2H), 2.26-2.44 (m, 3H), 2.82-2.93 (m, 2H), 6.28-6.33 (m, 1H), 7.18 (br. s., 1H), 7.30 (d, 1H), 7.55-7.62 (m, 2H), 7.82 (br. s., 1H), 8.83 (s, 2H), 9.04 (s, 1H).

EXAMPLE 6

17-(5-cyanopyridin-3-yl)oestra-1,3,5(10),16-tetraene-3-carboxamide

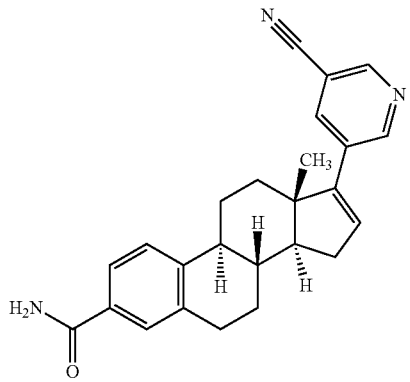

17 mg (0.044 mmol) of 17-(5-cyanopyridin-3-yl)oestra-1,3,5(10),16-tetraene-3-carboxylic acid were initially charged in 0.4 ml of 2-methyltetrahydrofuran. Then 11 mg of 1,1'-carbonyldiimidazole and 2 mg of 1H-imidazole hydrochloride were added thereto and the mixture was stirred at room temp. for 18 h. Then 79 μl of 33% ammonia solution were added and the mixture was stirred at room temp. for 72 h, admixed with 10 ml of 1M hydrochloric acid solution, extracted with ethyl acetate and concentrated, and the crude product was purified by preparative HPLC (acetonitrile/water/formic acid). Yield: 9 mg of the title compound.

$^1$H NMR (400 MHz, DMSO-d$_6$): δ [ppm]=1.00 (s, 3H), 1.35-1.50 (m, 1H), 1.50-1.68 (m, 3H), 1.73 (td, 1H), 1.85-1.98 (m, 1H), 2.07-2.23 (m, 2H), 2.25-2.36 (m, 2H), 2.36-2.44 (m, partly concealed by DMSO signal), 2.83-2.95 (m, 2H), 6.33-6.36 (m, 1H), 7.19 (br. s., 1H), 7.31 (d, 1H), 7.55-7.61 (m, 2H), 7.82 (br. s., 1H), 8.28 (t, 1H), 8.87 (dd, 2H).

EXAMPLE 7

11β-fluoro-17-(5-fluoropyridin-3-yl)oestra-1,3,5 (10),16-tetraene-3-carboxamide

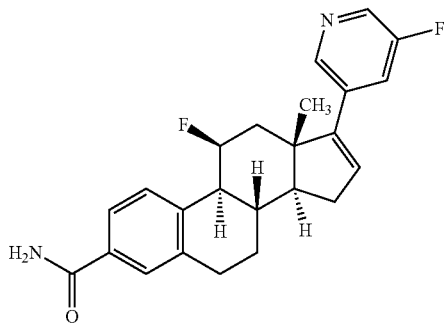

100 mg of (11beta)-11-fluoro-17-(5-fluoropyridin-3-yl) oestra-1,3,5(10),16-tetraene-3-carboxylic acid were initially charged in 3 ml of 2-methyltetrahydrofuran, then 62 mg (1.5 equiv.) of 1,1'-carbonyldiimidazole and 13 mg of imidazole hydrochloride were added and the mixture was stirred at room temp. for 18 h. Then 597 μl of 25% aqueous ammonia solution were added and the mixture was stirred at room temp. for 3 hours, admixed with 10 ml of 1M hydrochloric acid solution, extracted three times with ethyl acetate, concentrated and purified by preparative HPLC. Yield: 51 mg of the title compound. $C_{24}H_{24}F_2N_2O$ UPLC analysis (Method 1) Rt=1.22 mass found ESI(+) 394.19.

1H NMR (400 MHz, DMSO-d6): δ [ppm]=1.14 (s, 3H), 1.40-1.55 (m, 1H), 1.73-2.03 (m, 4H), 2.13-2.25 (m, 1H), 2.27-2.38 (m, 1H), 2.50-2.60 (m, 1H), 2.67 (dd, 1H), 2.80-2.97 (m, 2H), 5.60-5.81 (1H), 6.30 (br. s., 1H), 7.22 (br. s., 1H), 7.40 (d, 1H), 7.55-7.63 (m, 2H), 7.71 (dt, 1H), 7.85 (s, 1H), 8.45 (d, 1H), 8.48-8.55 (m, 1H).

EXAMPLE 8

11β-fluoro-17-(5-fluoropyridin-3-yl)-N-(2-sulphamoylethyl)oestra-1,3,5(10),16-tetraene-3-carboxamide

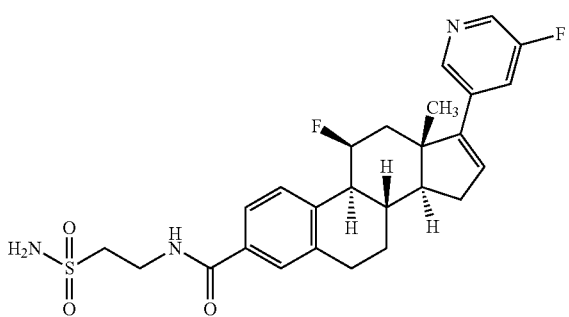

To a mixture of 100 mg of 11β-fluoro-17-(5-fluoropyridin-3-yl)oestra-1,3,5(10),16-tetraene-3-carboxylic acid and 81 mg (2 equiv.) of 2-aminoethane-1-sulphonamide hydrochloride in 0.5 ml of DMF and 3 ml of THF were added 39 mg of 1-hydroxy-1H-benzotriazole hydrate, 97 mg (2 equiv.) of N-[3-(dimethylamino)propyl]-N-ethylcarbodiimide hydrochloride (EDC) [CAS 25952-53-8] and 0.11 ml of triethylamine, and the mixture was stirred at room temp. for 18 h. After addition of water, the mixture was extracted three times with ethyl acetate, and the combined organic phases were concentrated and purified by preparative HPLC. Yield: 24 mg of the title compound. $C_{26}H_{29}F_2N_3O_3S$ UPLC analysis (Method 1) Rt=1.19 min, mass found ESI(+) 501.19.

$^1$H NMR (400 MHz, DMSO-$d_6$): δ [ppm]=1.14 (s, 3H), 1.48 (qd, 1H), 1.75-2.01 (m, 4H), 2.14-2.24 (m, 1H), 2.28-2.37 (m, 1H), 2.48-2.66 (m, 2H), 2.71-2.77 (m, 0.5H), 2.82-2.97 (m, 2H), 3.19 (dd, 2H), 3.56-3.63 (m, 2H), 5.64 (br. s, 0.5H), 5.76 (br. s., 0.5H), 6.28-6.32 (m, 1H), 6.91 (s, 2H), 7.43 (d, 1H), 7.53-7.59 (m, 2H), 7.69-7.74 (m, 1H), 8.43-8.53 (m, 3H).

EXAMPLE 9

17-(5-fluoropyridin-3-yl)-N-[(1S,2R)-2-hydroxycyclopentyl]oestra-1,3,5(10),16-tetraene-3-carboxamide

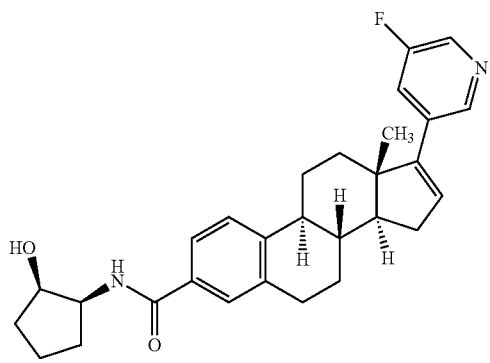

Analogously to Example 8, 100 mg of 17-(5-fluoropyridin-3-yl)oestra-1,3,5(10),16-tetraene-3-carboxylic acid were reacted with 73 mg of (1R,2S)-2-aminocyclopentan-1-ol hydrochloride (1:1) to give 75 mg of the title compound.

UPLC analysis (Method 1) Rt=1.40 min, mass found ESI(+) 460.25.

$^1$H NMR (300 MHz, DMSO-$d_6$): δ [ppm]=1.00 (s, 3H), 1.42-1.97 (m, 12H), 2.03-2.21 (m, 2H), 2.21-2.44 (m, 3H), 2.84-2.94 (m, 2H), 3.94-4.05 (m, 2H), 4.68 (d, 1H), 6.24-6.29 (m, 1H), 7.31 (d, 1H), 7.54-7.71 (m, 4H), 8.41-8.51 (m, 2H).

EXAMPLE 10

17-(5-fluoropyridin-3-yl)-N-[2-(hydroxymethyl)-2-methylpropyl]oestra-1,3,5(10),16-tetraene-3-carboxamide

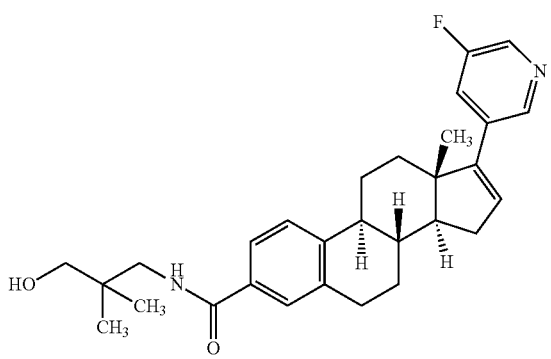

Analogously to Example 8, 100 mg of 17-(5-fluoropyridin-3-yl)oestra-1,3,5(10),16-tetraene-3-carboxylic acid were reacted with 55 mg of 3-amino-2,2-dimethylpropan-1-ol to give 53 mg of the title compound. After preparative purification by HPLC, the crude product was admixed with 1 ml of DMSO, and the remaining solids were filtered off with suction and rinsed three times with 0.5 ml each time of DMSO. The filtrate was admixed with water and saturated sodium hydrogencarbonate solution, and subsequently extracted with ethyl acetate. The combined organic phases were dried over sodium sulphate and concentrated. Yield: 54 mg of the title compound.

$^1$H NMR (400 MHz, DMSO-$d_6$): δ [ppm]=0.79 (s, 6H), 1.00 (s, 3H), 1.37-1.66 (m, 4H), 1.74 (td, 1H), 1.87-1.96 (m, 1H), 2.07-2.20 (m, 2H), 2.24-2.44 (m, 3H), 2.84-2.96 (m, 2H), 3.09 (dd, 4H), 4.59 (t, 1H), 6.27 (br. s., 1H), 7.32 (d, 1H), 7.52-7.59 (m, 2H), 7.68 (dt, 1H), 8.25 (t, 1H), 8.43 (d, 1H), 8.49 (s, 1H).

EXAMPLE 11

17-(5-fluoropyridin-3-yl)-N-[(1S,2S)-2-hydroxycyclopentyl]oestra-1,3,5(10),16-tetraene-3-carboxamide

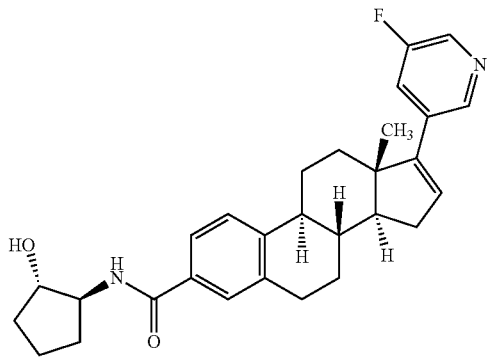

Analogously to Example 8, 100 mg of 17-(5-fluoropyridin-3-yl)oestra-1,3,5(10),16-tetraene-3-carboxylic acid were reacted with 72 mg of (1S,2S)-2-aminocyclopentan-1- ol hydrochloride (1:1) to give 79 mg of the title compound. $C_{29}H_{33}FN_2O_2$ UPLC analysis (Method 1) Rt=1.39 min, mass found ESI(+) 460.25.

$^1$H NMR (300 MHz, DMSO-d$_6$): δ [ppm]=0.99 (s, 3H), 1.32-2.02 (m, 13H), 2.05-2.20 (m, 2H), 2.24-2.43 (m, 3H), 2.50 (br. s., 1H), 2.83-2.93 (m, 2H), 3.25 (s, 1H), 3.89-3.99 (m, 2H), 4.70 (d, 1H), 6.24-6.29 (m, 1H), 7.30 (d, 1H), 7.51-7.60 (m, 2H), 7.67 (dt, 1H), 8.05 (d, 1H), 8.41-8.52 (m, 2H).

EXAMPLE 12

17-(5-fluoropyridin-3-yl)-N—[(R)-3-(hydroxymethyl)butyl]estra-1,3,5(10),16-tetraene-3-carboxamide

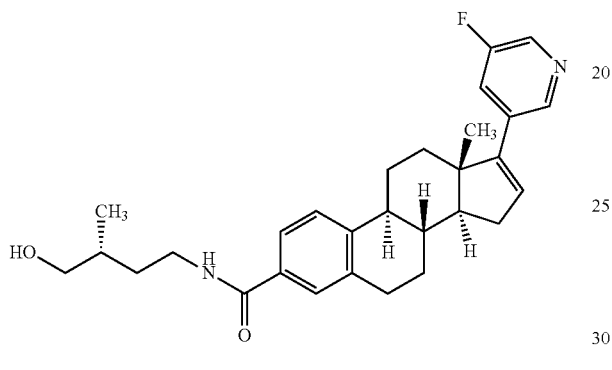

Analogously to Example 8, 100 mg of 17-(5-fluoropyridin-3-yl)oestra-1,3,5(10),16-tetraene-3-carboxylic acid were reacted with 55 mg of (2R)-4-amino-2-methylbutan-1-ol to give 70 mg of the title compound.

$C_{29}H_{35}FN_2O_2$ UPLC analysis (Method 1) Rt=1.38 min, mass found ESI(+) 462.27.

$^1$H NMR (300 MHz, DMSO-d$_6$): δ [ppm]=0.84 (d, 3H), 0.99 (s, 3H), 1.16-1.29 (m, 1H), 1.35-1.79 (m, 7H), 1.91 (d, 1H), 2.04-2.21 (m, 2H), 2.25-2.44 (m, 3H), 2.82-2.93 (m, 2H), 3.14-3.25 (m, 4H), 4.39 (t, 1H), 6.26 (br. s., 1H), 7.30 (d, 1H), 7.50-7.59 (m, 2H), 7.64-7.71 (dd, 1H), 8.24 (t, 1H), 8.41-8.52 (m, 2H).

EXAMPLE 13

17-(5-fluoropyridin-3-yl)-N-[1-(hydroxymethyl)cyclopentyl]oestra-1,3,5(10),16-tetraene-3-carboxamide

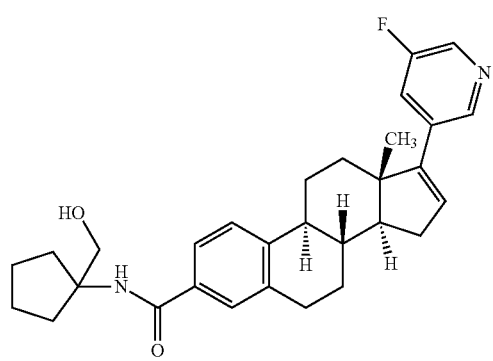

Analogously to Example 8, 100 mg of 17-(5-fluoropyridin-3-yl)oestra-1,3,5(10),16-tetraene-3-carboxylic acid were reacted with 61 mg of (1-aminocyclopentyl)methanol to give 34 mg of the title compound.

$C_{30}H_{35}FN_2O_2$ UPLC analysis (Method 1) Rt=1.50 min, mass found ESI(+) 474.27.

$^1$H NMR (300 MHz, DMSO-d$_6$): δ [ppm]=0.99 (s, 3H), 1.37-1.78 (m, 11H), 1.86-2.02 (m, 3H), 2.05-2.20 (m, 2H), 2.25-2.41 (m, 3H), 2.83-2.92 (m, 2H), 3.52 (d, 2H), 4.80 (t, 1H), 6.26 (br. s., 1H), 7.28 (d, 1H), 7.48-7.57 (d, 3H), 7.64-7.71 (m, 1H), 8.41-8.51 (m, 2H).

EXAMPLE 14

17-(5-fluoropyridin-3-yl)oestra-1,3,5(10),16-tetraen-3-yl 4-hydroxypiperidin-1-yl ketone

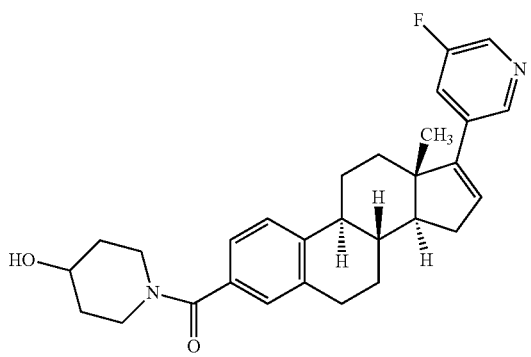

Analogously to Example 8, 100 mg of 17-(5-fluoropyridin-3-yl)oestra-1,3,5(10),16-tetraene-3-carboxylic acid were reacted with 54 mg of piperidin-4-ol to give 74 mg of the title compound.

UPLC analysis (Method 1) Rt=1.33 min, mass found ESI(+) 460.25.

$^1$H NMR (300 MHz, DMSO-d$_6$): δ [ppm]=1.00 (s, 3H), 1.18-1.97 (m, 10H), 2.03-2.43 (m, 5H), 2.79-2.92 (m, 2H), 3.03-3.19 (m, 2H), 3.53 (br. s., 1H), 3.62-3.75 (m, 1H), 3.94 (br. s., 1H), 4.72 (d, 1H), 6.26 (s, 1H), 6.99-7.13 (m, 2H), 7.29 (d, 1H), 7.63-7.71 (m, 1H), 8.39-8.53 (m, 2H).

EXAMPLE 15

17-(5-fluoropyridin-3-yl)-N—[(S)-1-(hydroxymethyl)propyl]oestra-1,3,5(10),16-tetraene-3-carboxamide

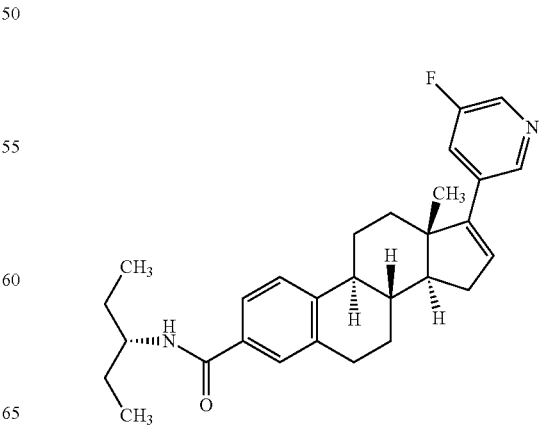

Analogously to Example 8, 100 mg of 17-(5-fluoropyridin-3-yl)oestra-1,3,5(10),16-tetraene-3-carboxylic acid were reacted with 47 mg of (2S)-2-aminobutan-1-ol to give 74 mg of the title compound.

$C_{28}H_{33}FN_2O_2$ UPLC analysis (Method 1) Rt=1.38 min, mass found ESI(+) 448.25.

$^1$H NMR (300 MHz, DMSO-$d_6$): δ [ppm]=0.82 (t, 3H), 0.99 (s, 3H), 1.31-1.80 (m, 7H), 1.85-1.97 (m, 1H), 2.05-2.43 (m, 5H), 2.82-2.94 (m, 2H), 3.31-3.46 (m, 1H), 3.74-3.89 (m, 1H), 4.59 (t, 1H), 6.27 (s, 1H), 7.30 (d, 1H), 7.53-7.61 (m, 2H), 7.64-7.71 (m, 1H), 7.81 (d, 1H), 8.39-8.53 (m, 2H).

EXAMPLE 16

17-(5-fluoropyridin-3-yl)-N—[(R)-1-(hydroxymethyl)-2-methylpropyl]oestra-1,3,5(10),16-tetraene-3-carboxamide

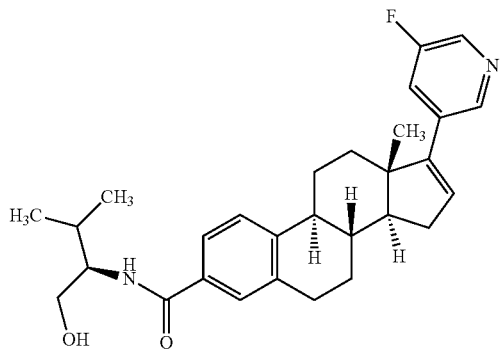

Analogously to Example 8, 100 mg of 17-(5-fluoropyridin-3-yl)oestra-1,3,5(10),16-tetraene-3-carboxylic acid were reacted with 55 mg of (2R)-2-amino-3-methylbutan-1-ol to give 78 mg of the title compound.

$C_{29}H_{35}FN_2O_2$ UPLC analysis (Method 1) Rt=1.43 min, mass found ESI(+) 462.27.

$^1$H NMR (300 MHz, DMSO-$d_6$): δ [ppm]=0.83 (d, 3H), 0.86 (d, 3H), 0.99 (s, 3H), 1.39-1.67 (m, 4H), 1.68-1.79 (m, 1H), 1.81-1.96 (m, 2H), 2.03-2.22 (m, 2H), 2.22-2.41 (m, 3H), 2.82-2.95 (m, 2H), 3.47 (t, 2H), 3.70-3.82 (m, 1H), 4.49 (t, 1H), 6.27 (br. s., 1H), 7.30 (d, 1H), 7.53-7.61 (m, 2H), 7.63-7.72 (m, 1H), 7.76 (d, 1H), 8.43 (d, 1H), 8.49 (s, 1H).

EXAMPLE 17

17-(5-fluoropyridin-3-yl)oestra-1,3,5(10),16-tetraen-3-yl (R)-3-hydroxypiperidin-1-yl ketone

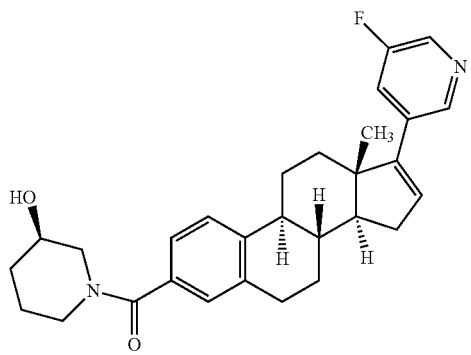

Analogously to Example 8, 100 mg of 17-(5-fluoropyridin-3-yl)oestra-1,3,5(10),16-tetraene-3-carboxylic acid were reacted with 73 mg of (3R)-piperidin-3-ol to give 75 mg of the title compound.

$C_{29}H_{33}FN_2O_2$ UPLC analysis (Method 1) Rt=1.37 min, mass found ESI(+) 460.25.

$^1$H NMR (300 MHz, DMSO-$d_6$): δ [ppm]=1.00 (s, 3H), 1.22-1.99 (m, 11H), 2.03-2.43 (m, 5H), 2.72-3.14 (4H, includes broad singlet at 3.02 ppm), 3.44 (broad singlet, 2H), 3.83 (broad singlet, 0.6H), 4.13 (broad singlet, 0.4H), 4.70-4.96 (broad signal, 0.9H), 6.26 (s., 1H), 7.01-7.13 (m, 2H), 7.29 (d, 1H), 7.63-7.72 (m, 1H), 8.39-8.53 (m, 2H).

EXAMPLE 18 rel-17-(5-fluoropyridin-3-yl)-N-[(1R,2R)-2-hydroxy-1-methylpropyl]oestra-1,3,5(10),16-tetraene-3-carboxamide

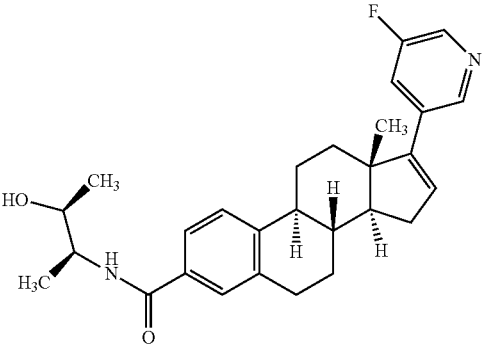

Analogously to Example 8, 100 mg of 17-(5-fluoropyridin-3-yl)oestra-1,3,5(10),16-tetraene-3-carboxylic acid were reacted with 67 mg of rel-(2S,3S)-2-amino-1-methylpropan-1-ol hydrochloride (1:1) to give 80 mg of the title compound.

$^1$H NMR (300 MHz, DMSO-$d_6$): δ [ppm]=0.91-1.03 (m, 6H), 1.06 (d, 3H), 1.35-1.80 (m, 5H), 1.85-1.97 (m, 1H), 2.03-2.42 (m, 5H), 2.81-2.94 (m, 2H), 3.59-3.69 (m, 1H), 3.85-3.99 (m, 1H), 4.56 (d, 1H), 6.27 (br. s., 1H), 7.30 (d, 1H), 7.50-7.61 (m, 2H), 7.64-7.80 (m, 2H), 8.39-8.53 (m, 2H).

EXAMPLE 19

17-(5-fluoropyridin-3-yl)-N-(2-hydroxyethyl)-N-isopropyloestra-1,3,5(10),16-tetraene-3-carboxamide

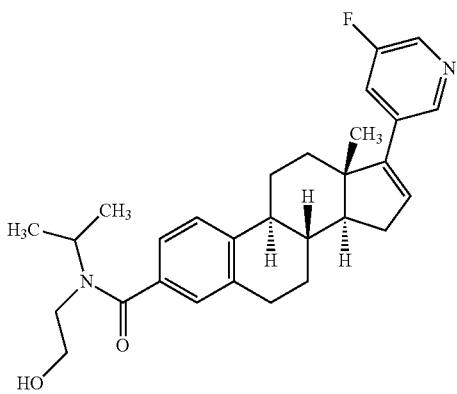

Analogously to Example 8, 100 mg of 17-(5-fluoropyridin-3-yl)oestra-1,3,5(10),16-tetraene-3-carboxylic acid were reacted with 55 mg of 2-(isopropylamino)ethan-1-ol to give 27 mg of the title compound.

¹H NMR (500 MHz, DMSO-d6): δ [ppm]=1.01-1.14 (m, 12H), 1.41-1.52 (m, 1H), 1.54-1.71 (m, 4H), 1.77 (td, 1H), 1.90-1.98 (m, 1H), 2.10-2.24 (m, 2H), 2.30-2.39 (m, 2H), 2.40-2.46 (m, 1H), 2.83-2.95 (m, 2H), 3.54 (br. s., 2H), 3.87 (br. s., 1H), 4.72 (br. s., 1H), 6.30 (dd, 1H), 7.03 (s, 1H), 7.07 (d, 1H), 7.32 (d, 1H), 7.70 (dt, 1H), 8.46 (d, 1H), 8.52 (t, 1H).

EXAMPLE 20

17-(5-fluoropyridin-3-yl)-N—[(RS)-3,3,3-trifluoro-2-hydroxypropyl]oestra-1,3,5(10),16-tetraene-3-carboxamide

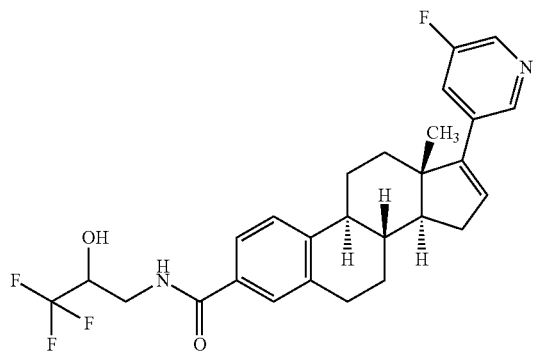

Analogously to Example 8, 250 mg of 17-(5-fluoropyridin-3-yl)oestra-1,3,5(10),16-tetraene-3-carboxylic acid were reacted with 171 mg of 2-amino-1-(trifluoromethyl)ethan-1-ol to give 161 mg of the title compound.

$C_{27}H_{28}F_4N_2O_2$ UPLC analysis (Method 1) Rt=1.45 min, mass found ESI(+) 488.21.

¹H NMR (300 MHz, DMSO-d₆): δ [ppm]=0.99 (s, 3H), 1.35-1.80 (m, 5H), 1.85-1.97 (m, 1H), 2.05-2.21 (m, 2H), 2.25-2.43 (m, 3H), 2.81-2.95 (m, 2H), 3.18-3.26 (m, 1H), 3.49-3.62 (m, 1H), 4.07-4.22 (m, 1H), 6.40-6.30 (m, 1H), 6.45 (d, 1H), 7.33 (d, 1H), 7.52-7.62 (m, 2H), 7.64-7.73 (m, 1H), 8.43 (d, 1H), 8.47-8.51 (m, 1H), 8.55 (t, 1H).

EXAMPLE 21

17-(5-fluoropyridin-3-yl)-N-[2-(1H-tetrazol-5-yl)ethyl]oestra-1,3,5(10),16-tetraene-3-carboxamide

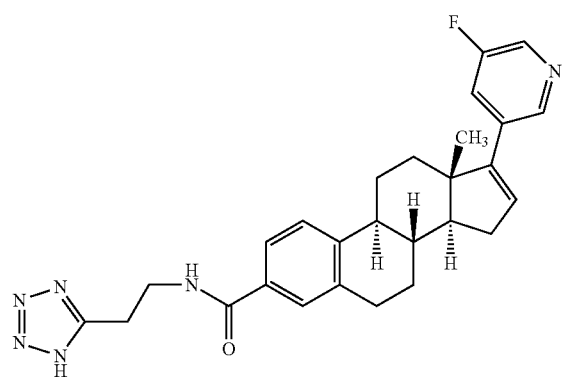

Analogously to Example 8, 100 mg of 17-(5-fluoropyridin-3-yl)oestra-1,3,5(10),16-tetraene-3-carboxylic acid were reacted with 60 mg of 2-(1H-tetrazol-5-yl)ethan-1-amine to give 4 mg of the title compound.

UPLC analysis (Method 1) Rt=1.27 min, mass found ESI(+) 472.24.

¹H NMR (300 MHz, DMSO-d₆): δ [ppm]=0.99 (m, 3H), 1.34-1.79 (m, 5H), 1.84-1.98 (m, 1H), 2.04-2.21 (m, 2H), 2.25-2.40 (m, 3H), 2.50 (s, 3H), 2.81-2.93 (m, 2H), 3.09 (t, 2H), 3.51-3.64 (m, 2H), 6.27 (s., 1H), 7.31 (d, 1H), 7.47-7.56 (m, 2H), 7.68 (dt, 1H), 8.39-8.54 (m, 3H).

EXAMPLE 22

17-(5-fluoropyridin-3-yl)-N-(1H-tetrazol-5-ylmethyl)oestra-1,3,5(10),16-tetraene-3-carboxamide

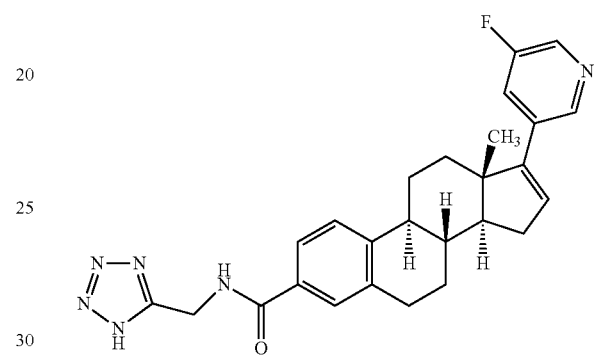

Analogously to Example 8, 100 mg of 17-(5-fluoropyridin-3-yl)oestra-1,3,5(10),16-tetraene-3-carboxylic acid were reacted with 53 mg of 1-(1H-tetrazol-5-yl)methylamine to give 14 mg of the title compound.

$C_{26}H_{27}FN_6O$ UPLC analysis (Method 1) Rt=1.27 min, mass found ESI(+) 458.22.

¹H NMR (400 MHz, DMSO-d₆): δ [ppm]=1.00 (s, 3H), 1.38-1.68 (m, 4H), 1.74 (td, 1H), 1.86-1.97 (m, 1H), 2.07-2.21 (m, 2H), 2.24-2.43 (m, 3H), 2.83-2.95 (m, 2H), 4.69 (d, 2H), 6.24-6.30 (m, 1H), 7.35 (d, 1H), 7.58-7.65 (m, 2H), 7.68 (dt, 1H), 8.43 (d, 1H), 8.49 (t, 1H), 9.05 (t, 1H).

EXAMPLE 23

17-(3-pyridyl)-N-(2-sulphamoylethyl)oestra-1,3,5(10),16-tetraene-3-carboxamide

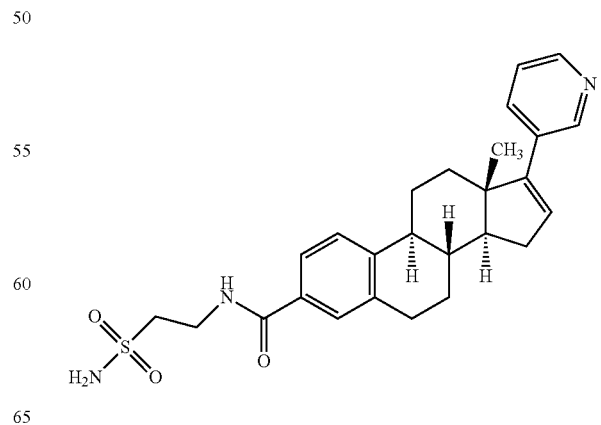

Analogously to Example 8, 100 mg of 17-(3-pyridyl)oestra-1,3,5(10),16-tetraene-3-carboxylic acid were reacted with 89 mg of 2-aminoethane-1-sulphonamide hydrochloride (1:1) to give 84 mg of the title compound.

UPLC analysis (Method 1) Rt=0.93 min, mass found ESI(+) 465.21.

$^1$H NMR (400 MHz, DMSO-d$_6$): δ [ppm]=0.99 (s, 3H), 1.37-1.67 (m, 4H), 1.73 (td, 1H), 1.86-1.96 (m, 1H), 2.05-2.17 (m, 2H), 2.24-2.44 (m, 3H), 2.82-2.96 (m, 2H), 3.14-3.23 (m, 2H), 3.54-3.66 (m, 2H), 6.12 (s, 1H), 6.91 (s, 2H), 7.29-7.36 (m, 2H), 7.51-7.59 (m, 2H), 7.77 (d, 1H), 8.39-8.45 (m, 1H), 8.48 (t, 1H), 8.58-8.61 (m, 1H).

EXAMPLE 24

N-(2-sulphamoylethyl)-17-[5-(trifluoromethyl)pyridin-3-yl]oestra-1,3,5(10),16-tetraene-3-carboxamide

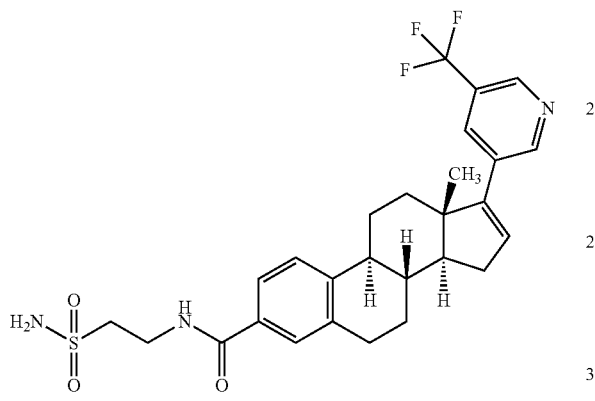

Analogously to Example 8, 70 mg of 17-[5-(trifluoromethyl)pyridin-3-yl]oestra-1,3,5(10),16-tetraene-3-carboxylic acid were reacted with 53 mg of 2-aminoethane-1-sulphonamide hydrochloride (1:1) to give 58 mg of the title compound.

$C_{27}H_{30}F_3N_3O_3S$ UPLC analysis (Method 1) Rt=1.39 min, mass found ESI(+) 533.20.

$^1$H NMR (400 MHz, DMSO-d$_6$): δ [ppm]=1.01 (s, 3H), 1.38-1.67 (m, 4H), 1.76 (td, 1H), 1.86-1.97 (m, 1H), 2.07-2.20 (m, 2H), 2.27-2.43 (m, 3H), 2.82-2.95 (m, 2H), 3.19 (dd, 2H), 3.53-3.65 (m, 2H), 6.35-6.38 (m, 1H), 6.91 (s, 2H), 7.33 (d, 1H), 7.51-7.57 (m, 2H), 8.04 (s, 1H), 8.48 (t, 1H), 8.82-8.85 (m, 1H), 8.90 (d, 1H).

EXAMPLE 25

N-[2-(N-methylsulphamoyl)ethyl]-17-[5-(trifluoromethyl)pyridin-3-yl]oestra-1,3,5(10),16-tetraene-3-carboxamide

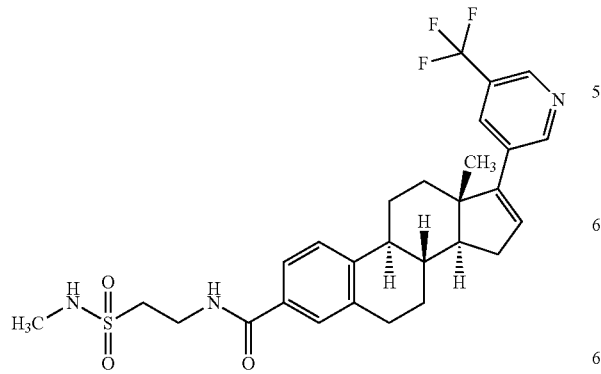

Analogously to Example 8, 70 mg of 17-[5-(trifluoromethyl)pyridin-3-yl]oestra-1,3,5(10),16-tetraene-3-carboxylic acid were reacted with 57 mg of 2-amino-N-methylethane-1-sulphonamide hydrochloride (1:1) to give 30 mg of the title compound.

$C_{28}H_{32}F_3N_3O_3S$ UPLC analysis (Method 1) Rt=1.45 min, mass found ESI(+) 547.21.

$^1$H NMR (400 MHz, DMSO-d$_6$): δ [ppm]=1.01 (s, 3H), 1.38-1.68 (m, 4H), 1.76 (td, 1H), 1.88-1.96 (m, 1H), 2.08-2.20 (m, 2H), 2.27-2.39 (m, 2H), 2.39-2.44 (m), 2.55 (s, 3H), 2.84-2.96 (m, 2H), 3.21 (dd, 2H), 3.51-3.58 (m, 2H), 6.34-6.38 (m, 1H), 6.97 (s, 1H), 7.33 (d, 1H), 7.51-7.58 (m, 2H), 8.02-8.05 (m, 1H), 8.46 (t, 1H), 8.82-8.85 (m, 1H), 8.90 (d, 1H).

EXAMPLE 26

N-(3-amino-3-oxopropyl)-17-(5-fluoropyridin-3-yl)oestra-1,3,5(10),16-tetraene-3-carboxamide

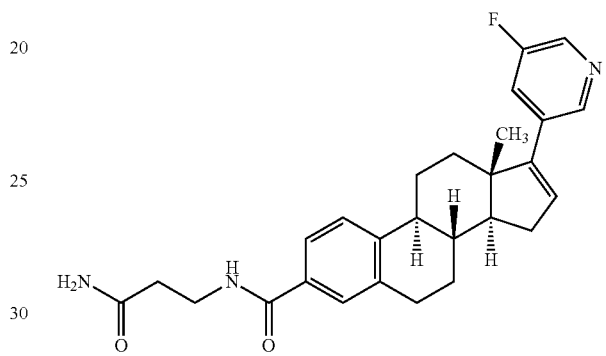

Analogously to Example 8, 100 mg of 17-(5-fluoropyridin-3-yl)oestra-1,3,5(10),16-tetraene-3-carboxylic acid were reacted with 66 mg of β-alaninamide to give 87 mg of the title compound.

$C_{27}H_{30}FN_3O_2$ UPLC analysis (Method 1) Rt=1.22 min, mass found ESI(+) 447.23.

$^1$H NMR (300 MHz, DMSO-d$_6$): δ [ppm]=0.99 (s, 3H), 1.34-1.80 (m, 5H), 1.84-1.96 (m, 1H), 2.06-2.44 (8H, includes triplet at 2.30 ppm), 2.82-2.93 (m, 2H), 3.32-3.43 (m, 2H), 6.27 (s, 1H), 6.79 (br. s., 1H), 7.25-7.37 (m, 2H), 7.50-7.58 (m, 2H), 7.65-7.72 (m, 1H), 8.34 (t, 1H), 8.43 (d, 1H), 8.47-8.50 (m, 1H).

EXAMPLE 27

17-(5-fluoropyridin-3-yl)-N-[3-(methylamino)-3-oxopropyl]oestra-1,3,5(10),16-tetraene-3-carboxamide

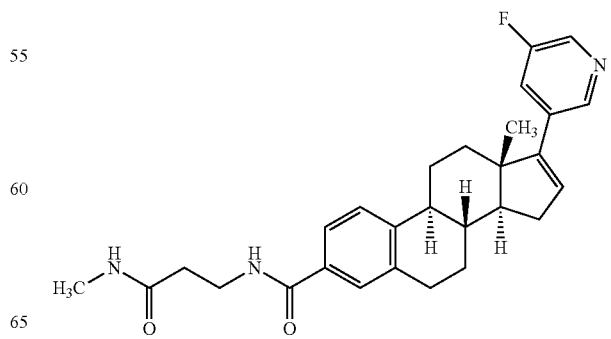

Analogously to Example 8, 100 mg of 17-(5-fluoropyridin-3-yl)oestra-1,3,5(10),16-tetraene-3-carboxylic acid were reacted with 73 mg of N-methyl-fl-alaninamide hydrochloride (1:1) to give 45 mg of the title compound.

$C_{28}H_{32}FN_3O_2$ UPLC analysis (Method 1) Rt=1.26 min, mass found ESI(+) 461.25.

$^1$H NMR (300 MHz, DMSO-d$_6$): δ [ppm]=0.99 (s, 3H), 1.34-1.80 (m, 5H), 1.85-1.96 (m, 1H), 2.05-2.43 (m, 7H), 2.53 (d, 3H), 2.80-2.96 (m, 2H), 3.33-3.45 (m, 2H), 6.27 (s, 1H), 7.31 (d, 1H), 7.49-7.59 (m, 2H), 7.68 (dt, 1H), 7.73-7.83 (m, 1H), 8.36 (t, 1H), 8.43 (d, 1H), 8.46-8.52 (m, 1H).

EXAMPLE 28

17-(5-fluoropyridin-3-yl)oestra-1,3,5(10),16-tetraen-3-yl (S)-2-(1H-tetrazol-5-yl)pyrrolidin-1-yl ketone

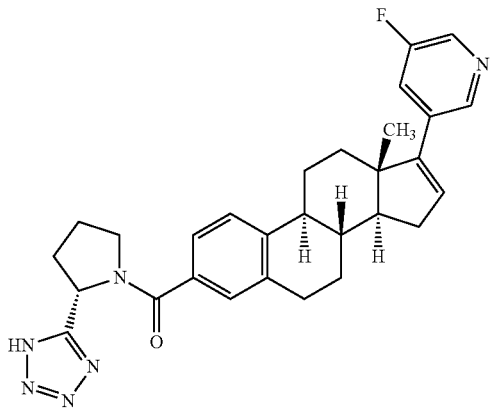

Analogously to Example 8, 100 mg of 17-(5-fluoropyridin-3-yl)oestra-1,3,5(10),16-tetraene-3-carboxylic acid were reacted with 74 mg of 5-[(2S)-pyrrolidin-2-yl]-1H-tetrazole to give 83 mg of the title compound.

UPLC analysis (Method 1) Rt=1.35 min, mass found ESI(+) 498.25.

$^1$H NMR (300 MHz, DMSO-d$_6$): δ [ppm]=1.00 (s, 3H), 1.35-2.42 (m), 2.78-2.96 (m, 2H), 3.44-3.59 (m, 1H), 3.62-3.75 (m, 1H), 5.19 (br. s., 0.1H), 5.32-5.49 (m, 0.9H), 6.27 (br. s., 1H), 6.68-6.92 (br. s., 0.2H), 7.01-7.20 (br. s., 0.2H), 7.20-7.43 (m, 2.6H), 7.63-7.75 (m, 1H), 8.40-8.55 (m, 2H).

EXAMPLE 29

1-{[17-(5-fluoropyridin-3-yl)oestra-1,3,5(10),16-tetraen-3-yl]carbonyl}-N-methyl-L-prolinamide

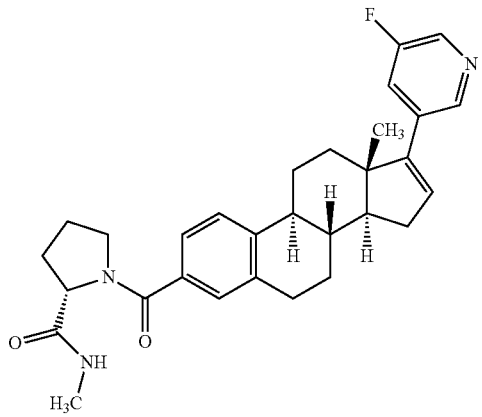

Analogously to Example 8, 100 mg of 17-(5-fluoropyridin-3-yl)oestra-1,3,5(10),16-tetraene-3-carboxylic acid were reacted with 68 mg of N-methyl-L-prolinamide to give 85 mg of the title compound.

UPLC analysis (Method 1) Rt=1.32 min, mass found ESI(+) 487.26.

$^1$H NMR (300 MHz, DMSO-d$_6$): δ [ppm]=1.00 (s, 3H), 1.32-2.42 (m, 15H), 2.58 (d, 3H), 2.75-2.95 (m, 2H), 3.32-3.62 (m), 4.00-4.08 (m), 4.29-4.39 (m), 6.23-6.32 (m, 1H), 6.96-7.06 (m, 0.5H), 7.21-7.36 (m, 2.5H), 7.64-7.82 (m, 2H), 8.43 (d, 1H), 8.47-8.51 (m, 1H).

EXAMPLE 30

1-{[17-(5-fluoropyridin-3-yl)oestra-1,3,5(10),16-tetraen-3-yl]carbonyl}-L-prolinamide

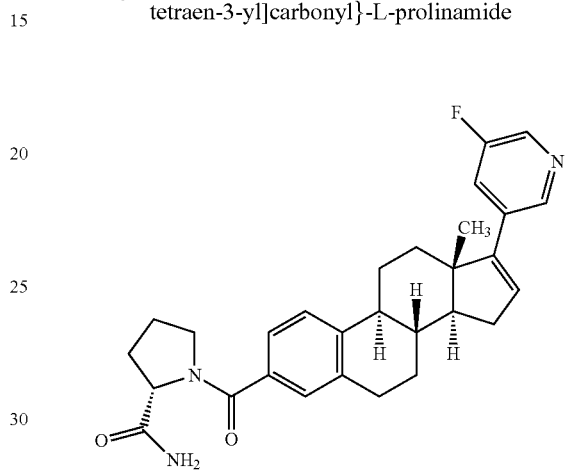

Analogously to Example 8, 100 mg of 17-(5-fluoropyridin-3-yl)oestra-1,3,5(10),16-tetraene-3-carboxylic acid were reacted with 60 mg of L-prolinamide to give 92 mg of the title compound.

UPLC analysis (Method 1) Rt=1.29 min, mass found ESI(+) 473.25.

$^1$H NMR (300 MHz, DMSO-d$_6$): δ [ppm]=1.00 (s, 3H), 1.33-1.96 (m, 9H), 2.00-2.42 (m), 2.77-2.94 (m, 2H), 3.31-3.42 (m), 3.43-3.62 (m), 4.07-4.16 (m, 0.3H), 4.26-4.36 (m, 0.7H), 6.27 (br. s., 1H), 6.85-7.00 (m, 1H), 7.02-7.12 (m, 0.5H), 7.20-7.40 (m, 3.5H), 7.68 (d, 1H), 8.43 (d, 1H), 8.49 (s, 1H).

EXAMPLE 31

17-(5-fluoropyridin-3-yl)-N-{2-methyl-2-[(methylsulphonyl)amino]propyl}oestra-1,3,5(10),16-tetraene-3-carboxamide

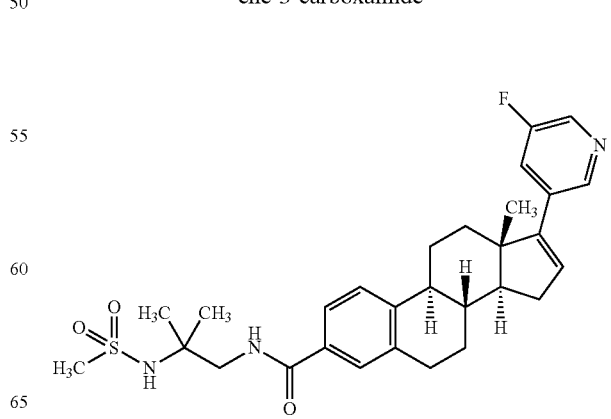

Analogously to Example 8, 100 mg of 17-(5-fluoropyridin-3-yl)oestra-1,3,5(10),16-tetraene-3-carboxylic acid were reacted with 107 mg of N-[1-(aminomethyl)-1-methylethyl]methanesulphonamide to give 95 mg of the title compound.

$C_{29}H_{36}FN_3O_3S$ UPLC analysis (Method 1) Rt=1.40 min, mass found ESI(+) 525.25.

$^1$H NMR (300 MHz, DMSO-$d_6$): δ [ppm]=1.00 (s, 3H), 1.23 (s, 6H), 1.39-1.79 (m, 5H), 1.85-1.97 (m, 1H), 2.05-2.41 (m, 5H), 2.84-2.99 (5H, includes singlet at 2.93 ppm), 3.34 (d, 2H), 6.27 (s, 1H), 6.93 (s, 1H), 7.34 (d, 1H), 7.53-7.61 (m, 2H), 7.68 (dt, 1H), 8.25 (t, 1H), 8.43 (d, 1H), 8.48-8.52 (m, 1H).

EXAMPLE 32

N-ethyl-17-(5-fluoropyridin-3-yl)-N-(2-hydroxyethyl)oestra-1,3,5(10),16-tetraene-3-carboxamide

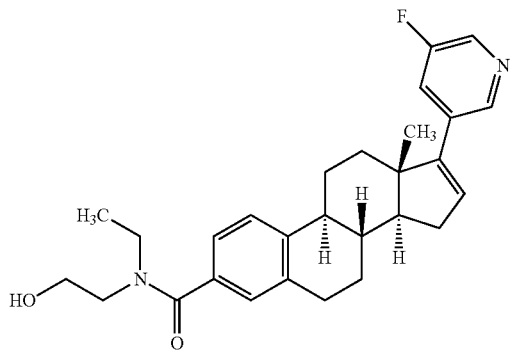

Analogously to Example 8, 100 mg of 17-(5-fluoropyridin-3-yl)oestra-1,3,5(10),16-tetraene-3-carboxylic acid were reacted with 47 mg of 2-(ethylamino)ethan-1-ol to give 75 mg of the title compound.

UPLC analysis (Method 1) Rt=1.38 min, mass found ESI(+) 448.25.

$^1$H NMR (400 MHz, DMSO-$d_6$): δ [ppm]=1.00 (s, 3H), 1.07 (br. s., 3H), 1.37-1.67 (m, 4H), 1.74 (td, 1H), 1.86-1.94 (m, 1H), 2.07-2.20 (m, 2H), 2.25-2.45 (m, 3H), 2.81-2.90 (m, 2H), 3.23 (br. s.), 3.42 (br. s.), 3.54 (br. s.), 4.71 (t, 1H), 6.24-6.29 (m, 1H), 7.00-7.11 (m, 2H), 7.28 (d, 1H), 7.65-7.71 (m, 1H), 8.43 (d, 1H), 8.49 (t, 1H).

EXAMPLE 33

N—[(S)-2,3-dihydroxypropyl]-17-(5-fluoropyridin-3-yl)oestra-1,3,5(10),16-tetraene-3-carboxamide

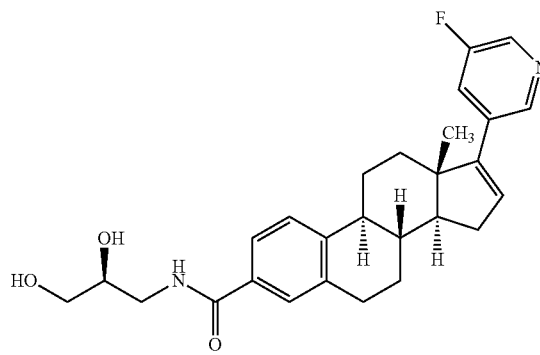

Analogously to Example 8, 100 mg of 17-(5-fluoropyridin-3-yl)oestra-1,3,5(10),16-tetraene-3-carboxylic acid were reacted with 58 mg of (2S)-3-aminopropane-1,2-diol to give 80 mg of the title compound.

UPLC analysis (Method 1) Rt=1.22 min, mass found ESI(+) 450.23.

$^1$H NMR (300 MHz, DMSO-$d_6$): δ [ppm]=0.99 (s, 3H), 1.34-1.79 (m, 5H), 1.85-1.96 (m, 1H), 2.05-2.44 (m, 5H), 2.82-2.97 (m, 2H), 3.09-3.23 (m, 1H), 3.23-3.40 (m, obscured by water signal), 3.53-3.63 (m, 1H), 4.53 (t, 1H), 4.76 (d, 1H), 6.27 (br. s., 1H), 7.31 (d, 1H), 7.53-7.62 (m, 2H), 7.68 (dt, 1H), 8.24 (t, 1H), 8.42-8.52 (m, 2H).

EXAMPLE 34

17-(5-fluoropyridin-3-yl)-N-(3-hydroxypropyl)-N-methyloestra-1,3,5(10),16-tetraene-3-carboxamide

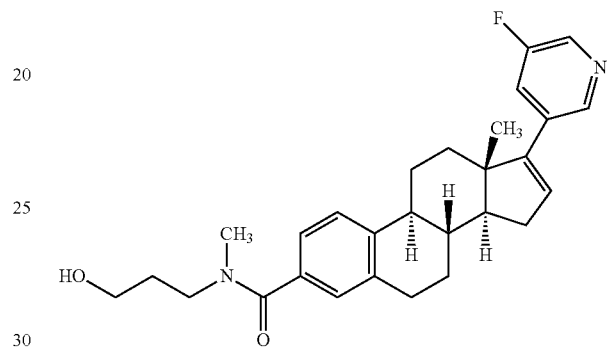

Analogously to Example 8, 100 mg of 17-(5-fluoropyridin-3-yl)oestra-1,3,5(10),16-tetraene-3-carboxylic acid were reacted with 47 mg of 3-(methylamino)propan-1-ol to give 83 mg of the title compound.

UPLC analysis (Method 1) Rt=1.34 min, mass found ESI(+) 448.25.

$^1$H NMR (400 MHz, DMSO-$d_6$): δ [ppm]=1.00 (s, 3H), 1.37-1.51 (m, 1H), 1.52-1.78 (m, 6H), 1.86-1.94 (m, 1H), 2.07-2.20 (m, 2H), 2.25-2.45 (m, 3H), 2.80-2.93 (m, 5H), 3.42 (br. s.), 4.42 (br. s., 1H), 6.27 (dd, 1H), 7.01-7.12 (m, 2H), 7.28 (d, 1H), 7.65-7.70 (m, 1H), 8.43 (d, 1H), 8.49 (t, 1H).

EXAMPLE 35

N—[(RS)-2,3-dihydroxypropyl]-17-(5-fluoropyridin-3-yl)-N-methyloestra-1,3,5(10),16-tetraene-3-carboxamide

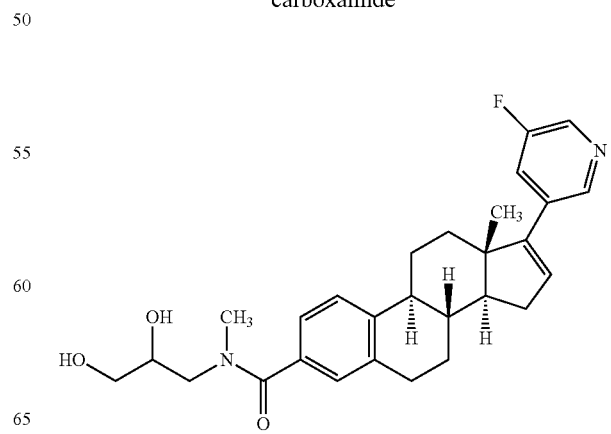

Analogously to Example 8, 100 mg of 17-(5-fluoropyridin-3-yl)oestra-1,3,5(10),16-tetraene-3-carboxylic acid were reacted with 56 mg of 3-(methylamino)propane-1,2-diol to give 68 mg of the title compound.

UPLC analysis (Method 1) Rt=1.25 min, mass found ESI(+) 464.25.

¹H NMR (400 MHz, DMSO-d₆): δ [ppm]=1.00 (s, 3H), 1.37-1.67 (m, 4H), 1.74 (td, 1H), 1.86-1.94 (m, 1H), 2.07-2.20 (m, 2H), 2.25-2.45 (m, 3H), 2.85 (br. s., 2H), 2.94 (s, 3H), 3.12 (br. s.), 3.23 (br. s.), 3.32 (br. s.), 3.51 (br. s.), 3.66 (br. s.), 3.75 (br. s.), 4.52 (br. s., 1H), 4.80 (br. s.), 4.86 (br. s.), 6.27 (br. s., 1H), 7.06-7.17 (m, 2H), 7.28 (br. s., 1H), 7.68 (dt, 1H), 8.43 (d, 1H), 8.47-8.51 (m, 1H).

EXAMPLE 36

N—[(R)-2,3-dihydroxypropyl]-17-(5-fluoropyridin-3-yl)oestra-1,3,5(10),16-tetraene-3-carboxamide

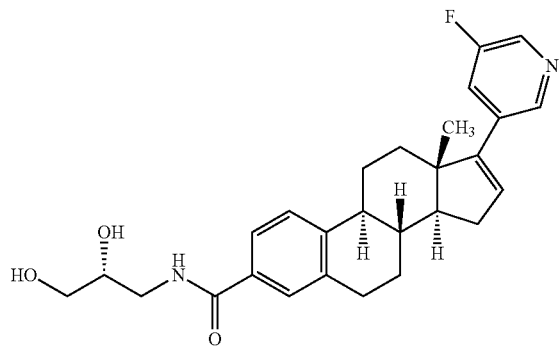

Analogously to Example 8, 100 mg of 17-(5-fluoropyridin-3-yl)oestra-1,3,5(10),16-tetraene-3-carboxylic acid were reacted with 48 mg of (2R)-3-aminopropane-1,2-diol to give 65 mg of the title compound.

UPLC analysis (Method 1) Rt=1.22 min, mass found ESI(+) 450.23.

¹H NMR (400 MHz, DMSO-d₆): δ [ppm]=1.00 (s, 3H), 1.38-1.66 (m, 4H), 1.74 (td, 1H), 1.87-1.95 (m, 1H), 2.08-2.19 (m, 2H), 2.26-2.45 (m, 3H), 2.84-2.93 (m, 2H), 3.12-3.20 (m, 1H), 3.25-3.37 (m, 3H), 3.55-3.62 (m, 1H), 4.51 (t, 1H), 4.75 (d, 1H), 6.27 (dd, 1H), 7.32 (d, 1H), 7.53-7.59 (m, 2H), 7.65-7.70 (m, 1H), 8.22 (t, 1H), 8.43 (d, 1H), 8.49 (t, 1H).

EXAMPLE 37

17-(5-fluoropyridin-3-yl)-N-[2-(methylsulphinyl)ethyl]oestra-1,3,5(10),16-tetraene-3-carboxamide

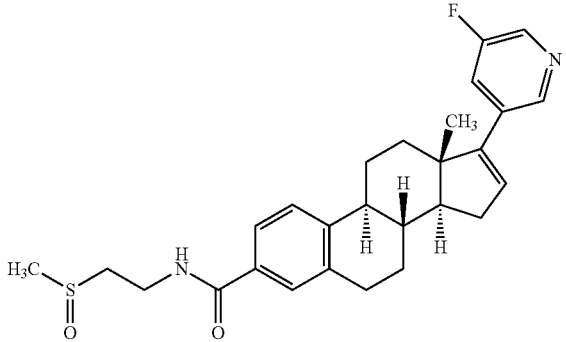

Analogously to Example 8, 100 mg of 17-(5-fluoropyridin-3-yl)oestra-1,3,5(10),16-tetraene-3-carboxylic acid were reacted with 57 mg of 2-(methylsulphinyl)ethan-1-amine to give 85 mg of the title compound.

UPLC analysis (Method 1) Rt=1.24 min, mass found ESI(+) 466.21.

¹H NMR (300 MHz, DMSO-d₆): δ [ppm]=1.00 (s, 3H), 1.35-1.80 (m, 5H), 1.86-1.96 (m, 1H), 2.06-2.41 (m, 6H), 2.55 (s, 3H), 2.78-2.92 (m, 3H), 2.92-3.06 (m, 1H), 3.47-3.67 (m, 2H), 6.24-6.30 (m, 1H), 7.33 (d, 1H), 7.52-7.59 (m, 2H), 7.64-7.71 (m, 1H), 8.41-8.51 (m, 2H), 8.59 (t, 1H).

EXAMPLE 38

17-(5-fluoropyridin-3-yl)-N—[(R)-2-hydroxypropyl]oestra-1,3,5(10),16-tetraene-3-carboxamide

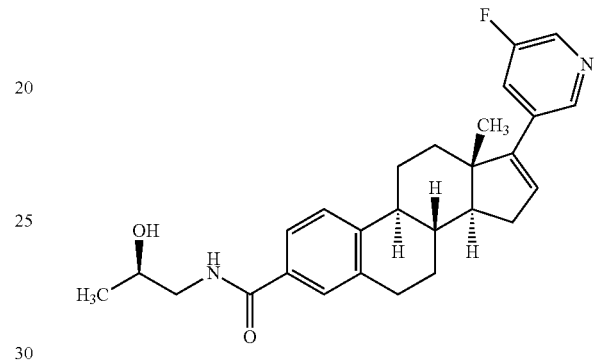

Analogously to Example 8, 100 mg of 17-(5-fluoropyridin-3-yl)oestra-1,3,5(10),16-tetraene-3-carboxylic acid were reacted with 40 mg of (2R)-1-aminopropan-2-ol to give 75 mg of the title compound.

UPLC analysis (Method 1) Rt=1.32 min, mass found ESI(+) 434.24.

¹H NMR (300 MHz, DMSO-d₆): δ [ppm]=0.95-1.07 (m, 6H), 1.35-1.81 (m, 5H), 1.86-1.96 (m, 1H), 2.06-2.44 (m, 5H), 2.50 (br. s., 1H), 2.83-2.93 (m, 2H), 3.15 (t, 2H), 3.68-3.79 (m, 1H), 4.67 (d, 1H), 6.23-6.29 (m, 1H), 7.31 (d, 1H), 7.52-7.60 (m, 2H), 7.67 (dt, 1H), 8.21 (t, 1H), 8.41-8.51 (m, 2H).

EXAMPLE 39

N-ethyl-17-(5-fluoropyridin-3-yl)oestra-1,3,5(10),16-tetraene-3-carboxamide

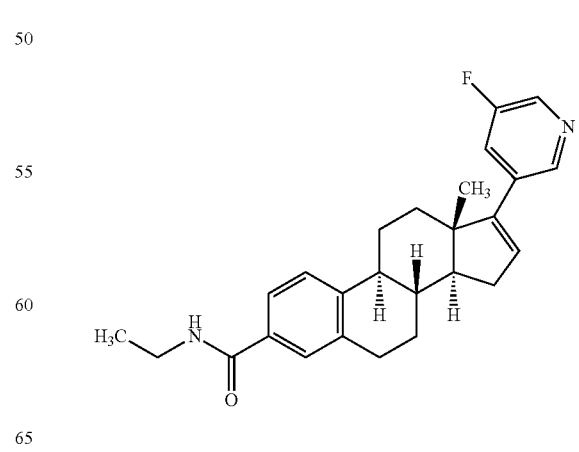

Analogously to Example 8, 100 mg of 17-(5-fluoropyridin-3-yl)oestra-1,3,5(10),16-tetraene-3-carboxylic acid were reacted with 43 mg of ethan-1-amine hydrochloride (1:1) to give 75 mg of the title compound.

UPLC analysis (Method 1) Rt=1.44 min, mass found ESI(+) 404.23.

$^1$H NMR (300 MHz, DMSO-d$_6$): δ [ppm]=0.99 (s, 3H), 1.07 (t, 3H), 1.35-1.79 (m, 5H), 1.86-1.96 (m, 1H), 2.06-2.44 (m, 5H), 2.82-2.93 (m, 2H), 3.17-3.26 (m), 6.23-6.29 (m, 1H), 7.30 (d, 1H), 7.50-7.58 (m, 2H), 7.64-7.71 (m, 1H), 8.28 (t, 1H), 8.41-8.51 (m, 2H).

EXAMPLE 40

17-(5-fluoropyridin-3-yl)-N—[(S)-1-(hydroxymethyl)ethyl]oestra-1,3,5(10),16-tetraene-3-carboxamide

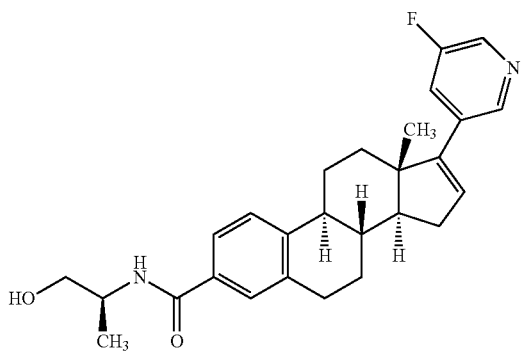

Analogously to Example 8, 100 mg of 17-(5-fluoropyridin-3-yl)oestra-1,3,5(10),16-tetraene-3-carboxylic acid were reacted with 40 mg of (2S)-2-aminopropan-1-ol to give 79 mg of the title compound.

UPLC analysis (Method 1) Rt=1.32 min, mass found ESI(+) 434.24.

$^1$H NMR (300 MHz, DMSO-d$_6$): δ [ppm]=1.00 (s, 3H), 1.08 (d, 3H), 1.35-1.67 (m, 4H), 1.74 (td, 1H), 1.86-1.96 (m, 1H), 2.06-2.20 (m, 2H), 2.25-2.44 (m, 3H), 2.83-2.93 (m, 2H), 3.23-3.33 (m, partly concealed by water signal), 3.37-3.46 (m, 1H), 3.88-4.04 (m, 1H), 4.64 (t, 1H), 6.22-6.30 (m, 1H), 7.30 (d, 1H), 7.51-7.60 (m, 2H), 7.67 (dt, 1H), 7.90 (d, 1H), 8.40-8.51 (m, 2H).

EXAMPLE 41

17-(5-fluoropyridin-3-yl)-N-(2-methoxyethyl)oestra-1,3,5(10),16-tetraene-3-carboxamide

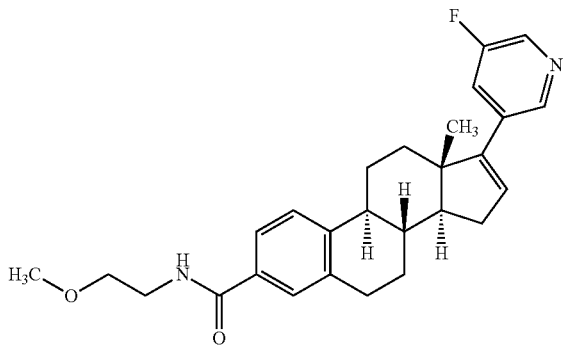

Analogously to Example 8, 100 mg of 17-(5-fluoropyridin-3-yl)oestra-1,3,5(10),16-tetraene-3-carboxylic acid were reacted with 40 mg of 2-methoxyethan-1-amine to give 77 mg of the title compound.

UPLC analysis (Method 1) Rt=1.41 min, mass found ESI(+) 434.24.

$^1$H NMR (300 MHz, DMSO-d$_6$): δ [ppm]=0.99 (s, 3H), 1.35-1.79 (m, 5H), 1.86-1.96 (m, 1H), 2.06-2.44 (m, 5H), 2.83-2.93 (m, 2H), 3.23 (s, 3H), 3.32-3.46 (m, 4H), 6.23-6.29 (m, 1H), 7.31 (d, 1H), 7.52-7.60 (m, 2H), 7.64-7.71 (m, 1H), 8.29-8.37 (m, 1H), 8.40-8.51 (m, 2H).

EXAMPLE 42

17-(5-fluoropyridin-3-yl)-N-[2-(isopropylsulphonyl)ethyl]oestra-1,3,5(10),16-tetraene-3-carboxamide

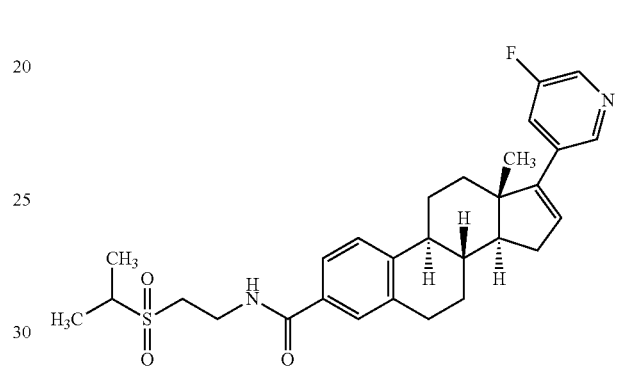

Analogously to Example 8, 100 mg of 17-(5-fluoropyridin-3-yl)oestra-1,3,5(10),16-tetraene-3-carboxylic acid were reacted with 80 mg of 2-(isopropylsulphonyl)ethan-1-amine to give 71 mg of the title compound.

$C_{29}H_{35}FN_2O_3S$ UPLC analysis (Method 1) Rt=1.40 min, mass found ESI(+) 510.24.

$^1$H NMR (300 MHz, DMSO-d$_6$): δ [ppm]=1.00 (s, 3H), 1.21 (d, 6H), 1.36-1.79 (m, 5H), 1.86-1.96 (m, 1H), 2.06-2.44 (m, 5H), 2.83-2.93 (m, 2H), 3.21-3.35 (m, partly concealed by water signal), 3.61 (q, 2H), 6.22-6.30 (m, 1H), 7.33 (d, 1H), 7.51-7.58 (m, 2H), 7.67 (dt, 1H), 8.39-8.51 (m, 2H), 8.55 (t, 1H).

EXAMPLE 43

17-(5-fluoropyridin-3-yl)-N-[(3-methyloxetan-3-yl)methyl]oestra-1,3,5(10),16-tetraene-3-carboxamide

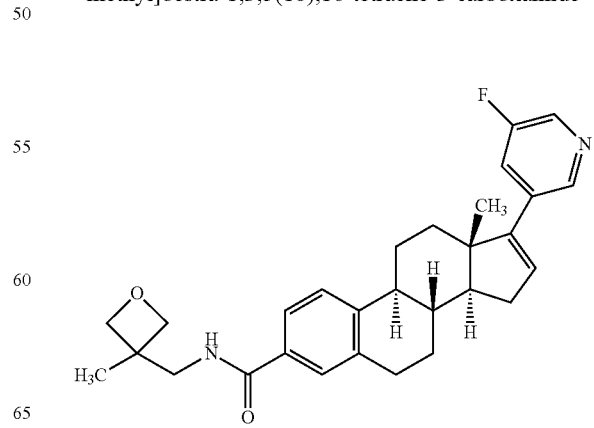

Analogously to Example 8, 100 mg of 17-(5-fluoropyridin-3-yl)oestra-1,3,5(10),16-tetraene-3-carboxylic acid were reacted with 54 mg of 1-(3-methyloxetan-3-yl)methylamine to give 69 mg of the title compound.

UPLC analysis (Method 1) Rt=1.40 min, mass found ESI(+) 460.25.

$^1$H NMR (300 MHz, DMSO-d$_6$): δ [ppm]=1.00 (s, 3H), 1.21 (s, 3H), 1.35-1.80 (m, 5H), 1.85-1.97 (m, 1H), 2.06-2.41 (m, 5H), 2.83-2.95 (m, 2H), 3.40 (d, 2H), 4.15 (d, 2H), 4.44 (d, 2H), 6.27 (br. s., 1H), 7.33 (d, 1H), 7.52-7.71 (m, 3H), 8.40-8.52 (m, 3H).

EXAMPLE 44

17-(5-fluoropyridin-3-yl)-N-(2-hydroxyethyl)-N-methyloestra-1,3,5(10),16-tetraene-3-carboxamide

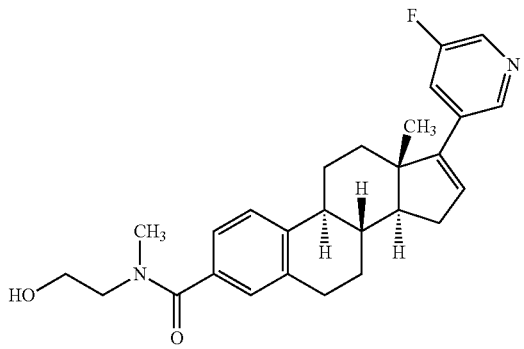

Analogously to Example 8, 100 mg of 17-(5-fluoropyridin-3-yl)oestra-1,3,5(10),16-tetraene-3-carboxylic acid were reacted with 40 mg of 2-(methylamino)ethan-1-ol to give 55 mg of the title compound.

UPLC analysis (Method 1) Rt=1.31 min, mass found ESI(+) 434.24.

$^1$H NMR (300 MHz, DMSO-d$_6$): δ [ppm]=1.00 (s, 3H), 1.34-1.80 (m, 5H), 1.84-1.95 (m, 1H), 2.05-2.42 (m, 5H), 2.79-2.97 (5H, includes s at 2.92 ppm), 3.45 (br. s.), 3.55 (br. s.), 4.71 (t, 1H), 6.21-6.31 (m, 1H), 7.03-7.15 (m, 2H), 7.28 (d, 1H), 7.68 (dt, 1H), 8.40-8.51 (m, 2H).

EXAMPLE 45

17-(5-fluoropyridin-3-yl)-N—[(S)-2-hydroxypropyl]oestra-1,3,5(10),16-tetraene-3-carboxamide

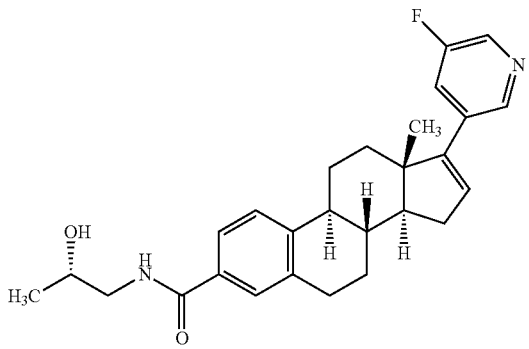

Analogously to Example 8, 100 mg of 17-(5-fluoropyridin-3-yl)oestra-1,3,5(10),16-tetraene-3-carboxylic acid were reacted with 40 mg of (S)-1-(aminomethyl)ethan-1-ol to give 92 mg of the title compound.

C$_{27}$H$_{31}$FN$_2$O$_2$ UPLC analysis (Method 1) Rt=1.32 min, mass found ESI(+) 434.24.

$^1$H NMR (300 MHz, DMSO-d$_6$): δ [ppm]=0.95-1.07 (m, 6H), 1.35-1.79 (m, 5H), 1.86-1.96 (m, 1H), 2.06-2.41 (m, 5H), 2.83-2.93 (m, 2H), 3.15 (t, 2H), 3.67-3.79 (m, 1H), 4.67 (d, 1H), 6.23-6.29 (m, 1H), 7.31 (d, 1H), 7.52-7.60 (m, 2H), 7.64-7.71 (m, 1H), 8.21 (t, 1H), 8.43 (d, 1H), 8.46-8.51 (m, 1H).

EXAMPLE 46

17-(5-fluoropyridin-3-yl)-N—[(S)-2-hydroxypropyl]oestra-1,3,5(10),16-tetraene-3-carboxamide

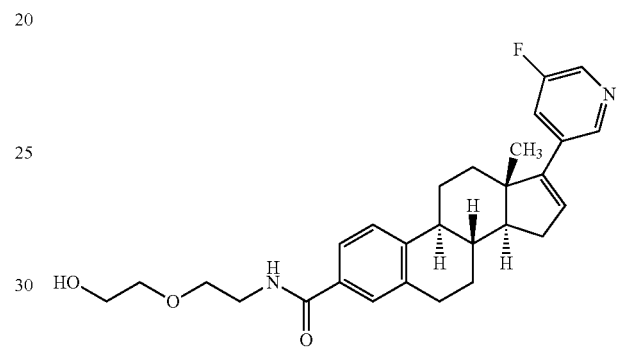

Analogously to Example 8, 100 mg of 17-(5-fluoropyridin-3-yl)oestra-1,3,5(10),16-tetraene-3-carboxylic acid were reacted with 56 mg of 2-(2-aminoethoxy)ethan-1-ol to give 64 mg of the title compound. C$_{28}$H$_{33}$FN$_2$O$_3$ UPLC analysis (Method 1) Rt=1.28 min, mass found ESI(+) 464.25.

$^1$H NMR (400 MHz, DMSO-d$_6$): δ [ppm]=1.00 (s, 3H), 1.37-1.66 (m, 4H), 1.74 (td, 1H), 1.87-1.95 (m, 1H), 2.08-2.19 (m, 2H), 2.26-2.45 (m, 3H), 2.84-2.92 (m, 2H), 3.29-3.52 (m, 8H), 4.54 (t, 1H), 6.25-6.28 (m, 1H), 7.31 (d, 1H), 7.52-7.59 (m, 2H), 7.65-7.70 (m, 1H), 8.32 (t, 1H), 8.43 (d, 1H), 8.49 (t, 1H).

EXAMPLE 47

17-(pyrimidin-5-yl)-N-(2-sulphamoylethyl)oestra-1,3,5(10),16-tetraene-3-carboxamide

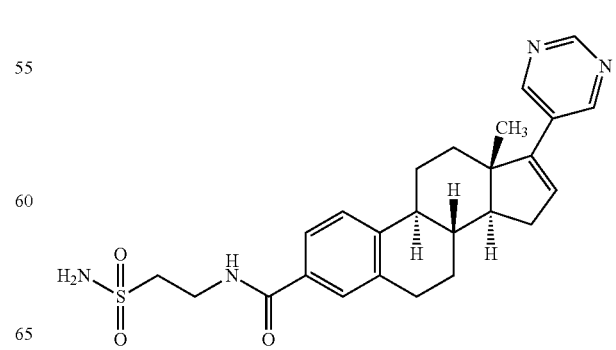

Analogously to Example 8, 100 mg of 17-(pyrimidin-5-yl)oestra-1,3,5(10),16-tetraene-3-carboxylic acid were reacted with 89 mg of 2-aminoethane-1-sulphonamide hydrochloride (1:1) to give 47 mg of the title compound. The title compound was purified by preparative HPLC.

| | |
|---|---|
| System: | Waters autopurification system: Pump 254, Sample Manager 2767, CFO, DAD 2996, ELSD 2424, SQD 3100 |
| Column: | XBridge C18 5 μm 100 × 30 mm |
| Solvent: | A = H2O + 0.2% by vol. of NH3 (32%) |
| | B = ACN |
| Gradient: | 0-8 min 15-60% B |
| Flow rate: | 50 ml/min |
| Temperature: | room temp. |
| Solution: | 126 mg/2.5 ml of DMSO |
| Injection: | 5 × 0.5 ml |
| Detection: | DAD scan range 210-400 nm |
| | MS ESI+, ESI−, scan range 160-1000 m/z |
| | ELSD |

| | Rt in min | Amount in mg |
|---|---|---|
| Fractions | 7.1-7.3 | 47 |
| Workup: | The fractions were concentrated by evaporation, admixed with tBuOH, frozen at −65° C. and then freeze-dried. | |

$^1$H NMR (300 MHz, DMSO-d$_6$): δ [ppm]=0.99 (s, 3H), 1.34-1.80 (m, 5H), 1.85-1.97 (m, 1H), 2.05-2.41 (m, 6H), 2.83-2.93 (m, 2H), 3.14-3.23 (m, 2H), 3.54-3.64 (m, 2H), 6.31 (s, 1H), 6.90 (s, 2H), 7.33 (d, 1H), 7.50-7.60 (m, 2H), 8.47 (t, 1H), 8.83 (s, 2H), 9.04 (s, 1H).

Pharmacological Study of the Inventive Compounds In Vitro

EXAMPLE 48

AKR1C3-Inhibitory Action

The AKR1C3-inhibitory action of the substances of this invention was measured in the AKR1C3 assay described in the paragraphs which follow.

Essentially, the enzyme activity is measured by quantifying the coumberol formed from coumberone (Halim, M., Yee, D. J., and Sames, D., J. AM. CHEM. SOC. 130, 14123-14128 (2008) and Yee, D. J., Balsanek, V., Bauman, D. R., Penning, T. M., and Sames, D., Proc. Natl. Acad. Sci. USA 103, 13304-13309 (2006)). In this assay, the increase in the highly fluorescent coumberol can be determined by NADPH (nicotinamide adenine dinucleotide phosphate)-dependent reduction of the nonfluorescent coumberone by AKR1C3.

The enzyme used was recombinant human AKR1C3 (aldo-keto reductase family 1 member C3) (GenBank Accession No. NM_003739). This was expressed as the GST (glutathione S-transferase) fusion protein in *E. coli* and purified by means of glutathione-Sepharose affinity chromatography. The GST was removed by thrombin digestion with subsequent size exclusion chromatography (Dufort, I., Rheault, P., Huang, X F., Soucy, P., and Luu-The, V., Endocrinology 140, 568-574 (1999)).

For the assay, 50 nl of a 100-fold concentrated solution of the test substance in DMSO were pipetted into a black low-volume 384-well microtitre plate (Greiner Bio-One, Frickenhausen, Germany), 2.0 μl of a solution of AKR1C3 in assay buffer [50 mM potassium phosphate buffer pH 7, 1 mM DTT, 0.0022% (w/v) Pluronic F-127, 0.01% BSA (w/v) and protease inhibitor cocktail (complete, EDTA-free Protease Inhibitor Cocktail from Roche)] were added and the mixture was incubated for 15 min, in order to enable preliminary binding of the substances to the enzyme prior to the enzyme reaction. Then the enzyme reaction was started by adding 3 μl of a solution of NADPH (16.7 μM→final concentration in assay volume 5 μl is 10 μM) and coumberone (0.5 μM→final concentration in assay volume 5 μl is 0.3 μM) in assay buffer and the resulting mixture was incubated at 22° C. for the reaction time of 90 min. The concentration of the AKR1C3 was matched to the respective activity of the enzyme preparation and set such that the assay worked within the linear range. Typical concentrations were in the region of 1 nM. The reaction was stopped by adding 5 μl of a stop solution consisting of the inhibitor EM-1404 [F. Labrie et al. U.S. Pat. No. 6,541,463, 2003](2 μM→final concentration in assay volume 5 μl is 1 μM). Subsequently, the fluorescence of coumberol was measured at 520 nm (excitation at 380 nm) with a suitable measuring instrument (Pherastar from BMG Labtechnologies). The intensity of the fluorescence was used as a measure for the amount of coumberol formed and hence for the enzyme activity of AKR1C3. The data were normalized (enzyme reaction without inhibitor=0% inhibition; all other assay components but no enzyme=100% inhibition). Typically, the test substances were tested on the same microtitre plate at 11 different concentrations in the range from 20 μM to 96.8 μM (20 μM, 5.9 μM, 1.7 μM, 0.5 μM, 0.15 μM, 44 nM, 12.9 nM, 3.8 nM, 1.1 nM, 0.3 nM and 96.8 μM; the dilution series were prepared before the assay at the level of the 100-fold concentrated solution by serial 1:3 dilutions with 100% DMSO) in twin values for each concentration, and IC$_{50}$ values were calculated by a 4-parameter fit.

As described, the pharmacological substances claimed were tested for their inhibitory effect on the AKR1C3 enzyme (see Table 1). The compounds claimed show strong inhibition of AKR1C3 in vitro (IC$_{50}$ values <500 nM) and predominantly even IC$_{50}$ values <100 nM.

TABLE 1

Inhibition of AKR1C3 by the inventive compounds (for some of the compounds, the values for two experimental determinations are reported)

| Example compound | AKR1C3 enzyme inhibition IC$_{50}$ [nmol/l] |
|---|---|
| 1 | 6 |
| 1 | 5 |
| 2 | 189 |
| 2 | 100 |
| 3 | 46 |
| 3 | 25 |
| 4 | 4 |
| 4 | 4 |
| 5 | 313 |
| 5 | 199 |
| 5 | 143 |
| 6 | 346 |
| 7 | 27 |
| 7 | 27 |
| 8 | 73 |
| 9 | 61 |
| 9 | 81 |
| 10 | 97 |
| 10 | 46 |
| 11 | 34 |
| 11 | 20 |
| 12 | 21 |
| 12 | 20 |
| 13 | 108 |
| 13 | 79 |
| 14 | 54 |
| 14 | 37 |
| 15 | 25 |
| 15 | 25 |

TABLE 1-continued

Inhibition of AKR1C3 by the inventive compounds (for some of the compounds, the values for two experimental determinations are reported)

| Example compound | AKR1C3 enzyme inhibition IC$_{50}$ [nmol/l] |
|---|---|
| 16 | 15 |
| 16 | 42 |
| 17 | 29 |
| 17 | 20 |
| 18 | 45 |
| 18 | 35 |
| 19 | 60 |
| 19 | 48 |
| 20 | 12 |
| 20 | 8 |
| 20 | 20 |
| 20 | 16 |
| 21 | 5 |
| 22 | 5 |
| 23 | 9 |
| 24 | 17 |
| 25 | 48 |
| 26 | 5 |
| 27 | 5 |
| 28 | 9 |
| 29 | 10 |
| 30 | 12 |
| 31 | 19 |
| 32 | 11 |
| 33 | 4 |
| 33 | 5 |
| 34 | 6 |
| 35 | 17 |
| 36 | 6 |
| 37 | 5 |
| 38 | 4 |
| 39 | 5 |
| 41 | 8 |
| 42 | 11 |
| 43 | 7 |
| 44 | 12 |
| 45 | 6 |
| 46 | 6 |
| 47 | 119 |

EXAMPLE 49

Test of AKR1C3 Inhibition in a Cell-Based System

The inhibition of AKR1C3 by the substances described in this invention was measured in a cell-based assay using coumberol as the substrate for the AKR1C3 (Halim, M., Yee, D. J., and Sames, D., J. AM. CHEM. SOC. 130, 14123-14128 (2008) and Yee, D. J., Balsanek, V., Bauman, D. R., Penning, T. M., and Sames, D., Proc. Natl. Acad. Sci. USA 103, 13304-13309 (2006)) (cf. Example 48).

The cell system used was HEK293 cells (ATCC, USA) (cell culture medium: DMEM, 1.5 g of glucose, 10% FCS, PSG). The cells were transfected with an AKR1C3 expression plasmid (pCMV6-AC-AKR1C3, GenBank Accession No. NM_003739.4) overnight (X-tremeGENE HP, Roche). The next morning, the cells were sown into black 96-well culture plates with a cell density of 40 000 cells/well (Greiner Bio-One, Frickenhausen, Germany). 7 h later, the cells were incubated with the test substances (dissolved in 100× concentration in DMSO, final concentration between $10^{-11}$ M and $10^{-5}$ M) and coumberol (dissolved in cell culture medium, final concentration $5\times10^{-6}$ M) overnight. The following morning, the fluorescence of coumberol was measured at 535 nm (excitation at 355 nm) with a suitable measuring instrument (Mithras, from Berthold). The intensity of the fluorescence was used as a measure for the amount of coumberol formed and hence for the enzyme activity of AKR1C3. The data were normalized (transfected cells without inhibitor, only DMSO=0% inhibition; transfected cells, 10 µM EM-1404 inhibitor [F. Labrie et al. U.S. Pat. No. 6,541,463, 2003]=100% inhibition) and IC$_{50}$ values were calculated by a 4-parameter fit.

The pharmacological substances claimed were tested for their inhibitory action on the AKR1C3 enzyme by means of the cell-based assay described above (see Table 2). The compounds exhibited strong inhibition of cellular AKR1C3 in vitro (IC$_{50}$ values <100 nM).

TABLE 2

Inhibition of AKR1C3 of the inventive compounds in a cellular assay (the values reported are for at least two experimental determinations)

| Example compound | Cellular AKR1C3 inhibition IC50 [nmol/l] |
|---|---|
| 1 | 13 |
| 1 | 27 |
| 1 | 28 |
| 1 | 66 |
| 7 | 83 |
| 7 | 150 |
| 12 | 68 |
| 12 | 96 |
| 12 | 43 |
| 12 | 23 |
| 16 | 97 |
| 16 | 74 |
| 17 | 34 |
| 17 | 28 |
| 20 | 32 |
| 20 | 42 |

EXAMPLE 50

Inhibition of Cyp17A1

CYP17A1 (synonym: 17α-hydroxylase/17,20 lyase) is an enzyme which adds a hydroxyl group on at position 17 in the steroidal D ring of pregnenolone and of progesterone, which forms 17α-hydroxyprogesterone and 17α-hydroxypregnenolone. Subsequently, dehydroepiandrosterone and androstenedione are formed. The known CYP17A1 inhibitor abiraterone is used, for example, for the treatment of metastasized, castration-refractory prostate carcinoma after failure of docetaxel-based chemotherapy (Urologe 2010, 49, 64-68). Abiraterone blocks androgen synthesis and oestrogen synthesis in the whole body and accordingly lowers hormone production in a non-tissue-specific manner, which leads to undesirable side effects (cf. press release from FDA, U.S. Food and Drug Admistration dated 28 Apr. 2011).

It has been found that, surprisingly, the inventive compounds, even though they exhibit an aromatic nitrogen-containing heterocycle at position 17 of the steroidal skeleton, inhibit CYP17A1 only very weakly, if at all.

Assay Description:

The inhibition of CYP17A1 by the test compounds was evaluated by means of recombinant enzyme. Human CYP17A1 was expressed in E. coli (Ehmer, P. B. et al.; J. Steroid Biochem. Mol. Biol., 75, 57-63 (2000)). The microsomal fraction and 140 µL phosphate buffer (50 mM Na phosphate, 1 mM MgCl$_2$, 0.1 mM EDTA, 0.1 mM dithiothreitol, pH 7.4) together with a mixture of progesterone (24.95 μM) and $^3$H-progesterone (0.05 μM, 101.3 Ci/mmol), 50 μM of an NADPH regeneration system (in phosphate buffer with 10 mM NADP+, 100 mM glucose 6-phosphate and 2.5 U glucose 6-phosphate dehydrogenase) and the corresponding test substances (in 5 μl of DMSO) were preincubated individually at 37° C. for 5 minutes. The reaction was started by adding the enzyme and, after incubation at 37° C. for 30 minutes, stopped by adding 50 μl of 1 N hydrochloric acid.

The steroids were extracted with ethyl acetate. After evaporating the organic phase, the steroids were taken up in acetonitrile. 16α-Hydroxyprogesterone, 17α-hydroxyprogesterone and progesterone were separated with acetonitrile/water (45:55) as mobile phase on a C18 reverse phase chromatography column (Nucleodur C18 Gravity, 3 μm, Macherey-Nagel, Düren) in an HPLC System (Agilent 1100 Series, Agilent Technologies, Waldbronn). Detection and quantification of the steroids were conducted by means of a Radioflow detector (Berthold Technologies, Bad Wildbad). The inhibition was calculated by the following formula:

$$\% \text{ Inhibition} = \frac{\%(17\alpha-\text{hydroxyprogesterone} + 16\alpha-\text{hydroxyprogesterone})}{\%(17\alpha-\text{hydroxyprogesterone} + 16\alpha-\text{hydroxyprogesterone}) + \text{progesterone}} \cdot 100$$

Each value was calculated from at least three independent experiments. The final $IC_{50}$ value was calculated as the mean from 3 or 4 independent $IC_{50}$ values.

The inventive compounds do not show any inhibition of Cyp17A1 (Table 3); in contrast, the known Cyp17A1 Inhibitor abiraterone (used as the free base) is active in the assay used.

TABLE 3

| Inhibition of human CYP17 | |
|---|---|
| Example compound | $IC_{50} \pm SD$ (μM) CYP17 |
| Abiraterone | 0.029 ± 0.004 |
| 4 | $IC_{50} > 20$ μM |
| 20 | $IC_{50} > 20$ μM |

EXAMPLE 51

AKR1C1,2,4-Inhibitory Action

The AKR1C1/AKR1C2/AKR1C4-inhibitory action of the inventive substances, for determination of the selectivity of this invention, was measured in the assay described in the paragraphs which follow.

Essentially, the enzyme activity is measured by the quantification of NADPH (nicotinamide adenine dinucleotide phosphate) consumption in the conversion of phenanthrenequinone (PQ) by the AKR1C enzymes.

The enzymes used were recombinant human AKR1C1, AKR1C2 and AKR1C4 (aldo-keto reductase family 1 members C1, 2 and 4) (GenBank Accession No. NM_001353.5, NM_001354, NM_001818). This was expressed as the GST (glutathione S-transferase) fusion protein in *E. coli* and purified by means of glutathione-Sepharose affinity chromatography. The GST was removed by thrombin digestion with subsequent size exclusion chromatography (Dufort, I., Rheault, P., Huang, X F., Soucy, P., and Luu-The, V., Endocrinology 140, 568-574 (1999)).

For the assay, 50 nl of a 100-fold concentrated solution of the test substance in DMSO and 90 μl of assay buffer [50 mM potassium phosphate buffer pH 7, 0.0022% (w/v) Pluronic F-127, 0.02% BSA (w/v), 170 μM NADPH, 100 nM PQ] were pipetted into a black 96-well microtitre plate (Greiner Bio-One, Frickenhausen, Germany). To start the reaction 10 μl of enzyme [20 nM] were added and the fluorescence at time 0 was determined at 460 nm (excitation at 355 nm) with a suitable measuring instrument. The mixture was incubated at 37° C. for 3 h, and the fluorescence was determined at the end of the reaction.

The difference in the fluorescence intensities was used as a measure for the consumption of NADPH and hence for the enzyme activity of AKRIC1, -2 and -4. The data were normalized (enzyme reaction without inhibitor=0% inhibition; all other assay components but no enzyme=100% inhibition). Typically, the test substances were tested on the same microtitre plate in 10 different concentrations in the range from 10 μM to 1 pM (10 μM, 1 μM, 100 nM, 10 nM, 1 nM, 100 pM, 10 pM, 1 pM). As described, the pharmacological substances claimed were tested for their inhibitory effect on AKR1C enzymes 1, 2 and 4 (see Table 4).

TABLE 4

Inhibition of AKR1C1, -2 and -4 by the inventive compounds
(the values reported are for two experimental determinations)

| Example compound | AKR1C1 enzyme inhibition $IC_{50}$ [nmol/l] | AKR1C2 enzyme inhibition $IC_{50}$ [nmol/l] | AKR1C4 enzyme inhibition $IC_{50}$ [nmol/l] |
|---|---|---|---|
| 1 | no effect | no effect | no effect |
| 1 | no effect | no effect | no effect |
| phenolphthalein | 46 | 554 | 21 |
| phenolphthalein | 60 | 438 | 17 |

EXAMPLE 52

Kinetic Solubility

The kinetic solubilities of the inventive substances were determined by laser nephelometry.

The data were recorded using the following instruments:
Liquid handling system: Hamilton Star
Nephelometer: Nepheloskan Ascent
The following chemicals and materials were used:
DMSO
disodium hydrogenphosphate dihydrate
potassium dihydrogenphosphate
gum arabic
Preparation of phosphate buffer pH 7.4:
Solution 1: 9.71 g of disodium hydrogenphosphate dihydrate and
1.65 g of potassium dihydrogenphosphate dissolved in 1 liter of water
Solution 2: 10 mg of gum arabic dissolved in 1 liter of water
150 ml of solution 1 and 100 ml of solution 2 were diluted with 750 ml of water.
Experimental Protocol:
150 μl of a 10 mM DMSO stock solution were pipetted into a plate (deep-well plate, Abgene, PP, 1.2 ml). The stock solution was diluted with DMSO, which led to a new multi-titre plate (MTP, Greiner bio-one, PS, V-Form) with eight concentrations: 10/5/2.5/1.25/0.625/0.313/0.156 and 0.078 mM. 261 µl of phosphate buffer were transferred into a further plate (96 cliniplate, UB Thermo Electron Corporation) and admixed with 9 µl of the DMSO stock solutions.

The concentration of the DMSO cosolvent was kept constant at 3%.

The plates obtained (cliniplates) were analysed in the nephelometer.

The following nephelometric solubilities were determined:

| Example | Nephelometric solubility [mg/l] at pH = 7.4 |
|---|---|
| 21 | 158 |
| 22 | 153 |
| 28 | 166 |
| 29 | 24 |
| 33 | 80 |
| 35 | 22 |
| 38 | 145 |
| 40 | 145 |
| 43 | 154 |
| EM-1404 | 18 |

EXAMPLE 53

Determination of Antiandrogenic Action

The antiandrogenic action of the substance was measured in adult monkeys (*Macaca fascicularis*), as a surrogate for the antiproliferative effects in prostate cancer and metastases thereof. The monkeys (4 per group) were treated by the oral route by means of a gavage with 1, 3 or 10 mg/kg substance or with vehicle over 4 weeks. The size of the prostate and of the seminal vesicle was determined by ultrasound at the start of the experiment and after one, two, three and four weeks. The decrease in the weight of these organs was taken as evidence for the antiandrogenicity of the substances. In addition, the blood concentrations (in the serum or in the plasma) of various steroids (DHEA, testosterone, androstenedione, hydroxyprogesterone) and prostaglandins (PGD2, PGJ2, PGF2alpha) were determined at the start of the experiment and after one, two, three or four weeks. Since AKR1C3 is involved both in the steroid synthesis route and in the prostaglandin synthesis route, changes in the blood concentrations of these steroids and prostaglandins are taken as an indication of the in vivo effect of the substances.

The invention claimed is:
1. A compound of the general formula (I)

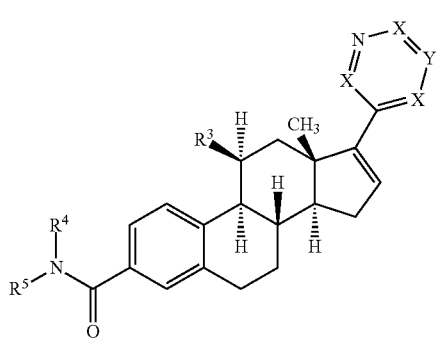

(I)

where
X is independently carbon or nitrogen, where the carbon is optionally substituted by $R^1$,
Y is carbon or nitrogen, where the carbon is optionally substituted by $R^2$,
$R^1$ and $R^2$
are each independently hydrogen, halogen, $C_1$-$C_6$-alkyl, $C_2$-$C_6$-alkenyl, $C_2$-$C_6$-alkynyl, $C_3$-$C_6$-cycloalkyl, $C_1$-$C_6$-alkoxy, $C_1$-$C_6$-haloalkyl, $C_1$-$C_6$-haloalkoxy, nitrile, nitro, —SO$_2$CH$_3$, —SO$_2$CH$_2$CH$_3$, —(C═O)CH$_3$, carboxyl, hydroxyl, —NH$_2$, —CH$_2$NH$_2$, —CH$_2$OH, —CH(OH)CH$_3$, —C(CH$_3$)$_2$OH, —(C═O)NH$_2$, —(C═O)NHCH$_3$, —(C═O)NHCH$_2$CH$_3$, —(C═O)N(CH$_3$)$_2$, —SO$_2$NH$_2$, —SO$_2$NHCH$_3$, —SO$_2$N(CH$_3$)$_2$,
$R^3$ is hydrogen or halogen,
$R^4$ is hydrogen, $C_1$-$C_6$-alkyl, $C_3$-$C_6$-cycloalkyl or $C_3$-$C_6$-cycloalkyl-$C_1$-$C_6$-alkyl, which are optionally substituted by up to 6 halogen atoms and are optionally mono- or disubstituted by hydroxyl, $C_1$-$C_6$-alkoxy, $C_1$-$C_6$-haloalkoxy,
$R^5$ is hydrogen, $C_1$-$C_6$-alkyl or $C_3$-$C_6$-cycloalkyl, where $C_1$-$C_6$-alkyl and $C_3$-$C_6$-cycloalkyl are optionally substituted by up to 6 halogen atoms and are optionally mono- or disubstituted by hydroxyl, hydroxy-$C_1$-$C_6$-alkyl, $C_1$-$C_6$-alkyl, $C_1$-$C_6$-alkoxy, hydroxy-$C_2$-$C_6$-alkoxy, $C_1$-$C_6$-haloalkoxy, $C_3$-$C_6$-cycloalkyl, aryl, heteroaryl, 3-10-membered heterocycloalkyl, aryl-$C_1$-$C_6$-alkyl, heteroaryl-$C_1$-$C_6$-alkyl, —C(═O)R', —C(═O)NH$_2$, —C(═O)N(H)R', —C(═O)N(R')R'', —NH$_2$, —NHR'—N(R')R'', —N(H)C(═O)R', —N(R')C(═O)R', —N(H)C(═O)OR', —N(R')C(═O)OR', —NO$_2$, —N(H)S(═O)R', —N(R')S(═O)R', —N(H)S(═O)$_2$R', —N(R')S(═O)$_2$R', —N═S(═O)(R')R'', —S(═O)R', —S(═O)$_2$R', —S(═O)$_2$NH$_2$, —S(═O)$_2$NHR', —S(═O)$_2$N(R')R'', —S(═O)(═NR')R'', where aryl, heteroaryl, aryl-$C_1$-$C_6$-alkyl and heteroaryl-$C_1$-$C_6$-alkyl are optionally each independently mono- or polysubstituted by $R^6$, and 3-10-membered heterocycloalkyl is optionally independently mono- or polysubstituted by R', or
$R^4$ and $R^5$ together with the directly joining nitrogen atom are a 4-7-membered ring which is optionally substituted by one or two substituents from the group consisting of:
halogen, nitrile, hydroxyl, $C_1$-$C_6$-alkyl, $C_1$-$C_6$-haloalkyl, $C_2$-$C_6$-alkenyl, $C_2$-$C_6$-alkynyl, $C_3$-$C_{10}$-cycloalkyl, aryl, heteroaryl,
—C(═O)NH$_2$, —C(═O)N(H)R', —C(═O)N(R')R'', —C(═O)OH, —C(═O)OR', —NH$_2$, —NHR', —N(R')R'', —N(H)C(═O)R', —N(R')C(═O)R', —N(H)S(═O)R', —N(R')S(═O)R', —N(H)S(═O)$_2$R', —N(R')S(═O)$_2$R', —N═S(═O)(R')R'', —OH,
$C_1$-$C_6$-alkoxy, $C_1$-$C_6$-haloalkoxy, —OC(═O)R', —OC(═O)NH$_2$, —OC(═O)NHR', —OC(═O)N(R')R'', —SH, $C_1$-$C_6$-alkyl-S—, —S(═O)R', —S(═O)$_2$R', —S(═O)$_2$NH$_2$, —S(═O)$_2$NHR', —S(═O)$_2$N(R')R'', where aryl and heteroaryl are optionally each independently mono- or polysubstituted by $R^6$,
and in which 5-, 6- or 7-membered ring one or more methylene groups are optionally replaced by NH, NR', O or S,
$R^6$ is halogen, nitrile, $C_1$-$C_6$-alkyl, $C_1$-$C_6$-haloalkyl, $C_2$-$C_6$-alkenyl, $C_2$-$C_6$-alkynyl, $C_3$-$C_{10}$-cycloalkyl, 3-10-membered heterocycloalkyl, aryl, heteroaryl, —C(═O)R', —C(═O)NH$_2$, —C(═O)N(H)R', —C(═O)N(R')R'', —C(═O)OR', —NH$_2$, —NHR', —N(R')R", —N(H)C(=O)R', —N(R')C(=O)R', —N(H)C(=O)NH$_2$, —N(H)C(=O)NHR', —N(H)C(=O)N(R')R", —N(R')C(=O)NH$_2$, —N(R')C(=O)NHR', —N(R')C(=O)N(R')R", —N(H)C(=O)OR', —N(R')C(=O)OR', —NO$_2$, —N(H)S(=O)R', —N(R')S(=O)R', —N(H)S(=O)$_2$R', —N(R')S(=O)$_2$R', —N=S(=O)(R')R", —OH, C$_1$-C$_6$-alkoxy, C$_1$-C$_6$-haloalkoxy, —OC(=O)R', —OC(=O)NH$_2$, —OC(=O)NHR', —OC(=O)N(R')R", —SH, C$_1$-C$_6$-alkyl-S—, —S(=O)R', —S(=O)$_2$R', —S(=O)$_2$NH$_2$, —S(=O)$_2$NHR', —S(=O)$_2$N(R')R", —S(=O)(=NR')R", R' and R" are each independently C$_1$-C$_6$-alkyl, C$_3$-C$_{10}$-cycloalkyl or C$_1$-C$_6$-haloalkyl, or the stereoisomers, tautomers, N-oxides, or salts thereof.

2. The compound of claim 1,
wherein
X is carbon substituted by hydrogen,
Y is carbon or nitrogen, where the carbon is optionally substituted by R$^2$,
R$^2$ is hydrogen, fluorine, chlorine, nitrile, methoxy, ethoxy, trifluoromethoxy, methyl, ethyl, trifluoromethyl, —C(=O)CH$_3$,
R$^3$ is hydrogen or fluorine,
R$^4$ is hydrogen, methyl, ethyl, isopropyl, propyl, butyl, cyclopropyl or 2,2,2-trifluoroethyl,
R$^5$ is hydrogen, methyl, ethyl, propyl, 2,2,2-trifluoroethyl, 3,3,3-trifluoropropyl, 2-fluoroethyl, 2-sulphamoylethyl, 3-sulphamoylpropyl, (1S,2R)-2-hydroxycyclopentyl, 3-hydroxy-2,2-dimethylpropyl, (1S,2S)-2-hydroxycyclopentyl, (3R)-4-hydroxy-3-methylbutyl, 1-(hydroxymethyl)cyclopentyl, (2S)-1-hydroxybutan-2-yl, (2R)-1-hydroxy-3-methylbutan-2-yl, 3-hydroxybutan-2-yl, 2-hydroxyethyl, 3,3,3-trifluoro-2-hydroxypropyl, 2-(1H-tetrazol-5-yl)ethyl, 1H-tetrazol-5-ylmethyl, 2-(methylsulphamoyl)ethyl, 3-amino-3-oxopropyl, 3-(methylamino)-3-oxopropyl, 2-methyl-2-[(methylsulphonyl)amino]propyl, (2S)-2,3-dihydroxypropyl, 3-hydroxypropyl, 4-hydroxybutyl, (2RS)-2,3-dihydroxypropyl, (2R)-2,3-dihydroxypropyl, 2,3-dihydroxybutyl, 2-(methylsulphinyl)ethyl, 3-(methylsulphinyl)propyl, 2-(methyl sulphonyl)ethyl, 3-(methylsulphonyl)propyl, 2-(S-methylsulphonimidoyl)ethyl, (2R)-2-hydroxypropyl, (2S)-1-hydroxypropan-2-yl, 2-methoxyethyl, 3-methoxypropyl, 2-(isopropylsulphonyl)ethyl, (3-methyloxetan-3-yl)methyl, (2S)-2-hydroxypropyl, 2-(2-hydroxyethoxy)ethyl, or R$^4$ and R$^5$ together with the directly joining nitrogen atom are piperidinyl, pyrrolidinyl, morpholinyl, N-methylpiperazinyl, 1-oxidothiomorpholinyl, 1,1-dioxidothiomorpholin-4-yl, 4-hydroxypiperidinyl, 4-(trifluoromethyl)piperidin-4-yl, (3R)-3-hydroxypiperidinyl, (2S)-2-(1H-tetrazol-5-yl)pyrrolidinyl, N-methyl-L-prolinamidyl and L-prolinamidyl,
or the stereoisomers, tautomers, N-oxides, or salts thereof.

3. The compound of claim 1,
wherein
X is carbon substituted by hydrogen,
Y is carbon or nitrogen, where the carbon is optionally substituted by R$^2$,
R$^2$ is hydrogen, fluorine, chlorine, methyl, nitrile, methoxy, trifluoromethyl,
R$^3$ is hydrogen or fluorine,
R$^4$ is hydrogen, methyl, ethyl, isopropyl, propyl or cyclopropyl,
R$^5$ is hydrogen, methyl, ethyl, 2-sulphamoylethyl, 3-sulphamoylpropyl, (1S,2R)-2-hydroxycyclopentyl, 3-hydroxy-2,2-dimethylpropyl, (1S,2S)-2-hydroxycyclopentyl, (3R)-4-hydroxy-3-methylbutyl, 1-(hydroxymethyl)cyclopentyl, (2S)-1-hydroxybutan-2-yl, (2R)-1-hydroxy-3-methylbutan-2-yl, 3-hydroxybutan-2-yl, 2-hydroxyethyl, 3,3,3-trifluoro-2-hydroxypropyl, 2-(1H-tetrazol-5-yl)ethyl, 1H-tetrazol-5-ylmethyl, 2-(methylsulphamoyl)ethyl, 3-amino-3-oxopropyl, 3-(methylamino)-3-oxopropyl, 2-methyl-2-[(methylsulphonyl)amino]propyl, (2S)-2,3-dihydroxypropyl, 3-hydroxypropyl, (2RS)-2,3-dihydroxypropyl, (2R)-2,3-dihydroxypropyl, 2-(methylsulphinyl)ethyl, (2R)-2-hydroxypropyl, (2S)-1-hydroxypropan-2-yl, 2-methoxyethyl, 2-(isopropylsulphonyl)ethyl, (3-methyloxetan-3-yl)methyl, (2S)-2-hydroxypropyl or 2-(2-hydroxyethoxy)ethyl or R$^4$ and R$^5$ together with the directly joining nitrogen atom are piperidinyl, pyrrolidinyl, morpholinyl, 4-hydroxypiperidinyl, (3R)-3-hydroxypiperidinyl, (2S)-2-(1H-tetrazol-5-yl)pyrrolidinyl, N-methyl-L-prolinamidyl or L-prolinamidyl
or the stereoisomers, tautomers, N-oxides, or salts thereof.

4. The compound of claim 1,
wherein
X is carbon substituted by hydrogen,
Y is carbon or nitrogen, where the carbon is optionally substituted by R$^2$,
R$^2$ is hydrogen, fluorine, nitrile, methoxy or trifluoromethyl,
R$^3$ is hydrogen or fluorine,
R$^4$ is hydrogen, methyl, ethyl or isopropyl,
R$^5$ is hydrogen, ethyl, 2-sulphamoylethyl, (1S,2R)-2-hydroxycyclopentyl, 3-hydroxy-2,2-dimethylpropyl, (1S,2S)-2-hydroxycyclopentyl, (3R)-4-hydroxy-3-methylbutyl, 1-(hydroxymethyl)cyclopentyl, (2S)-1-hydroxybutan-2-yl, (2R)-1-hydroxy-3-methylbutan-2-yl, 3-hydroxybutan-2-yl, 2-hydroxyethyl, 3,3,3-trifluoro-2-hydroxypropyl, 2-(1H-tetrazol-5-yl)ethyl, 1H-tetrazol-5-ylmethyl, 2-(methylsulphamoyl)ethyl, 3-amino-3-oxopropyl, 3-(methylamino)-3-oxopropyl, 2-methyl-2-[(methylsulphonyl)amino]propyl, (2S)-2,3-dihydroxypropyl, 3-hydroxypropyl, (2RS)-2,3-dihydroxypropyl, (2R)-2,3-dihydroxypropyl, 2-(methylsulphinyl)ethyl, (2R)-2-hydroxypropyl, (2S)-1-hydroxypropan-2-yl, 2-methoxyethyl, 2-(isopropylsulphonyl)ethyl, (3-methyloxetan-3-yl)methyl, (2S)-2-hydroxypropyl or 2-(2-hydroxyethoxy)ethyl, or R$^4$ and R$^5$ together with the directly joining nitrogen atom are 4-hydroxypiperidinyl, (3R)-3-hydroxypiperidinyl, (2S)-2-(1H-tetrazol-5-yl)pyrrolidinyl, N-methyl-L-prolinamidyl or L-prolinamidyl
or the stereoisomers, tautomers, N-oxides, or salts thereof.

5. A compound of claim 1, selected from the group consisting of:
17-(3-pyridyl)oestra-1,3,5(10),16-tetraene-3-carboxamide;
17-(5-methoxypyridin-3-yl)oestra-1,3,5(10),16-tetraene-3-carboxamide;
17-[5-(trifluoromethyl)pyridin-3-yl]oestra-1,3,5(10),16-tetraene-3-carboxamide;
17-(5-fluoropyridin-3-yl)oestra-1,3,5(10),16-tetraene-3-carboxamide;
17-(pyrimidin-5-yl)oestra-1,3,5(10),16-tetraene-3-carboxamide;

17-(5-cyanopyridin-3-yl)oestra-1,3,5(10),16-tetraene-3-carboxamide;

11β-fluoro-17-(5-fluoropyridin-3-yl)oestra-1,3,5(10),16-tetraene-3-carboxamide;

11β-fluoro-17-(5-fluoropyridin-3-yl)-N-(2-sulphamoylethyl)oestra-1,3,5(10),16-tetraene-3-carboxamide;

17-(5-fluoropyridin-3-yl)-N-[(1S,2R)-2-hydroxycyclopentyl]oestra-1,3,5(10),16-tetraene-3-carboxamide;

17-(5-fluoropyridin-3-yl)-N-[2-(hydroxymethyl)-2-methylpropyl]oestra-1,3,5(10),16-tetraene-3-carboxamide;

17-(5-fluoropyridin-3-yl)-N-[(1S,2S)-2-hydroxycyclopentyl]oestra-1,3,5(10),16-tetraene-3-carboxamide;

17-(5-fluoropyridin-3-yl)-N—[(R)-3-(hydroxymethyl)butyl]oestra-1,3,5(10),16-tetraene-3-carboxamide, 17-(5-fluoropyridin-3-yl)-N-[1-(hydroxymethyl)cyclopentyl]oestra-1,3,5(10),16-tetraene-3-carboxamide;

17-(5-fluoropyridin-3-yl)oestra-1,3,5(10),16-tetraen-3-yl 4-hydroxypiperidin-1-yl ketone;

17-(5-fluoropyridin-3-yl)-N—[(S)-1-(hydroxymethyl)propyl]oestra-1,3,5(10),16-tetraene-3-carboxamide;

17-(5-fluoropyridin-3-yl)-N—[(R)-1-(hydroxymethyl)-2-methylpropyl]oestra-1,3,5(10),16-tetraene-3-carboxamide;

17-(5-fluoropyridin-3-yl)oestra-1,3,5(10),16-tetraen-3-yl (R)-3-hydroxypiperidin-1-yl ketone;

rel-17-(5-fluoropyridin-3-yl)-N-[(1R,2R)-2-hydroxy-1-methylpropyl]oestra-1,3,5(10),16-tetraene-3-carboxamide;

17-(5-fluoropyridin-3-yl)-N-(2-hydroxy ethyl)-N-isopropyloestra-1,3,5(10),16-tetraene-3-carboxamide;

17-(5-fluoropyridin-3-yl)-N—[(RS)-3,3,3-trifluoro-2-hydroxypropyl]oestra-1,3,5(10),16-tetraene-3-carboxamide;

17-(5-fluoropyridin-3-yl)-N-[2-(1H-tetrazol-5-yl)ethyl] oestra-1,3,5(10),16-tetraene-3-carboxamide;

17-(5-fluoropyridin-3-yl)-N-(1H-tetrazol-5-ylmethyl)oestra-1,3,5(10),16-tetraene-3-carboxamide;

17-(3-pyridyl)-N-(2-sulphamoylethyl)oestra-1,3,5(10),16-tetraene-3-carboxamide;

N-(2-sulphamoylethyl)-17-[5-(trifluoromethyl)pyridin-3-yl]oestra-1,3,5(10),16-tetraene-3-carboxamide;

N-[2-(N-methylsulphamoyl)ethyl]-17-[5-(trifluoromethyl)pyridin-3-yl]oestra-1,3,5(10),16-tetraene-3-carboxamide;

N-(3-amino-3-oxopropyl)-17-(5-fluoropyridin-3-yl)oestra-1,3,5(10),16-tetraene-3-carboxamide;

17-(5-fluoropyridin-3-yl)-N-[3-(methylamino)-3-oxopropyl]oestra-1,3,5(10),16-tetraene-3-carboxamide;

17-(5-fluoropyridin-3-yl)oestra-1,3,5(10),16-tetraen-3-yl (S)-2-(1H-tetrazol-5-yl)pyrrolidin-1-yl ketone;

1-{[17-(5-fluoropyridin-3-yl)oestra-1,3,5(10),16-tetraen-3-yl]carbonyl}-N-methyl-L-prolinamide;

1-{[17-(5-fluoropyridin-3-yl)oestra-1,3,5(10),16-tetraen-3-yl]carbonyl}-L-prolinamide;

17-(5-fluoropyridin-3-yl)-N-{2-methyl-2-[(methyl sulphonyl)amino]propyl}oestra-1,3,5(10),16-tetraene-3-carboxamide;

N-ethyl-17-(5-fluoropyridin-3-yl)-N-(2-hydroxy ethyl)oestra-1,3,5(10),16-tetraene-3-carboxamide;

N—[(S)-2,3-dihydroxypropyl]-17-(5-fluoropyridin-3-yl)oestra-1,3,5(10),16-tetraene-3-carboxamide;

17-(5-fluoropyridin-3-yl)-N-(3-hydroxypropyl)-N-methyloestra-1,3,5(10),16-tetraene-3-carboxamide;

N—[(RS)-2,3-dihydroxypropyl]-17-(5-fluoropyridin-3-yl)-N-methyloestra-1,3,5(10),16-tetraene-3-carboxamide;

N—[(R)-2,3-dihydroxypropyl]-17-(5-fluoropyridin-3-yl)oestra-1,3,5(10),16-tetraene-3-carboxamide;

17-(5-fluoropyridin-3-yl)-N-[2-(methylsulphinyl)ethyl]oestra-1,3,5(10),16-tetraene-3-carboxamide;

17-(5-fluoropyridin-3-yl)-N—[(R)-2-hydroxypropyl]oestra-1,3,5(10),16-tetraene-3-carboxamide;

N-ethyl-17-(5-fluoropyridin-3-yl)oestra-1,3,5(10),16-tetraene-3-carboxamide;

1-(5-fluoropyridin-3-yl)-N—[(S)-1-(hydroxymethyl)ethyl]oestra-1,3,5(10),16-tetraene-3-carboxamide;

17-(5-fluoropyridin-3-yl)-N-(2-methoxyethyl)oestra-1,3,5(10),16-tetraene-3-carboxamide;

17-(5-fluoropyridin-3-yl)-N-[2-(isopropylsulphonyl)ethyl]oestra-1,3,5(10),16-tetraene-3-carboxamide;

17-(5-fluoropyridin-3-yl)-N-[(3-methyloxetan-3-yl)methyl]oestra-1,3,5(10),16-tetraene-3-carboxamide;

17-(5-fluoropyridin-3-yl)-N-(2-hydroxy ethyl)-N-methyl-oestra-1,3,5(10),16-tetraene-3-carboxamide;

17-(5-fluoropyridin-3-yl)-N—[(S)-2-hydroxypropyl]oestra-1,3,5(10),16-tetraene-3-carboxamide;

17-(5-fluoropyridin-3-yl)-N-[2-(2-hydroxy ethoxy)ethyl]oestra-1,3,5(10),16-tetraene-3-carboxamide; and 17-(pyrimidin-5-yl)-N-(2-sulphamoylethyl)oestra-1,3,5(10),16-tetraene-3-carboxamide;

or the stereoisomers, tautomers, N-oxides, or salts thereof.

6. A medicament comprising a compound of claim 1 and an inert, nontoxic, pharmaceutically suitable excipient.

7. A medicament comprising a compound as defined in claim 1 and at least one active ingredient selected from the group consisting of a selective oestrogen receptor modulator (SERM), an oestrogen receptor (ER) antagonist, an aromatase inhibitor, a 17-HSD1 inhibitor, a steroid sulphatase (STS) inhibitor, a GnRH agonist and antagonist, a kisspeptin receptor (KISSR) antagonist, a selective androgen receptor modulator (SARM), an androgen, a 5-reductase inhibitor, a selective progesterone receptor modulator (SPRM), a gestagen, an antigestagen, an oral contraceptive, an inhibitors of mitogen-activated protein (MAP) kinase and inhibitors of the MAP kinases (Mkk3/6, Mek1/2, Erk1/2), an inhibitors of the protein kinase B (PKBα/β/γ; Akt1/2/3), an inhibitor of the phosphoinositide 3-kinase (PI3K), an inhibitor of cyclin-dependent kinase (CDK1/2), an inhibitors of the hypoxia-induced signalling pathway (HIF1alpha inhibitor, an activator of prolylhydroxylase), a histone deacetylase (HDAC) inhibitor, a prostaglandin F receptor (FP) (PTGFR) antagonist, and a non-steroidal inflammation inhibitor (NSAID).

8. The medicament of claim 7, wherein the medicament is in the form of a pharmaceutical formulation for enteral, parenteral, vaginal, intrauterine and oral administration.

9. A method of alleviating endometriosis, leiomyoma, dysmenorrhoea, prostate carcinoma, prostate hyperplasia, acne, seborrhoea, hair loss, premature sexual maturity, polycystic ovary syndrome, breast cancer, lung cancer, endometrial carcinoma, renal cell carcinoma, bladder carcinoma, non-Hodgkins lymphoma, chronic obstructive pulmonary disease (COPD), or obesity, comprising administering to a human or animal an effective amount of a compound of claim 1.

10. A method of alleviating endometriosis, uterine leiomyoma, dysmenorrhoea, prostate carcinoma, prostate hyperplasia, acne, seborrhoea, hair loss, premature sexual maturity, polycystic ovary syndrome, breast cancer, lung cancer, endometrial carcinoma, renal cell carcinoma, bladder carcinoma, non-Hodgkins lymphoma, chronic obstructive pulmonary disease (COPD), or obesity, comprising administering the medicament of claim 7 to a human or animal in need thereof.

\* \* \* \* \*